US008779151B2

(12) United States Patent
Priebe et al.

(10) Patent No.: US 8,779,151 B2
(45) Date of Patent: Jul. 15, 2014

(54) ORALLY BIOAVAILABLE CAFFEIC ACID RELATED ANTICANCER DRUGS

(75) Inventors: Waldemar Priebe, Houston, TX (US); Izabela Fokt, Houston, TX (US); Slawomir Szymanski, Houston, TX (US); Timothy Madden, Sugar Land, TX (US); Jeffrey Myers, Bellaire, TX (US); Charles Conrad, Spring, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 847 days.

(21) Appl. No.: 11/695,547

(22) Filed: Apr. 2, 2007

(65) Prior Publication Data

US 2007/0232668 A1    Oct. 4, 2007

Related U.S. Application Data

(60) Provisional application No. 60/744,105, filed on Mar. 31, 2006.

(51) Int. Cl.
C07D 213/57    (2006.01)
A61K 31/44    (2006.01)

(52) U.S. Cl.
USPC ............ 546/330; 514/357; 558/390; 558/392

(58) Field of Classification Search
USPC ............ 546/300, 330; 514/357; 558/392, 390
See application file for complete search history.

(56) References Cited

U.S. PATENT DOCUMENTS

| | | | | |
|---|---|---|---|---|
| 4,999,357 | A | 3/1991 | Gadras et al. | 514/277 |
| 5,196,446 | A | 3/1993 | Levitzki et al. | 514/415 |
| 5,700,822 | A | 12/1997 | Hirth et al. | 514/380 |
| 5,773,476 | A | 6/1998 | Chen et al. | 514/620 |
| 5,854,285 | A | 12/1998 | Sriram et al. | 514/514 |
| 5,981,569 | A | 11/1999 | App et al. | 514/419 |
| 6,194,453 | B1 | 2/2001 | Sriram et al. | 514/514 |
| 6,225,346 | B1 | 5/2001 | Tang et al. | 514/523 |
| 6,331,555 | B1 | 12/2001 | Hirth et al. | 514/378 |
| 6,420,338 | B1 | 7/2002 | Schneider et al. | 514/12 |
| 6,426,366 | B1 | 7/2002 | Novogrodsky et al. | 514/523 |
| 6,433,018 | B1 | 8/2002 | Siddiqui et al. | 514/619 |
| 6,555,702 | B2 | 4/2003 | Sriram et al. | 558/401 |
| 6,596,828 | B1 | 7/2003 | Kaito et al. | 526/164 |
| 6,596,878 | B2 | 7/2003 | Chen et al. | 548/371.7 |
| 2002/0045191 | A1 | 4/2002 | Schneider et al. | 435/7.1 |
| 2002/0115714 | A1 | 8/2002 | Sriram et al. | 514/514 |
| 2003/0013748 | A1 | 1/2003 | Novogrodsky et al. | 514/367 |
| 2003/0032596 | A1 | 2/2003 | Schneider et al. | 514/12 |

FOREIGN PATENT DOCUMENTS

| | | |
|---|---|---|
| JP | 2003-119169 | 4/2003 |
| WO | WO 91/16305 | 10/1991 |
| WO | WO 95/14464 | 6/1995 |
| WO | WO 95/18606 | 7/1995 |
| WO | WO 95/24190 | 9/1995 |
| WO | WO 98/06391 | 2/1998 |
| WO | WO 2004-047743 | 6/2004 |
| WO | WO 2005/053671 | 6/2005 |
| WO | WO 2005/058829 | 6/2005 |

OTHER PUBLICATIONS

Murata et. al. "Synthesis and structure-activity relationships of novel IKK-b inhibitors. Part 3: Orally active anti-inflammatory agents" Bioorganic & Medicinal Chemistry Letters 2004, 14, 4019-4022.*
PCT International Search Report and Written Opinion, issued in International Application No. PCT/US2007/065805, dated Oct. 17, 2007.
"Design, Synthesis and Structure-Activity Relationships of Novel Jak2/STAT3 Signaling Inhibitors," AACR Abtract Later Breaking News, Feb. 1, 2006 (Abstract No. 06-LBA-8902-AACR).
Alas and Bonavida, "Inhibition of constitutive STAT3 activity sensitizes resistant non-Hodgkin's lymphoma and multiple myeloma to chemotherapeutic drug-mediated apoptosis," *Clin. Cancer Res.*, 9(1):316-26, 2003.
Alcon et al., "Activation of Tyrosine Kinase Pathway by Vanadate in Gallbladder Smooth Muscle," *Biochem. Pharmacol.*, 59:1077-1089, 2000.
Arbel et al., "Inhibitors that target protein kinases for the treatment of ovarian carcinoma," *Am. J. Obstet. Gynecol.*, 188(5):1283-90, 2003.
Bharti et al., "Curcumin (diferuloylmethane) inhibits constitutive and IL-6-inducible STAT3 phosphorylation in human multiple myeloma cells," *J. Immunol.*, 171(7):3863-3871, 2003.
Burdelya et al., "Combination therapy with AG-490 and interleukin 12 achieves greater antitumor effects than either agent alone," *Mol. Cancer Ther.*, 1(11):893-9, 2002.
Catlett-Falcone et al., "Constitutive activation of Stat3 signaling confers resistance to apoptosis in human U266 myeloma cells," *Immunity*, 10(1):105-15, 1999.
Chen et al., "Human pancreatic adenocarcinoma: in vitro and in vivo morphology of a new tumor line established from ascites," in Vitro, 18(1):24-34, 1982.
Constantin et al., "Tyrphostin AG490, a tyrosine kinase inhibitor, blocks actively induced experimental autoimmune encephalomyelitis," *Eur. J. Immunol.*, 28(11):3523-9, 1998.
De Vos et al., "JAK2 tyrosine kinase inhibitor tyrphostin AG490 downregulates the mitogen-activated protein kinase (MAPK) and signal trasducer and activator of transcription (STAT) pathways and induces apoptosis in myeloma cells," *Br. J. Haematol.* 109:823-828, 2000.
Gazit et al., "Tyrphostins. 2. Heterocyclic and alpha-substituted benzylidenomalononitrile tyrphostins as potent inhibitors of EG receptor and ErbB2/nue tyrosine kinases, "*J. Med. Chem.*, 34(6):1896-1907, 1991.
Gazit, et al., "Tyrphostins I: synthesis and biological activity of protein tyrosine kinase inhibitors," *J. Med. Chem.*, 32:2344-2352, 1989.
Hallek et al., "Multiple myeloma: increasing evidence for a multistep transformation process," *Blood*, 91(1):3-21, 1998.

(Continued)

*Primary Examiner* — David K O Dell
(74) *Attorney, Agent, or Firm* — Parker Highlander PLLC

(57) ABSTRACT

The present invention concerns compounds and their use to treat cell proliferative diseases such as cancer. Compounds of the present invention display significant potency as inhibitors of Jak2/STAT3 pathways and downstream targets and inhibit the growth and survival of cancerous cell lines.

27 Claims, 34 Drawing Sheets

(56) References Cited

OTHER PUBLICATIONS

Hideshima et al., "NF-kappa B as a therapeutic target in multiple myeloma," *J. Biol. Chem.*, 277(19):16639-16647, 2002.

Iwamaru et al., "A novel inhibitor of the STAT3 pathway induces apoptosis in malignant glioma cells both in vitro and in vivo," *Oncogene*, 26: 2435-44, 2007.

Jernberg-Wiklund et al., "Expression of myc-family genes in established human multiple myeloma cell lines: L-myc but not c-myc gene expression in the U-266 myeloma cell line," *Int. J. Cancer*, 51(1):116-123, 1992.

Kerr et al., "Of JAKs, STATs, blind watchmakers, jeeps and trains," *FEBS Lett.*, 546(1):1-5, 2003.

Kirken et al., "Tyrphostin AG0490 inhibits cytokine-mediated JAK3/STAT5a/b signal transduction and cellular proliferation of antigen-activated human T cells," *J.Leukoc. Biol.*, 65:891-899, 1999.

Kuehl et al., "Dysregulation of c-myc in multiple myeloma," *Curr. Top Microbiol. Immunol.*, 224:277-282, 1997.

Levitzki et al., "Tyrphostins-Potential antiproliferative agents and novel molecular tools," *Biochem. Pharmacol.* 40:913-918, 1990.

Lieber et al., "Establishment of a continuous tumor-cell line (panc-1) from a human carcinoma of the exocrine pancreas," *Int. J. Cancer*, 15(5):741-747, 1975.

Meydan et al, "Inhibition of acute lymphoblastic leukaemia by a Jak-2 inhibitor," *Nature* 379:645-648, 1996.

Morgan et al., "Human cell line (colo 357) of metastatic pancreatic adenocarcinoma," *Int. J. Cancer*, 25(5):591-598, 1980.

Renglin et al., "Miotic aberrations induced by carbaryl reflect tyrosine kinase inhibition with coincident up-regulation of serine/threonine protein phosphatase activity: implications for coordination of karyokinesis and cytokinesis," *Mutagenesis.* 14(3):327-334, 1999.

Satyamoorthy et al., "Melanoma cell lines from different stages of progression and their biological and molecular analyses," *Melanoma Res.*, 7(Suppl.2):S35-S42, 1997.

Selvanayagam et al., "Alternation and Abnormal Expression of the c-myc Oncogene in Human Multiple Myeloma," *Blood*, 71(1):30-35, 1988.

Verma et al., "Jak family of kinases in cancer," *Cancer Metastasis Rev.*, 22(4):423-434, 2003.

Vezeridis et al., "In vivo selection of a highly metastatic cell line from a human pancreatic carcinoma in the nude mouse," *Cancer*, 69(8):2060-2063, 1992.

Vezeridis et al., "Heterogeneity of potential for hematogenous metastasis in a human pancreatic carcinoma," *J. Surg. Res.*, 48(1):51-55, 1990.

Volberg et al, "Disruption of Microtubules in Living Cells by Tyrphostin AG-1714," *Cell Motility and the Cytoskelton*, 45(3):223-234; 2000.

Wang et al., "JAK3, STAT, and MAPK signaling pathways as novel molecular target for the tyrphostin AG-490 regulation of IL-2-mediated T cell response," *J. Immunol*, 162:3897-3904, 1999.

Yu and Jove, "The stats of cancer-new molecular targets come of age," *Nature Rev. Cancer*, 4(2):97-105, 2004.

Farooki et al., "Tyrphostins disrupt stress fibers and cellular attachments in endothelial monolayers," *Exp. Cell. Res.*, 243 (1): 185-198, 1998.

Zlotnik et al., "Tyrphostins reduce chemotherapy-induced intestinal injury in mice: assessment by a biochemical assay," *Br. J. Cancer*, 92 (2): 294-297, 2005.

Extended European Search Report and Search Opinion issued in European Application No. 12162385.4, mailed Dec. 10, 2012.

Lee, "Role of NADPH oxidase-mediated generation of reactive oxygen species in the mechanism of apoptosis induced by phenolic acids in HepG2 human hepatoma cells," *Archives of Pharmacal Research*, 28(10):1183-1189, 2005.

Nagaoka et al., "Selective antiproliferative activity of caffeic acid phenethyl ester analogues on highly liver-metastatic murine colon 26-L5 carcinoma cell line," *Bioorganic & Medicinal Chemistry*, 10:3351-3359, 2002.

Orsolic et al., "Effects of local administration of propolis and its polyphenolic compounds on tumor formation and growth," *Biological and Pharmaceutical Bulletin*, 28(10):1928-1933, 2005.

Office Action (English translation included) issued in corresponding Chinese Patent Application No. 200780019917.4, dated Aug. 24, 2011. (received from foreign associate on Sep. 14, 2011).

Office Communication issued in Australian Patent Application No. 2007234455, dated Sep. 6, 2011.

\* cited by examiner

WP1193 more potently than WP1066 inhibits growth of human melanoma tumor cells (WM793 cell line)

ORALLY BIOAVAILABLE CAFFEIC ACID RELATED ANTICANCER DRUGS

The present application claims benefit of priority to U.S. Provisional Application Ser. Nos. 60/744,105, filed Mar. 31, 2006, the entire contents this application being incorporated by reference herein.

The U.S. government owns rights in the present invention pursuant to funding from the National Institute of Health through grant number CA101936.

BACKGROUND OF THE INVENTION

1. Field of the Invention

The present invention relates generally to the treatment of cell proliferative diseases such as cancer. More particularly, it concerns caffeic acid and related analogs useful for the treatment of cell proliferative diseases such as cancer, methods of synthesis of these compounds, and methods of treatment employing these compounds.

2. Description of Related Art

The compound AG490 is a kinase inhibitor that inhibits Janus kinase 2/Signal transducer and activator of transcription-3 (Jak2/STAT3) signaling pathway. AG490 belongs to a group of compounds defined by the parent natural product caffeic acid and its natural derivatives like caffeic acid benzyl ester.

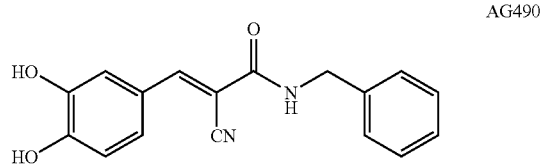 [SMILES: N#C/C(=C\c1ccc(O)c(O)c1)C(=O)NCc1ccccc1]

AG490

Targeted inhibition of the Jak2/STAT3 pathway with caffeic acid analogs such as AG490 inhibits tumor cell growth and increases sensitivity to apoptotic stimuli; thus, inhibitors of this pathway likely represent potential therapeutics for cancer therapy (Catlett-Falcone et al., 1999; Alas and Bonavida, 2003; Burdelya et al., 2002). AG490 would not be considered a drug-like molecule due to its instability in biological matrices (blood, tissues, etc) and a lack of potency (Kondo, et al, 2007; Burdelya et al., 2002; Meydan et al., 1996; Constantin et al., 1998). Receptor-based or direct activation of Jak2/STAT3 pathway by such stimulators such as EGF, scr, and IL-6 (multiple interleukins and cytokines) promoting survival proliferation and angiogenesis of human tumors (Bharti et al., Verma et al., Kerr et al.), requires inhibitors more potent and more stable than AG490 to have potential as anti-cancer drugs.

Jak2/STAT3 signaling pathways participate in the progression of a variety of malignancies. STAT3 is constitutively activated in pancreatic carcinoma, glioblastoma multiforme, and squamous cell carcinoma of the head and neck, among others, and its activation has been shown to affect VEGF expression, angiogenesis, tumor growth, and metastasis in vivo. As such, STAT3 may be an excellent target for drug development (Yu and Jove, 2004). No effective inhibitors are currently available.

AG490, a caffeic acid analog, is sometimes referred descriptively as a tyrphostin. U.S. Pat. No. 6,426,366 and U.S. Patent Publication No. 2003/0013748 describe compounds that have structural similarity with AG490.

AG490, however, has limited activity in animal studies and must be used at high concentrations (~50 to 100 μM) to achieve inhibition of Jak2/STAT3 signaling and anti-tumor effects. This low potency of AG490 is insufficient to warrant clinical investigation of this compound for the treatment of cancer (Burdelya et al., 2002; Meydan et al., 1996; Constantin et al., 1998). Thus a need exists for therapeutics that exhibit strong anti-proliferative effects through a similar mechanism at lower therapeutic concentrations.

SUMMARY OF THE INVENTION

The present invention overcomes limitations in the art by providing compounds that display improved pharmacological profiles (e.g., biostability, bioavailability, enhanced tissue penetration, improved pharmacokinetics, increased potency) when compared with AG490 and other compounds that are structurally related to caffeic acid; these compounds block IL-6 mediated Jak2/STAT3 activation at low micromolar concentrations and suppress related downstream antiapoptotic, proangiogenic and proliferation promoting signaling. The present invention involves compounds that have utility as antitumor and/or chemotherapeutic drugs, methods of synthesizing these compounds, and methods of using these compounds to treat patients with cancer.

Disclosed herein are a new class of compounds that inhibits Jak2 and STAT3 phosphorylation and many of its related downstream targets. It also potently inhibits tumor growth in vitro and in vivo. Unlike AG490, the compounds of the present invention, for example the caffeic acid analogs with cycloalkyl substituents (see below), are highly active against a variety of cancers including pancreatic tumors, such as Colo357-FG, brain tumors, such as U87-MG, D54, U251 and cancer stem cell lines of glioblastoma multiforme, and head and neck tumors, including squamous cell carcinoma cancer cell lines. These compounds inhibit both IL-6, EGF stimulated and constituative STAT3 activation; suppressed the expression of Bcl-2, Bcl-XL, survivin, and Mcl-1; and induced apoptosis, all at low micromolar concentrations.

One aspect of the present invention provides compounds according to the structural formulas shown in Table 1.

TABLE 1

Examples of Different Types of Caffeic Acid Analogs:

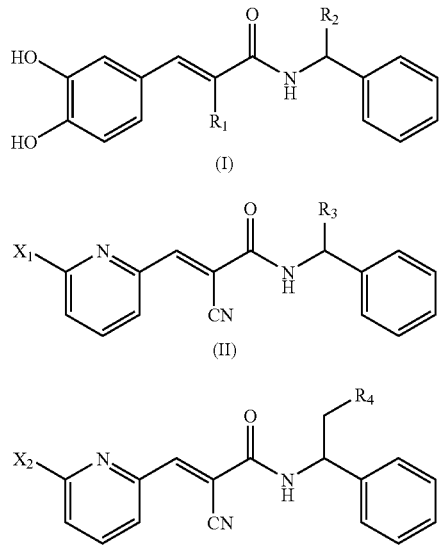

TABLE 1-continued

Examples of Different Types of Caffeic Acid Analogs:

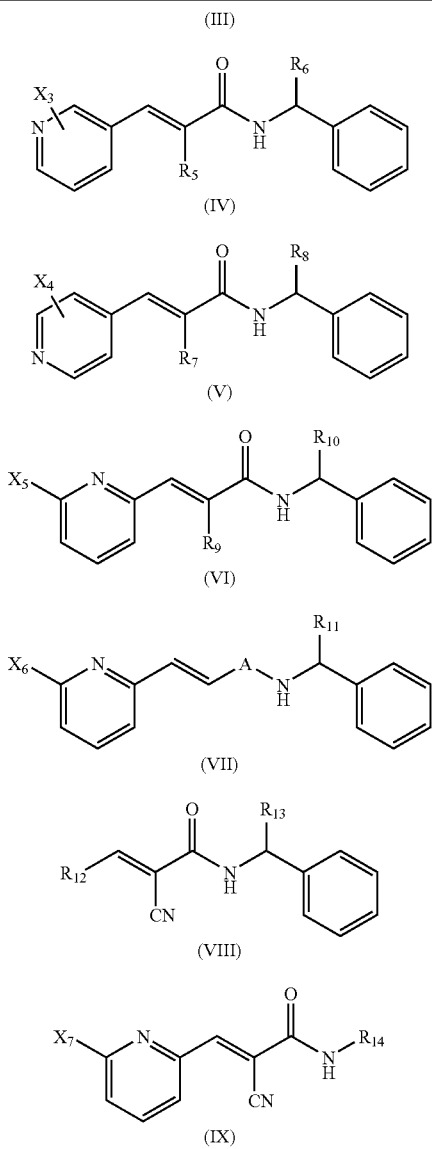

In certain aspects of the invention, the chemical structures shown in Table 1 may be defined as follows: $R_1$ is —H or cyano and $R_2$ is heteroatom-substituted or heteroatom-unsubstituted $C_3$-$C_7$-cycloalkyl; $X_1$ is halo and $R_3$ is heteroatom-substituted or heteroatom-unsubstituted $C_1$-$C_7$-cycloalkyl, $C_6$-$C_{10}$-aryl, or $C_7$-$C_{10}$-aralkyl; $X_2$ is halo and $R_4$ is hydroxy or heteroatom-substituted or heteroatom-unsubstituted $C_1$-$C_{10}$-acyloxy; $X_3$ is halo or heteroatom-substituted or heteroatom-unsubstituted $C_1$-$C_{10}$-alkyl or $C_1$-$C_{10}$-alkoxy; $R_5$ is —H or cyano, and $R_6$ is heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl; $X_4$ is halo or heteroatom-substituted or heteroatom-unsubstituted $C_1$-$C_{10}$-alkyl or $C_1$-$C_{10}$-alkoxy; $R_7$ is —H or cyano; $R_8$ is heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl; $X_5$ is heteroatom-substituted or heteroatom-unsubstituted $C_1$-$C_{10}$-alkyl or $C_1$-$C_{10}$-alkoxy; $R_9$ is —H or cyano; $R_{10}$ is heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl; A is —C(O)— or —S(O$_2$)—; $X_6$ is halo or heteroatom-substituted or heteroatom-unsubstituted $C_1$-$C_{10}$-alkyl or $C_1$-$C_{10}$-alkoxy; $R_{11}$ is heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl; $R_{12}$ is cyclododecyl, imidazoyl, or cyclohexenyl; $R_{13}$ is —H or heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl; $X_7$ is halo or heteroatom-substituted or heteroatom-unsubstituted $C_1$-$C_{10}$-alkyl or $C_1$-$C_{10}$-alkoxy; $R_{14}$ is:

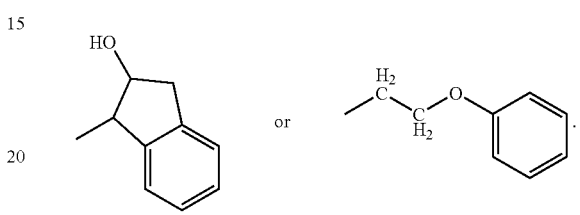

Other aspects of the invention include pharmaceutically acceptable salts, hydrates, amine-N-oxides, imine-N-oxides, tautomers, and optical isomers of the compounds described above and throughout this application.

In certain embodiments $R_2$ may cyclopropyl, cyclobutyl, cyclopentyl or cyclohexyl. In further embodiments $R_3$ may be phenyl, benzyl, cyclopropyl, cyclobutyl, cyclopentyl or cyclohexyl. In yet further embodiments, $X_1$ or $X_2$ may be —F, —Cl, —Br or —I. In still further embodiments, $R_4$ may be hydroxy, acetoxy or 2,2-dimethylpropionyloxy. In still yet further embodiments, $X_3$ or $X_4$ may be methoxy, —F, —Cl, —Br or —I. In some embodiments, $R_6$ or $R_8$ may be methyl or cyclopropyl. In certain aspects, $X_5$ may be methyl or acetoxymethyl.

The compounds shown in Table 2 are specific examples of compounds provided by this invention:

TABLE 2

Additional Examples of Caffeic Acid Analogs:

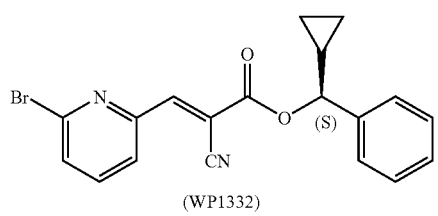

(WP1332)

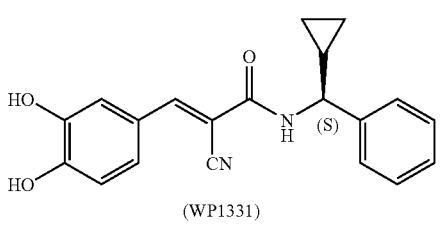

(WP1331)

TABLE 2-continued
Additional Examples of Caffeic Acid Analogs:
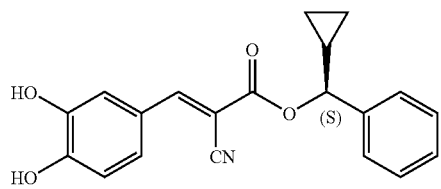
(WP1330)
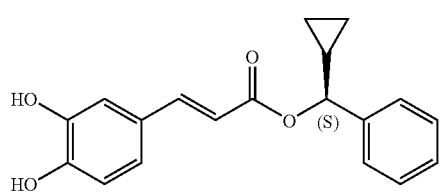
(WP1329)
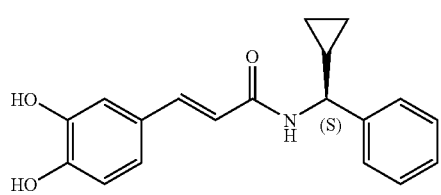
(WP1328)
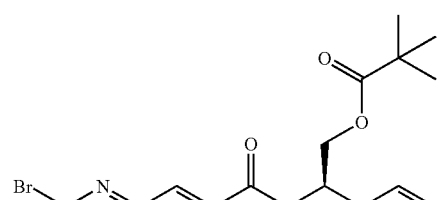
(WP1302)
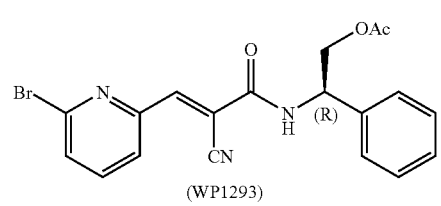
(WP1293)
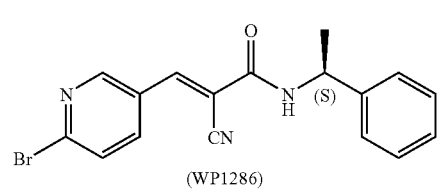
(WP1286)
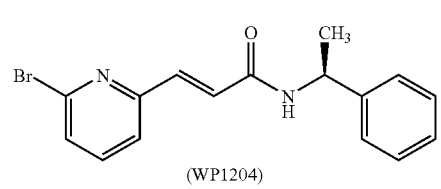
(WP1204)
TABLE 2-continued
Additional Examples of Caffeic Acid Analogs:
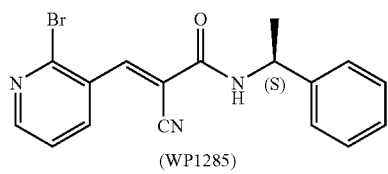
(WP1285)
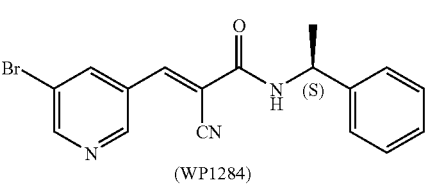
(WP1284)
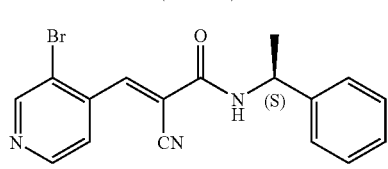
(WP1283)
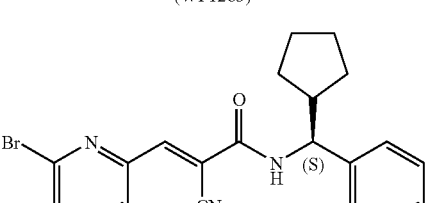
(WP1282)
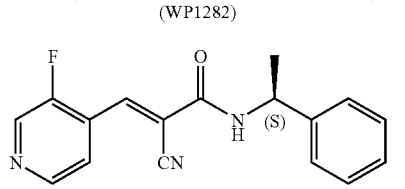
WP1280
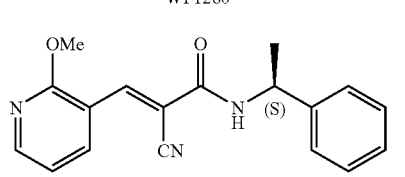
(WP1273)
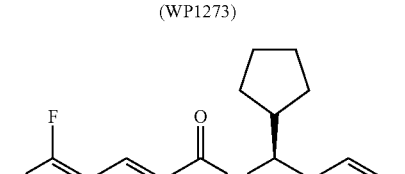
(WP1272)
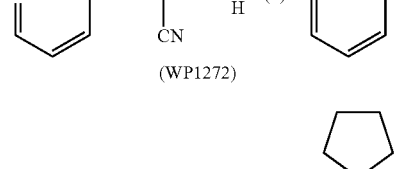
(WP1246)
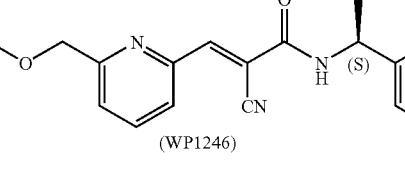

TABLE 2-continued

Additional Examples of Caffeic Acid Analogs:

(WP1229)

(WP1269)

(WP1271)

(WP1268)

(WP1267)

(WP1203)

(WP1201)

TABLE 2-continued

Additional Examples of Caffeic Acid Analogs:

(WP1196)

(WP1180)

(WP1179)

(WP1169).

(WP1168)

(WP1167)

(WP1166)

TABLE 2-continued

Additional Examples of Caffeic Acid Analogs:

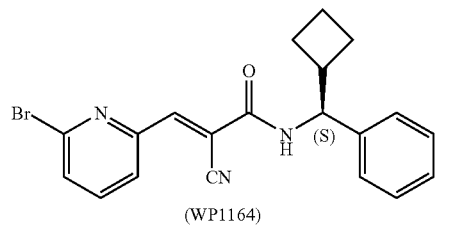
(WP1164)

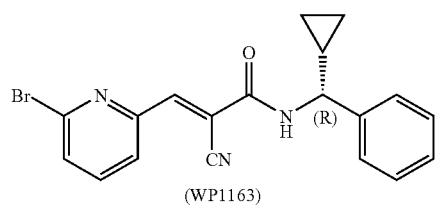
(WP1163)

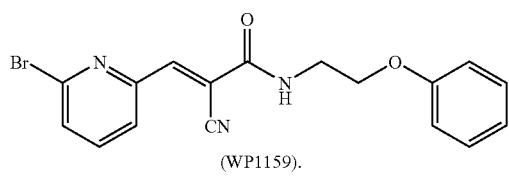
(WP1159).

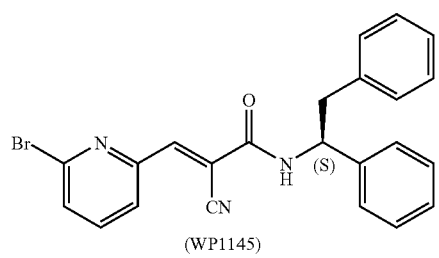
(WP1145)

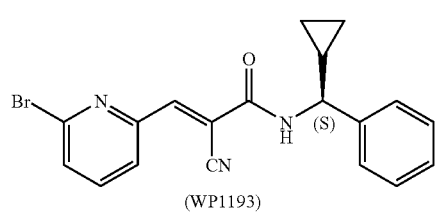
(WP1193)

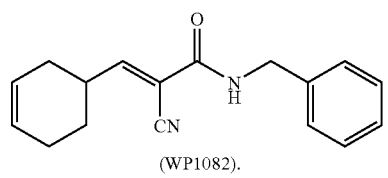
(WP1082).

Some of the compounds in Table 2 are shown as single enantiomers or diastereomers. The invention provides for all possible stereoisomers of any of the compounds shown in Table 2 above, as well as those described throughout the application. In some embodiments, the compound provided will be a single enantiomer substantially free from other stereoisomers. In other embodiments, the compound will be a mixture of different stereo isomers, wherein each stereo isomer has the same molecular formula. In certain of these embodiments, the invention provides for a racemic mixture of a given molecular formula.

Another aspect of the invention comprises compounds having the formula:

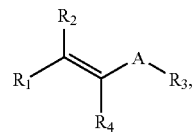

wherein A is —C(O)— or —SO$_2$—. In certain embodiments R$_1$ is cyclododecyl,

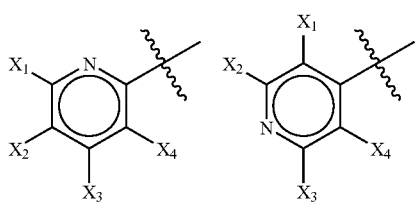

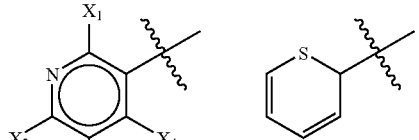

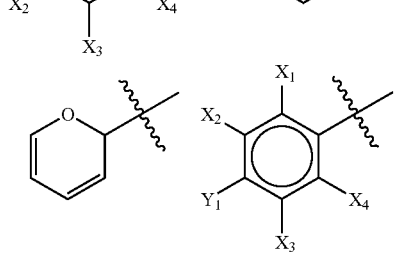

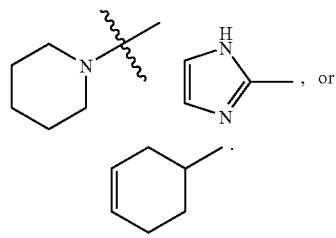

, or

In some of these embodiments, X$_1$, X$_2$, X$_3$, and X$_4$, are each independently hydrogen, halo, alkyl, alkoxyl, acetoxyl, alkylacetoxyl, —OH, trihalomethyl, or —NO$_2$; Y$_1$ is halo, —OH or —NO$_2$; and R$_2$ is selected from the group consisting of alkyl, alkenyl, alkynyl, alkoxy, alkylaryl, halo, hydrogen, —OH, —NO$_2$, thioether, amino, —SH, or —NH$_2$; R$_3$ is:

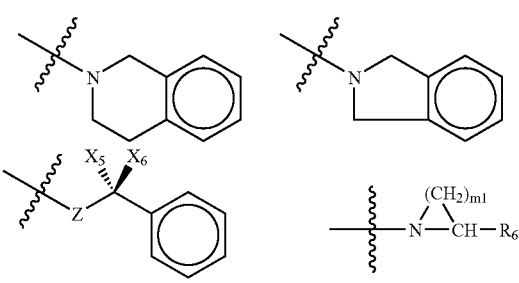

-continued

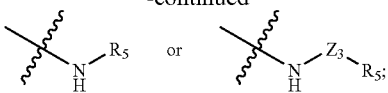

wherein $Z_3$ may be a divalent alkyl; and wherein $m_1$=1, 2, 3, or 4; and $R_4$ may be hydrogen, —CN, substituted amine, —CH$_2$S-alkyl, alkyl, or —CH$_2$N$_3$. In some of these embodiments, $R_5$ and $R_6$ are each independently:

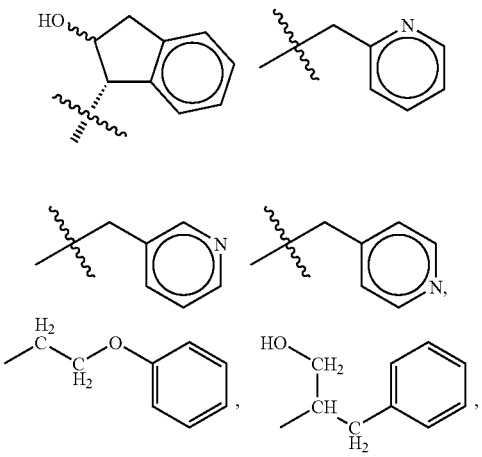

monosaccharide, monosaccharide derivative, polysaccharide, polysaccharide derivative, aryl or aralkyl; Z is selected from the group consisting of —NH, —S—, and —O—, and $X_5$ and $X_6$ are each independently selected from the group consisting of hydrogen, upper alkyl, lower alkyl, cycloalkyl, cycloarylalkyl, aralkyl, aryl, alkoxyl, hydroxyl, hydroxylalkyl, alkylester, alkylesteralkyl, alkylacetoxyl, or aryloxyl; with the proviso that if $R_4$=—CN, substituted amine, —CH$_2$S-alkyl, alkyl, or —CH$_2$N$_3$, then $R_1$ is selected from the group consisting of: cyclododecyl,

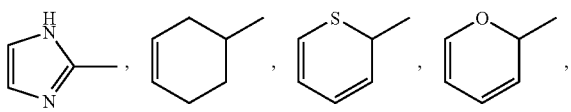

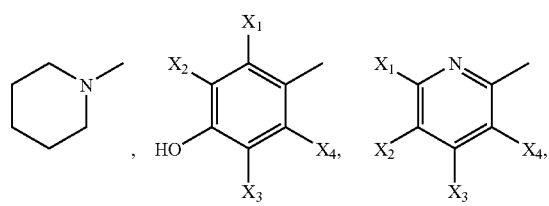

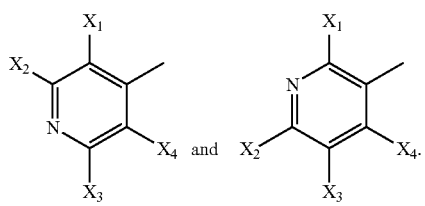

In further embodiments, $R_3$ is:

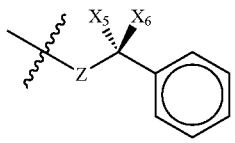

where $X_5$ or $X_6$ is upper alkyl, hydroxyl, aryl, alkoxyl, aryloxyl; cycloalkyl, cycloarylalkyl, aralkyl, alkylester, alkylesteralkyl, alkylacetoxy, or aryloxyl.

In specific embodiments, $Z_3$ may be —C$_2$H$_4$—. In some examples, $X_1$, $X_2$, $X_3$, and $X_4$, are each independently —F, —Cl, —Br, —CH$_3$, methoxy or alkylacetoxyl. In further embodiments, $X_5$ or $X_6$ is independently hydrogen, cyclopropyl, cyclobutyl, —CH$_3$, —CH$_2$OH, cyclopentyl, —CH$_2$OAc, —CH$_2$OC(O)C(CH$_3$)$_3$, —CH$_2$C$_6$H$_5$, cyclohexyl or aryl.

In other embodiments, $R_5$ is an aralkyl having the structure:

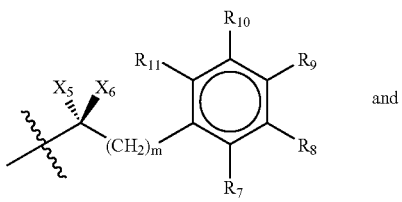

and an aryl having the structure:

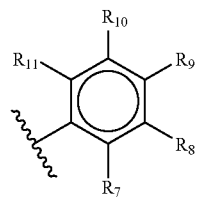

wherein m=0, 1, 2, 3, 4, 5, 6, or 7 and where $X_5$ and $X_6$ are each independently selected from the group consisting of hydrogen and alkyl, and where $R_7$, $R_8$, $R_9$, $R_{10}$, and $R_{11}$ are each independently selected from the group consisting of hydrogen, halo, alkyl, alkoxy, —OH, trihalomethyl, and —NO$_2$.

A method of treating a cell proliferative disease comprising administering to a subject an amount of a first compound effective to treat the cell proliferative disease, wherein the first compound is caffeic acid, the benzyl ester of caffeic acid, or one of the compounds the present invention, such as a compound according to Table 1 or a compound shown in Table 2.

Another aspect of the present invention concerns a method of treating a cell proliferative disease comprising administering a therapeutically relevant amount of a first compound of the present invention to a subject. The subject may be a mammal, and the mammal may be a human. The first compound may be comprised in a pharmaceutically acceptable excipient, diluent, or vehicle. The cell proliferative disease may be cancer. The cancer may be melanoma, non-small cell lung, small cell lung, lung, hepatocarcinoma, retinoblastoma, astrocytoma, glioblastoma, leukemia, blood, brain, skin, eye, tongue, gum, neuroblastoma, head, neck, breast, pancreatic, renal, bone, testicular, ovarian, mesothelioma, cervical, gastrointestinal, lymphoma, colon, or bladder.

The cell proliferative disease may be rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis and the variant forms of psoriasis including psoriatic arthritis other skin inflammatory conditions such as urticaria, excema, atopic dermatitis, granuloma annulare, angiomas, basal cell carcinoma, squamous cell carcinoma, malignant melanoma, seborrheic dermatitis, rosacea other hyperactive autoimmune disorders such as rheumatoid arthritis, chronic active hepatitis, Hashimoto's thyroiditis, lupus, connective tissue disorders, mixed connective tissue disorders, and neurologic inflammatory diseases such as multiple sclerosis, inflammatory leukoencephalitis.

In certain embodiments, STAT3 activation is reduced in a cell of the subject. The expression of c-myc may be reduced in a cell of the subject. The first compound may be administered in combination with a therapeutically relevant amount of a second compound. The second compound may be an anti-cancer compound. The first compound may be administered in combination with a surgery, a radiation therapy, or a gene therapy.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

As used herein, predominantly one enantiomer or substantially free from other optical isomers means that the compound contains at least 95% of one enantiomer, or more preferably at least 98% of one enantiomer, or most preferably at least 99% of one enantiomer.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
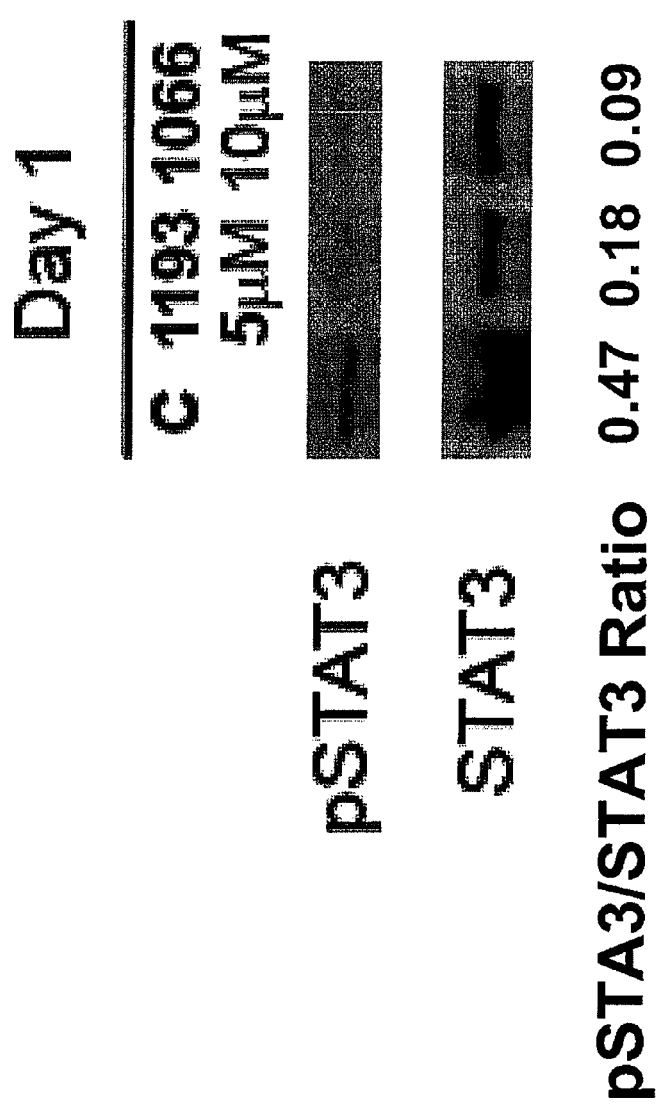
FIG. 1: Inhibition of constitutively activated STAT3 in Colo357-FG cells with WP1066 and WP1193. Western blots of phosphorylated STAT3 at Tyr705 and total STAT3.
Figure 2:
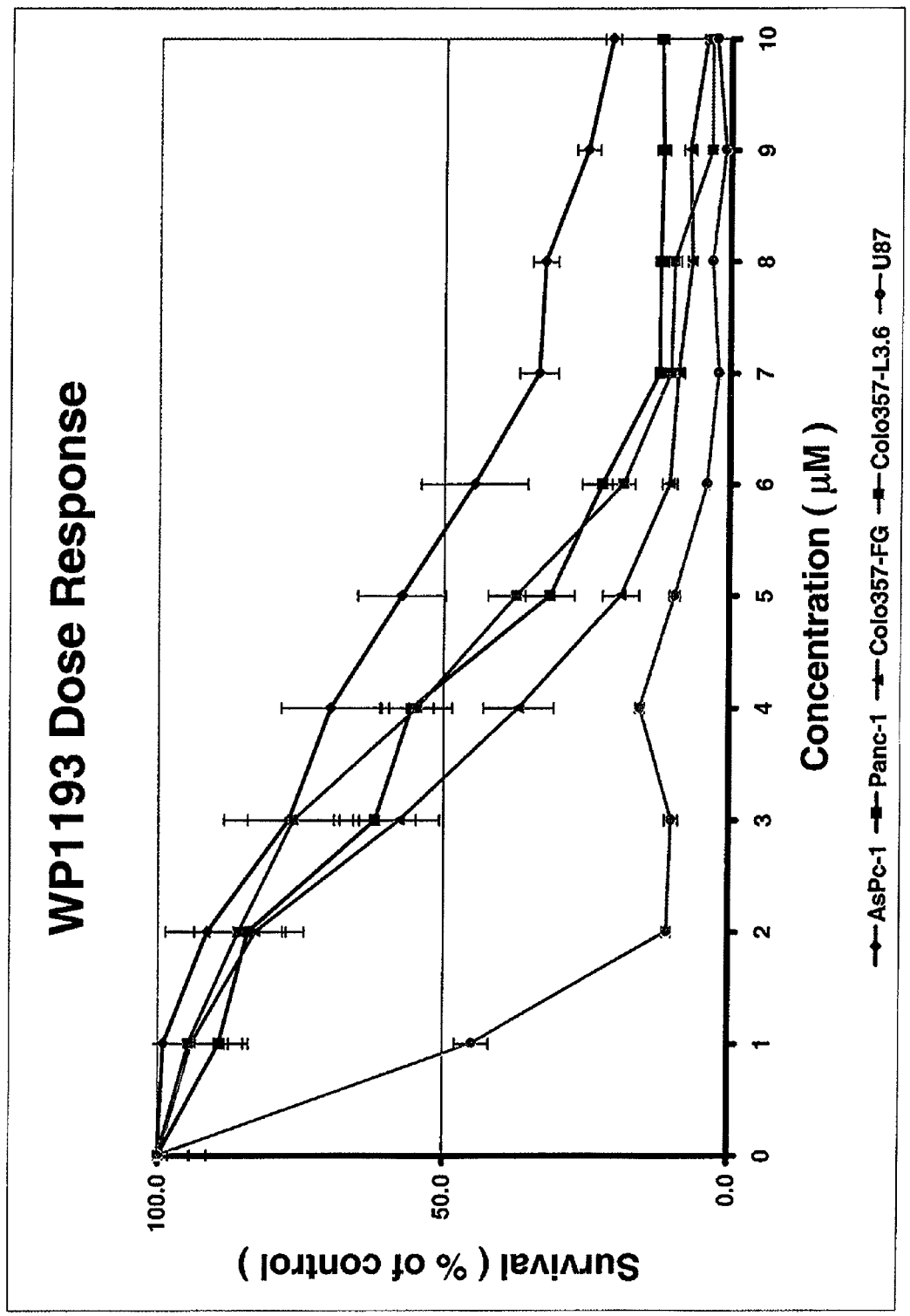
FIG. 2: Dose-response curve for WP1193 in the presence of various cell lines. Values are the means±s.d. (error bars) of triplicate experiments.
Figure 3:
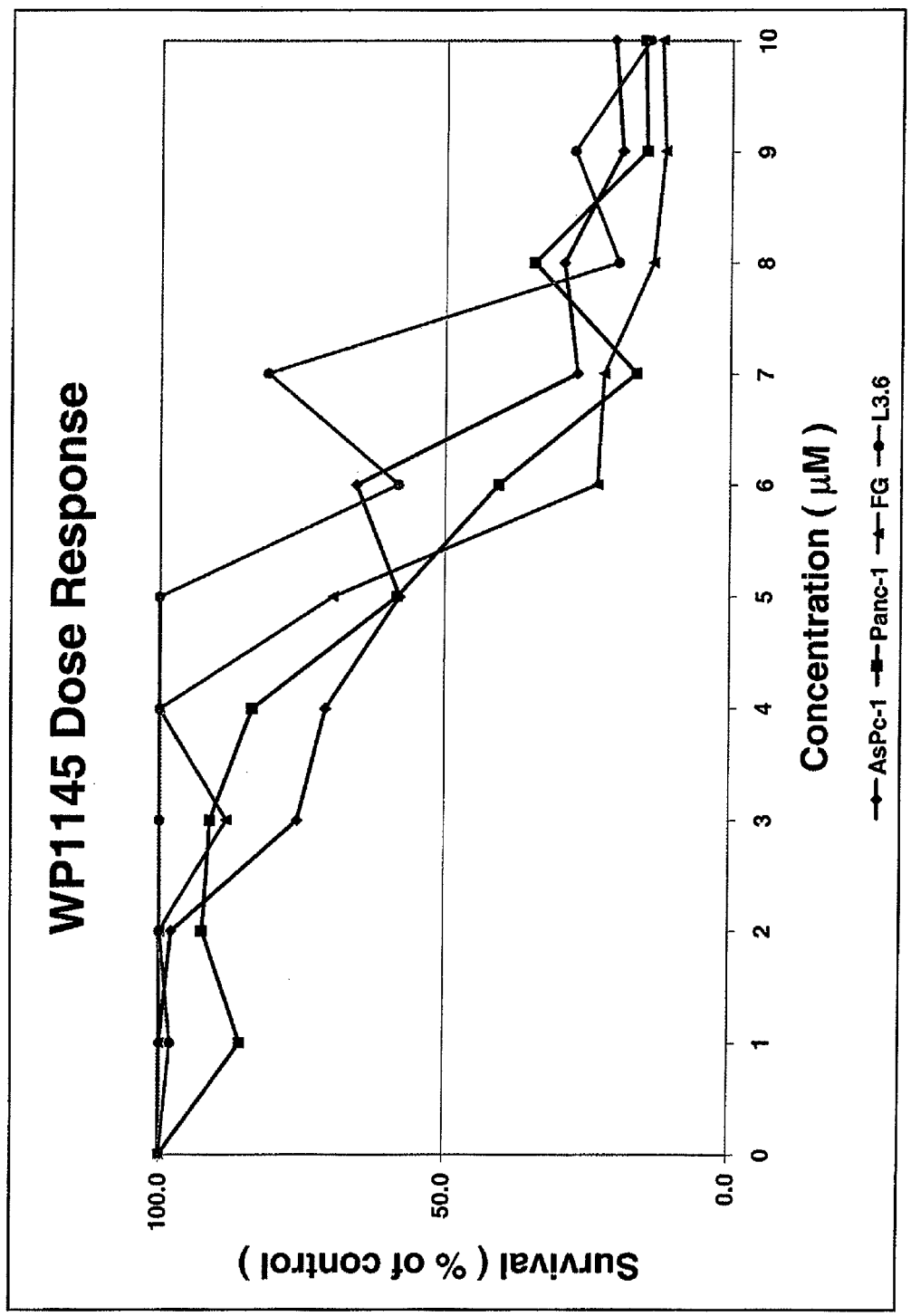
FIG. 3: Dose-response curve for WP1145 in the presence of various cell lines.
Figure 4:
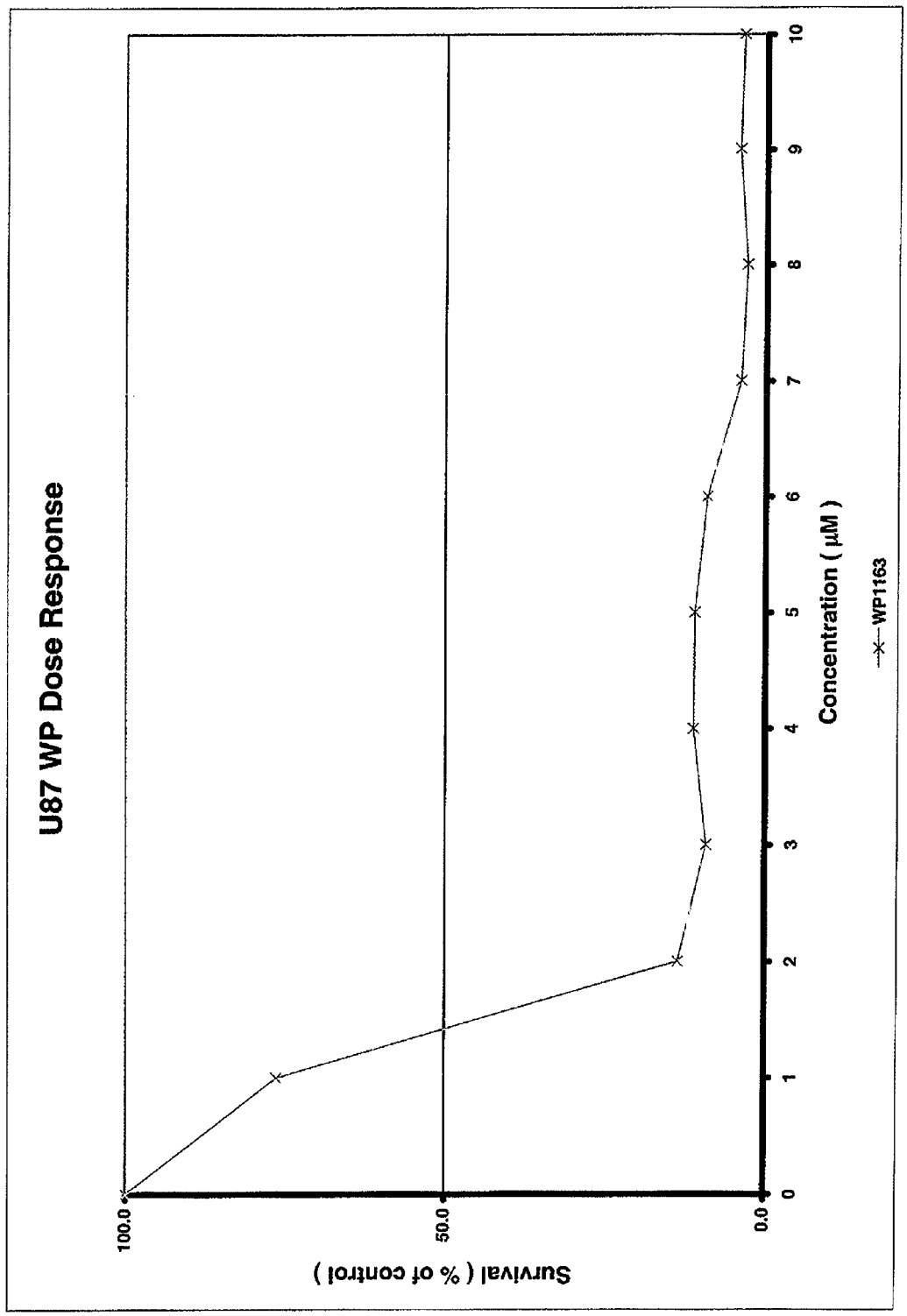
FIG. 4: Dose-response curve for WP1163 in the presence of the U87 cell line.
Figure 5:
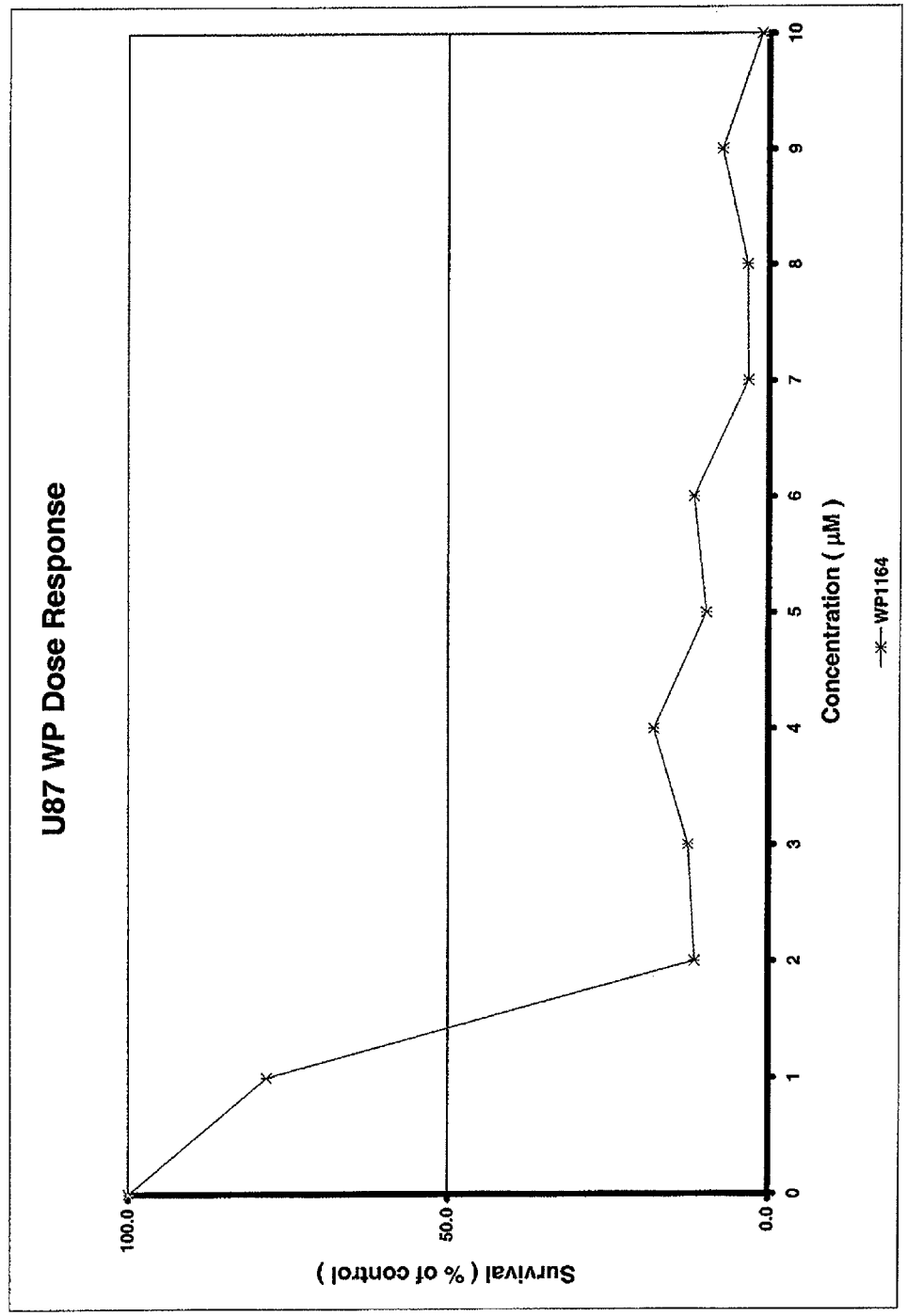
FIG. 5: Dose-response curve for WP1164 in the presence of the U87 cell line.
Figure 6:
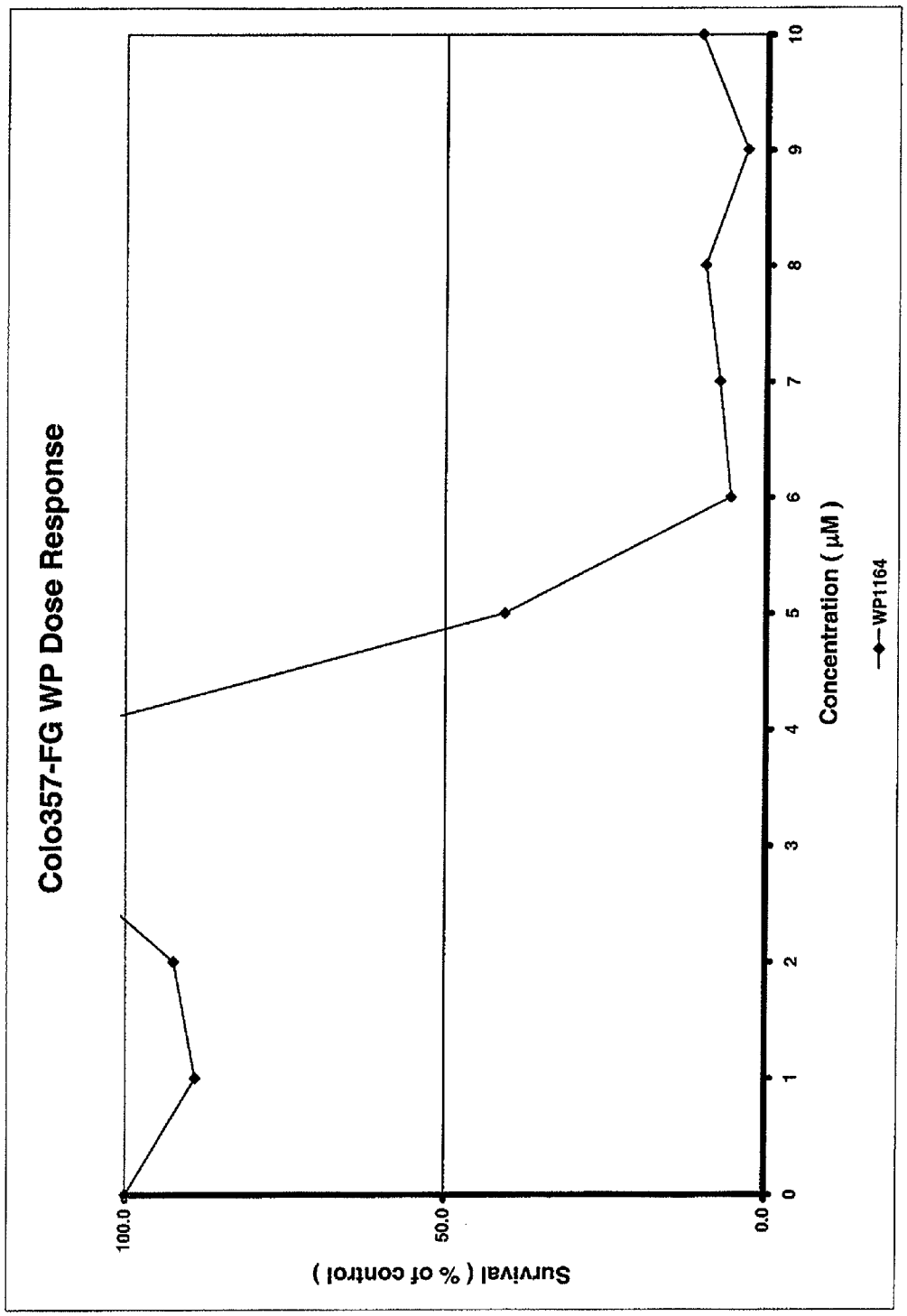
FIG. 6: Dose-response curve for WP1164 in the presence of the Colo357-FG cell line.
Figure 7:
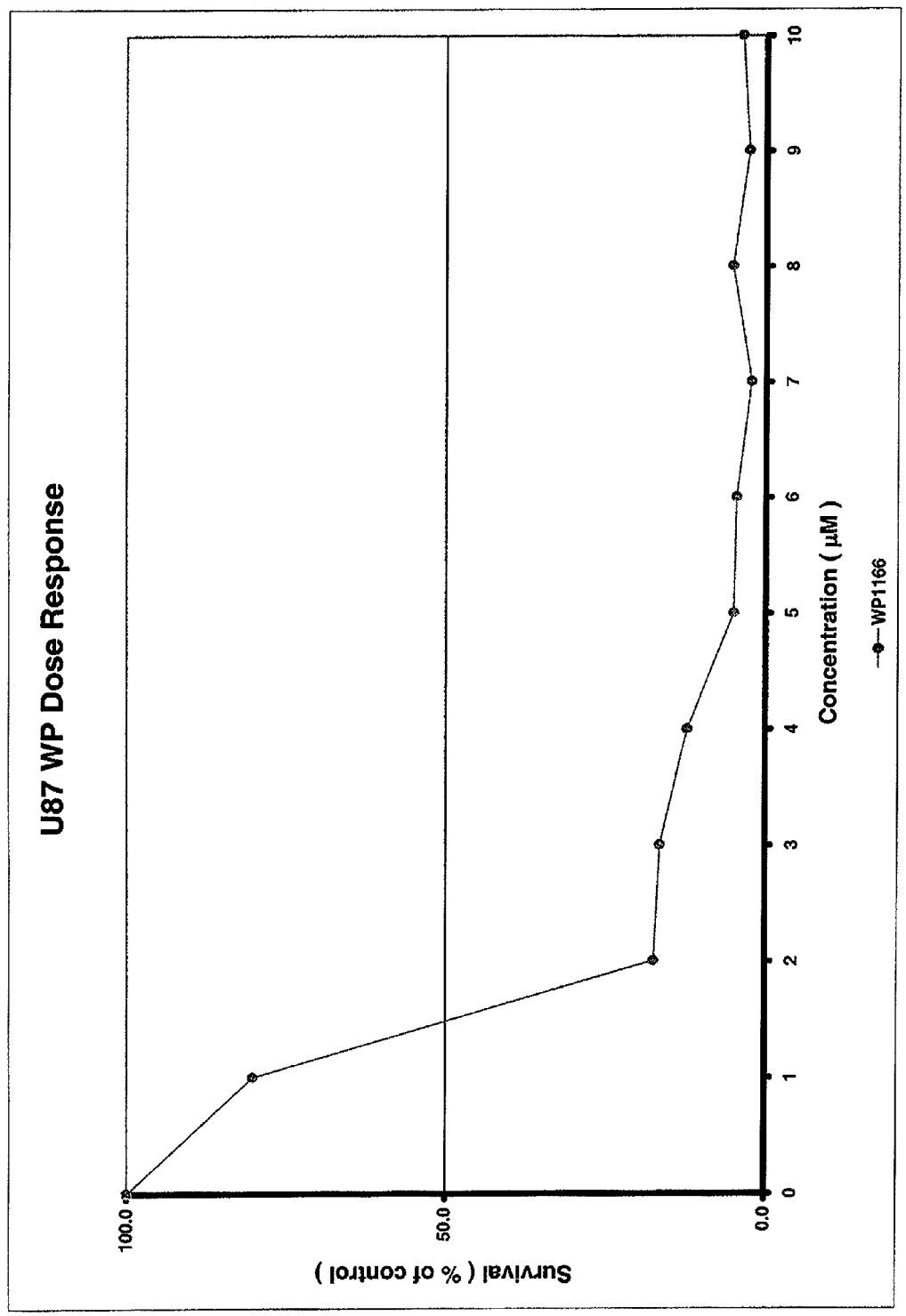
FIG. 7: Dose-response curve for WP1166 in the presence of the U87 cell line.
Figure 8:
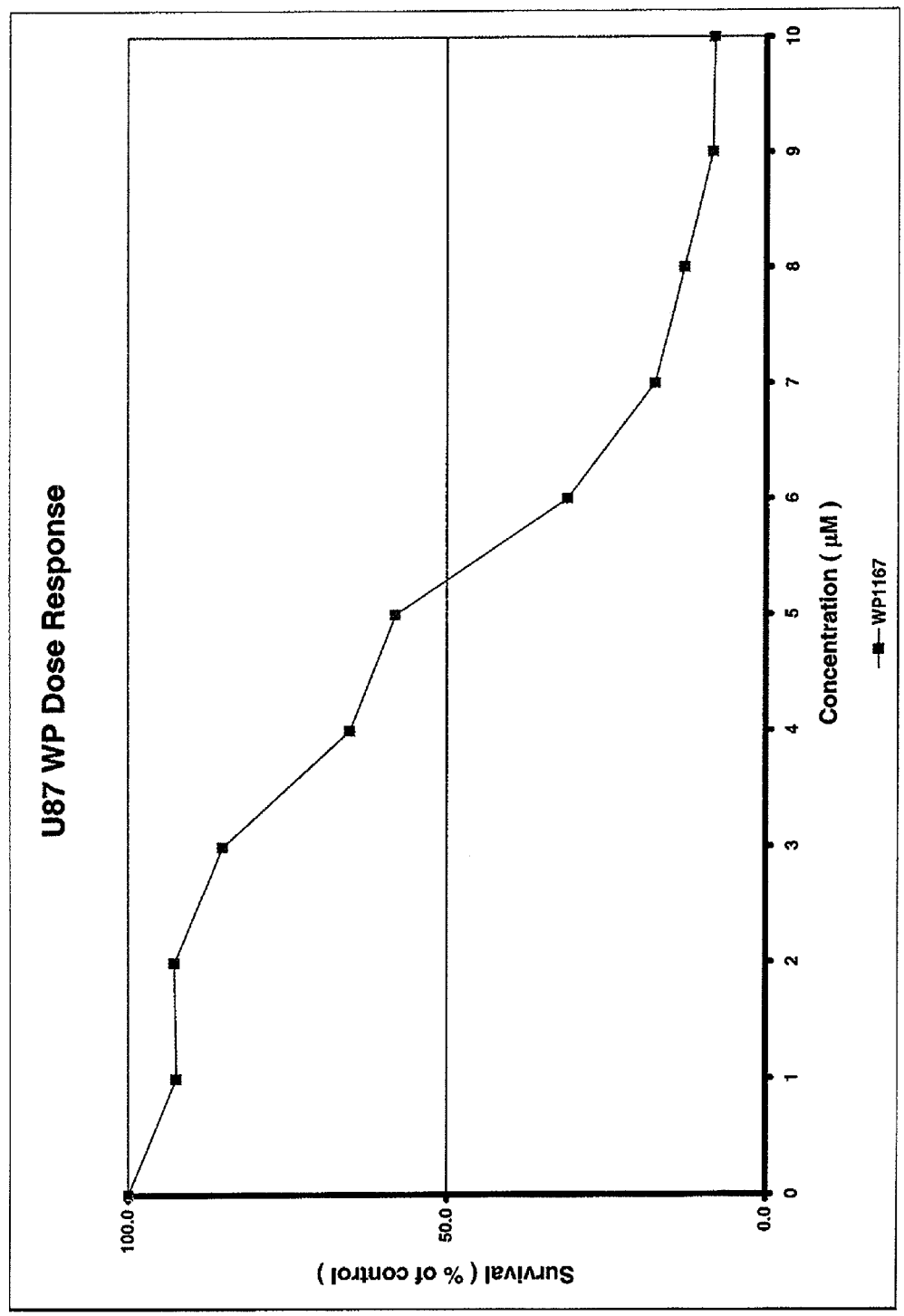
FIG. 8: Dose-response curve for WP1167 in the presence of the U87 cell line.
Figure 9:
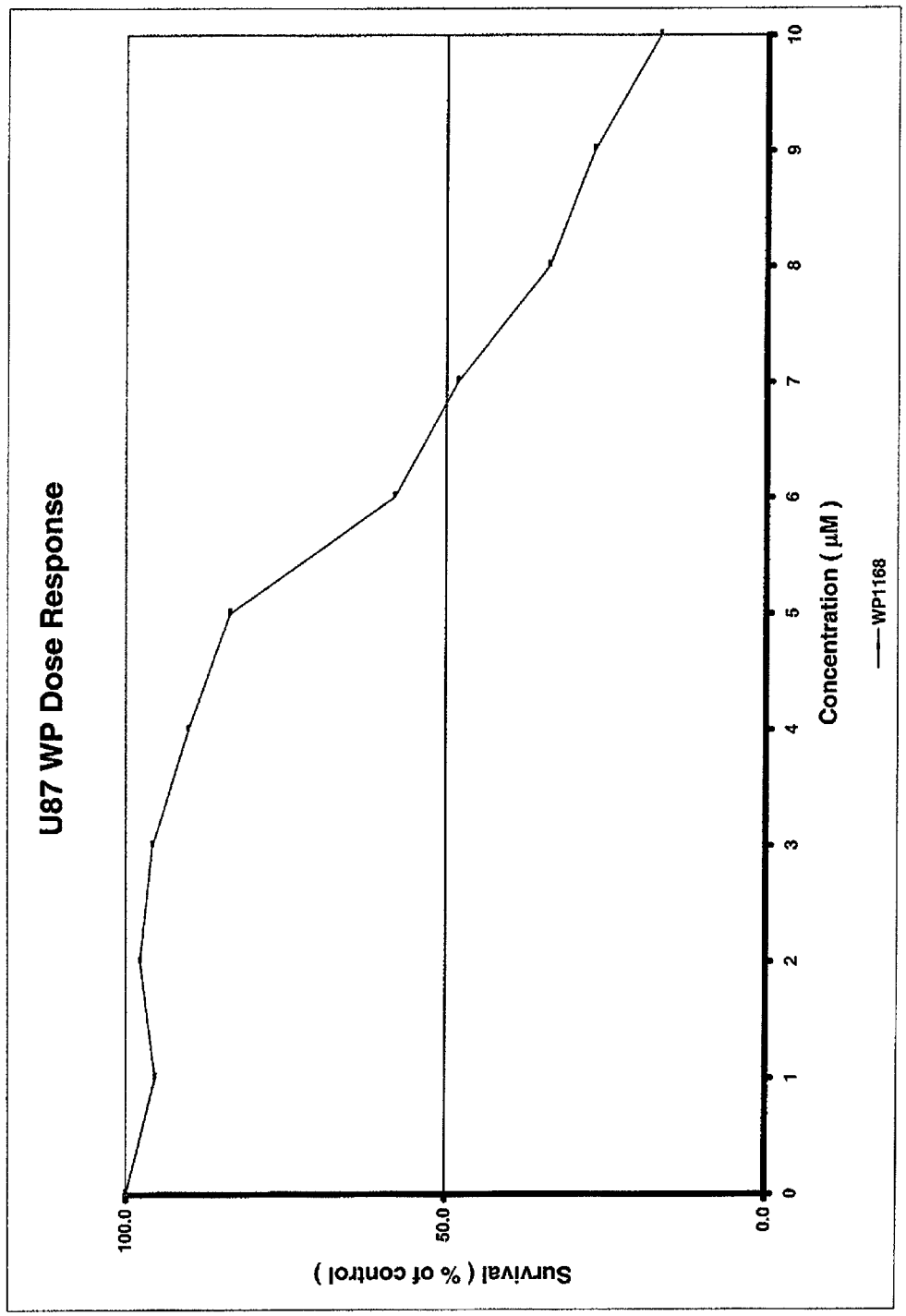
FIG. 9: Dose-response curve for WP1168 in the presence of the U87 cell line.
Figure 10:
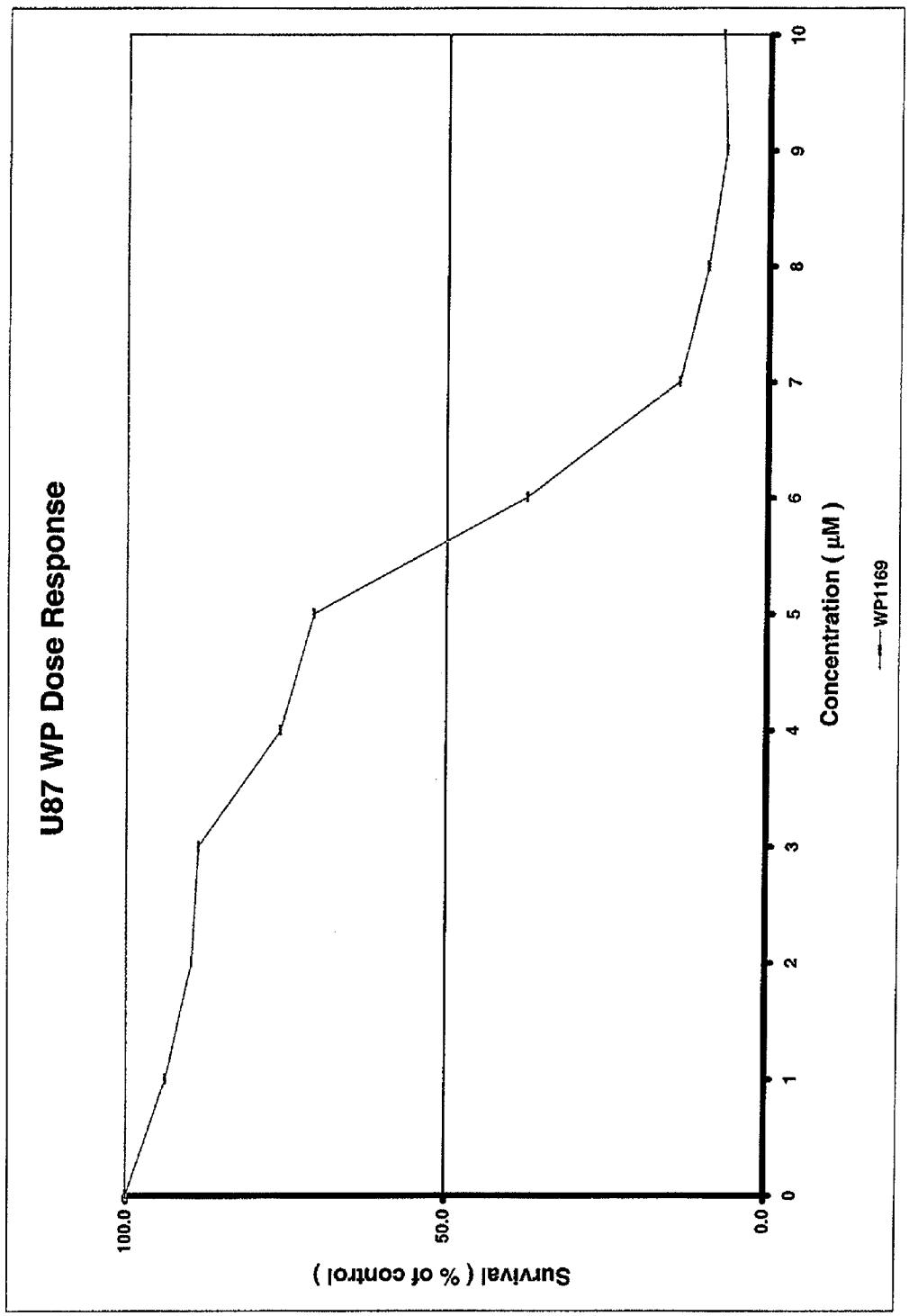
FIG. 10: Dose-response curve for WP1169 in the presence of the U87 cell line.
Figure 11:
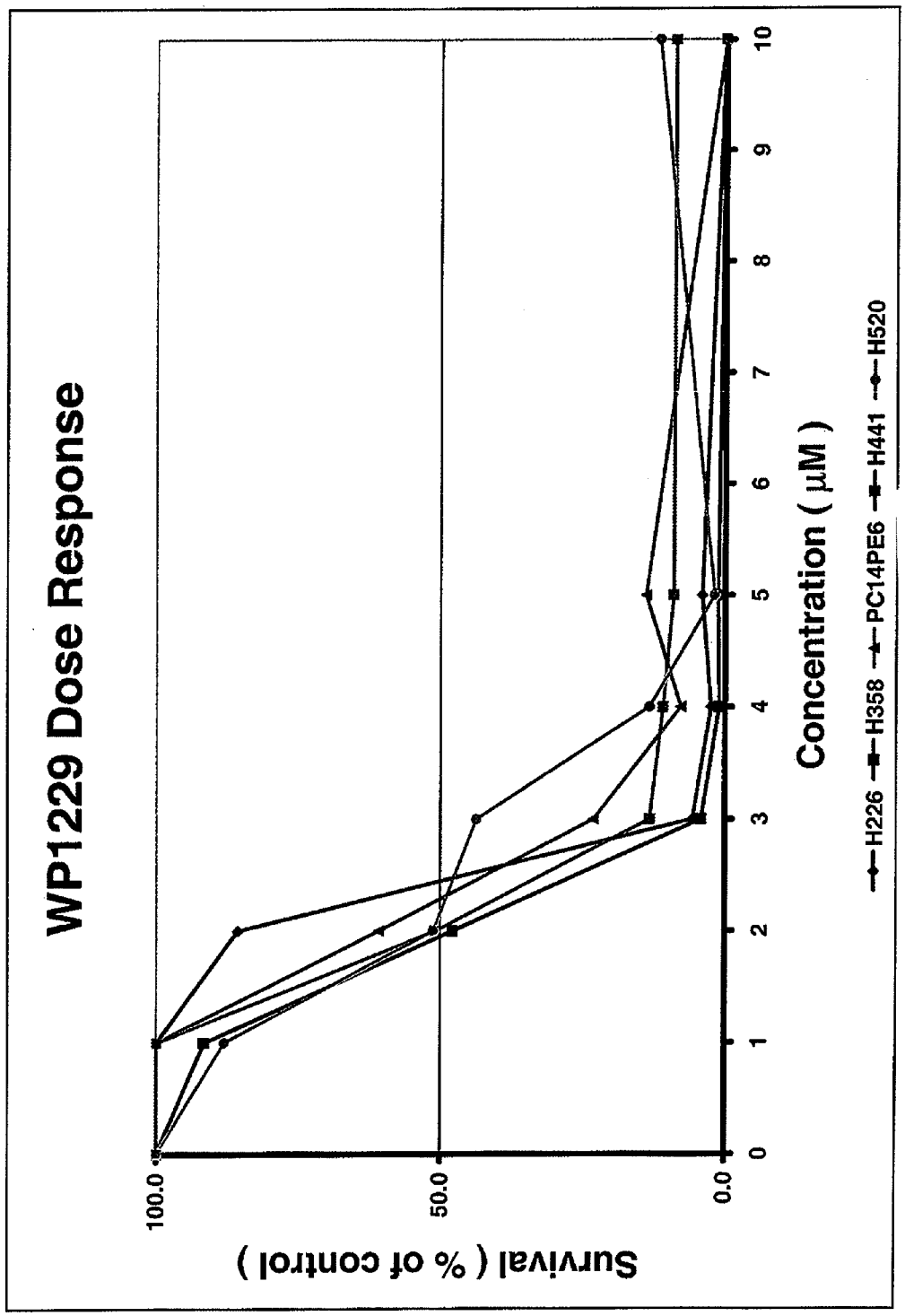
FIG. 11: Dose-response curve for WP1229 in the presence of the U87 and FG cell lines.
Figure 12:
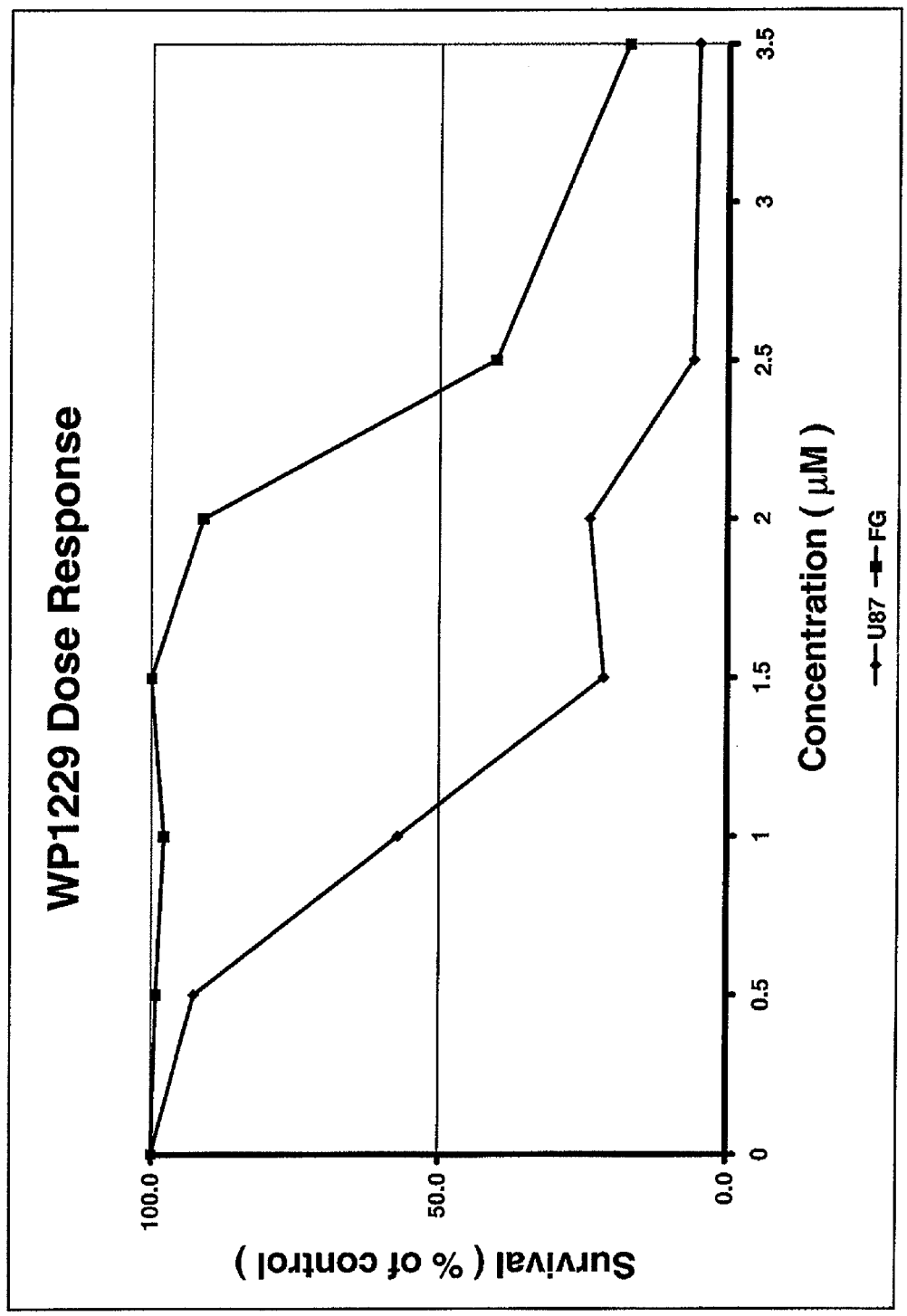
FIG. 12: Dose-response curve for WP1229 in the presence of the U87 cell line.
Figure 13:
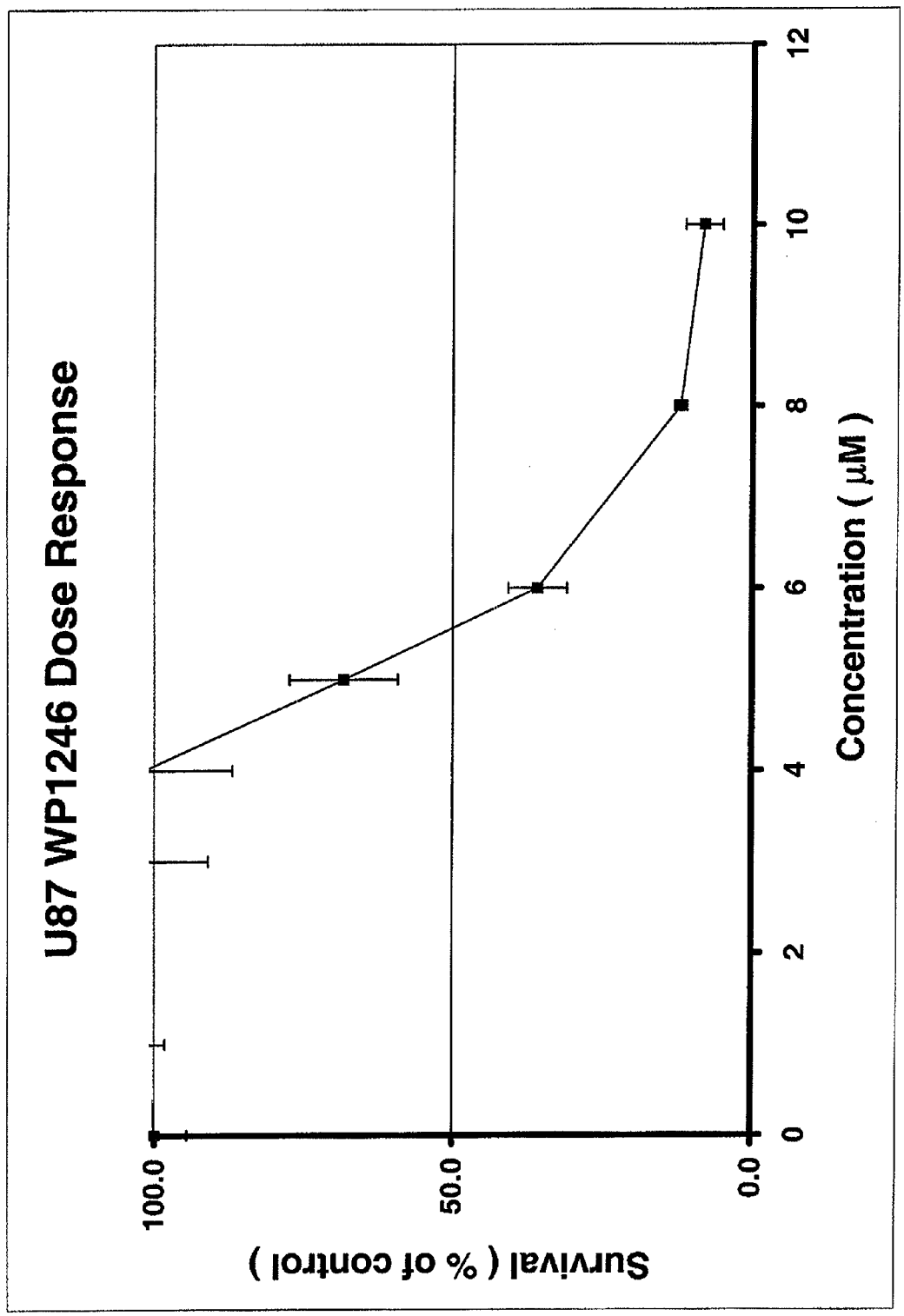
FIG. 13: Dose-response curve for WP1146 in the presence of the U87 cell line. Values are the means±s.d. (error bars) of triplicate experiments.
Figure 14:
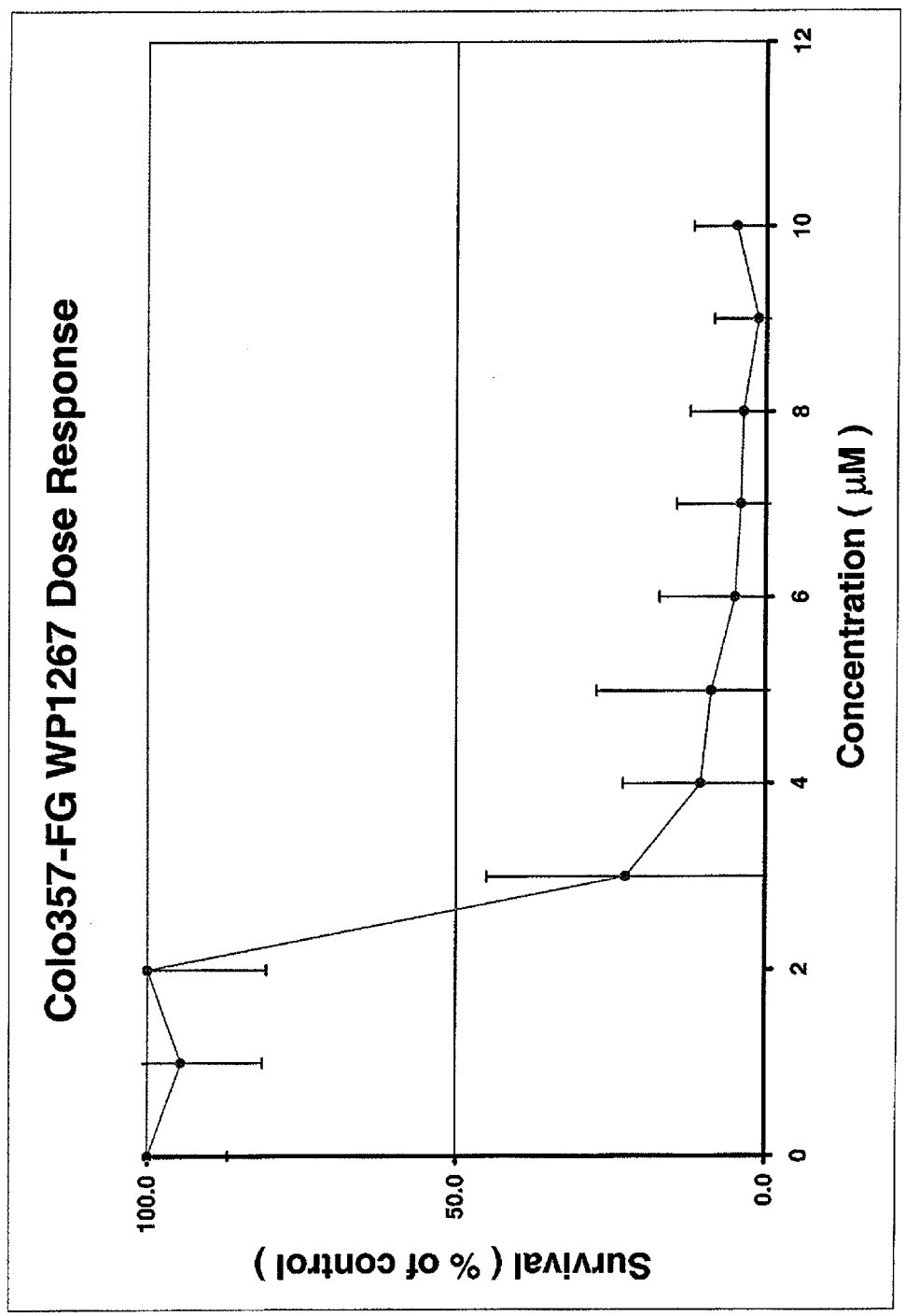
FIG. 14: Dose-response curve for WP1267 in the presence of the Colo357-FG cell line. Values are the means±s.d. (error bars) of triplicate experiments.
Figure 15:
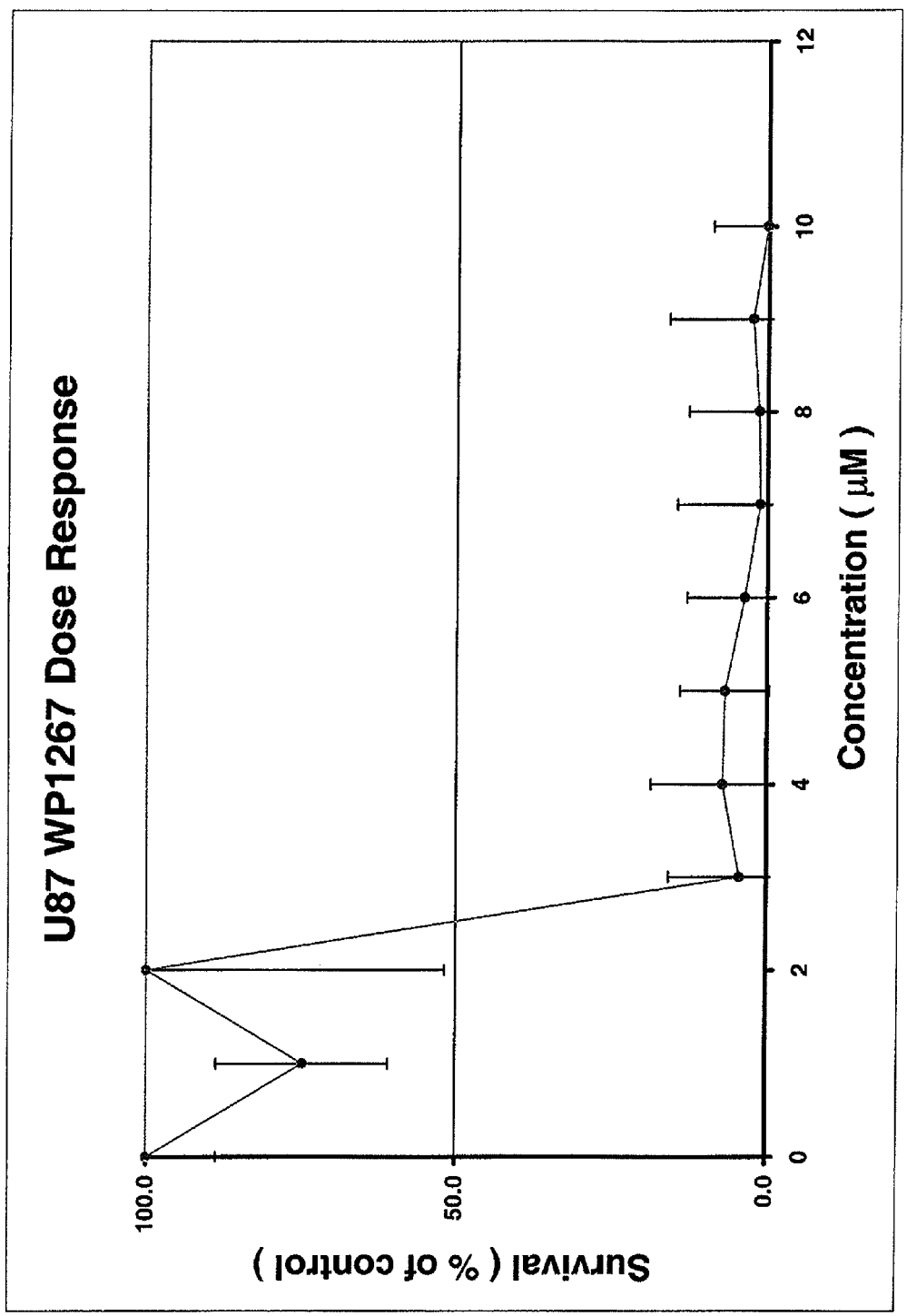
FIG. 15: Dose-response curve for WP1267 in the presence of the U87 cell line. Values are the means±s.d. (error bars) of triplicate experiments.
Figure 16:
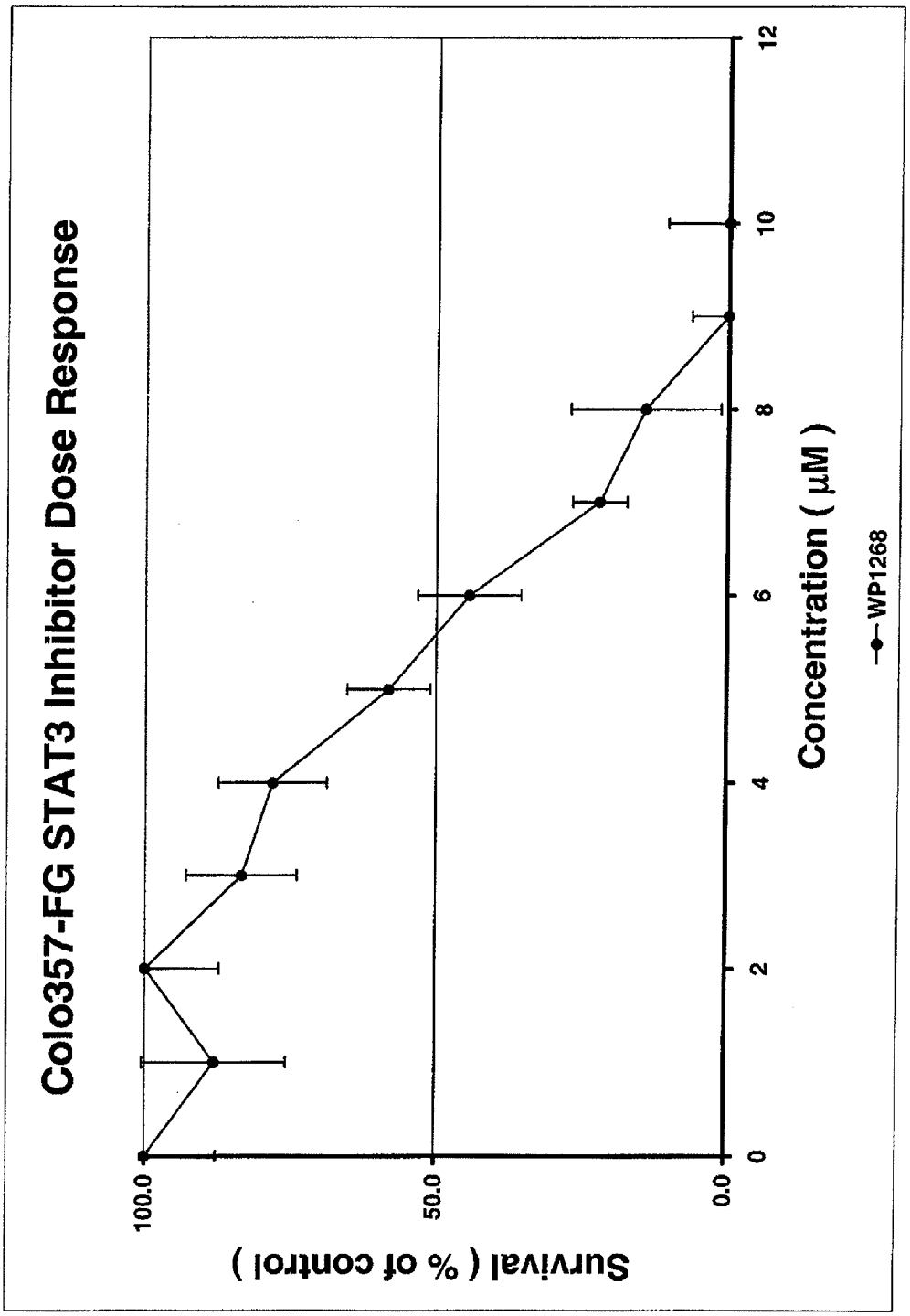
FIG. 16: Dose-response curve for WP1268 in the presence of the Colo357-FG cell line. Values are the means±s.d. (error bars) of triplicate experiments.
Figure 17:
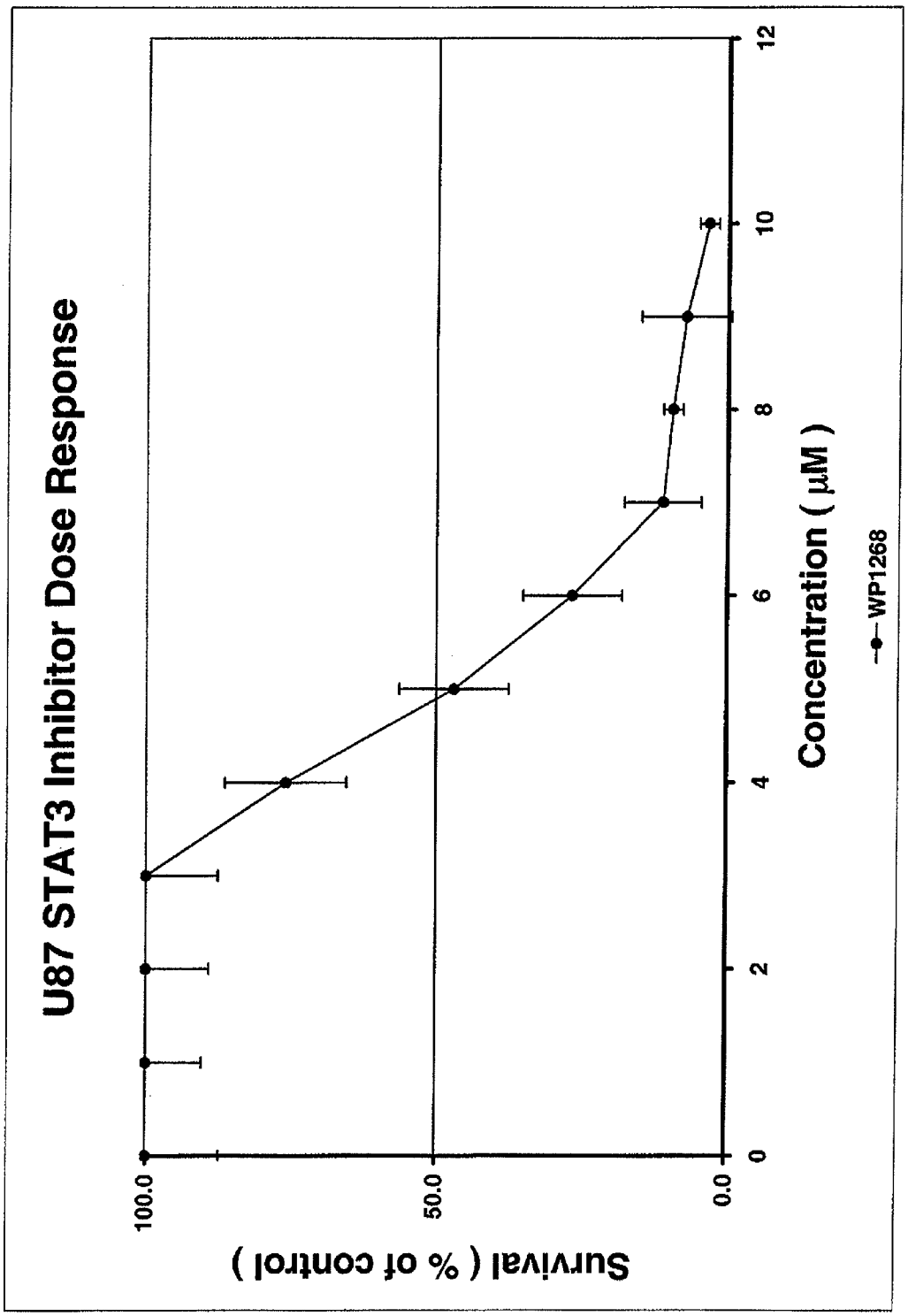
FIG. 17: Dose-response curve for WP1268 in the presence of the U87 cell line. Values are the means±s.d. (error bars) of triplicate experiments.
Figure 18:
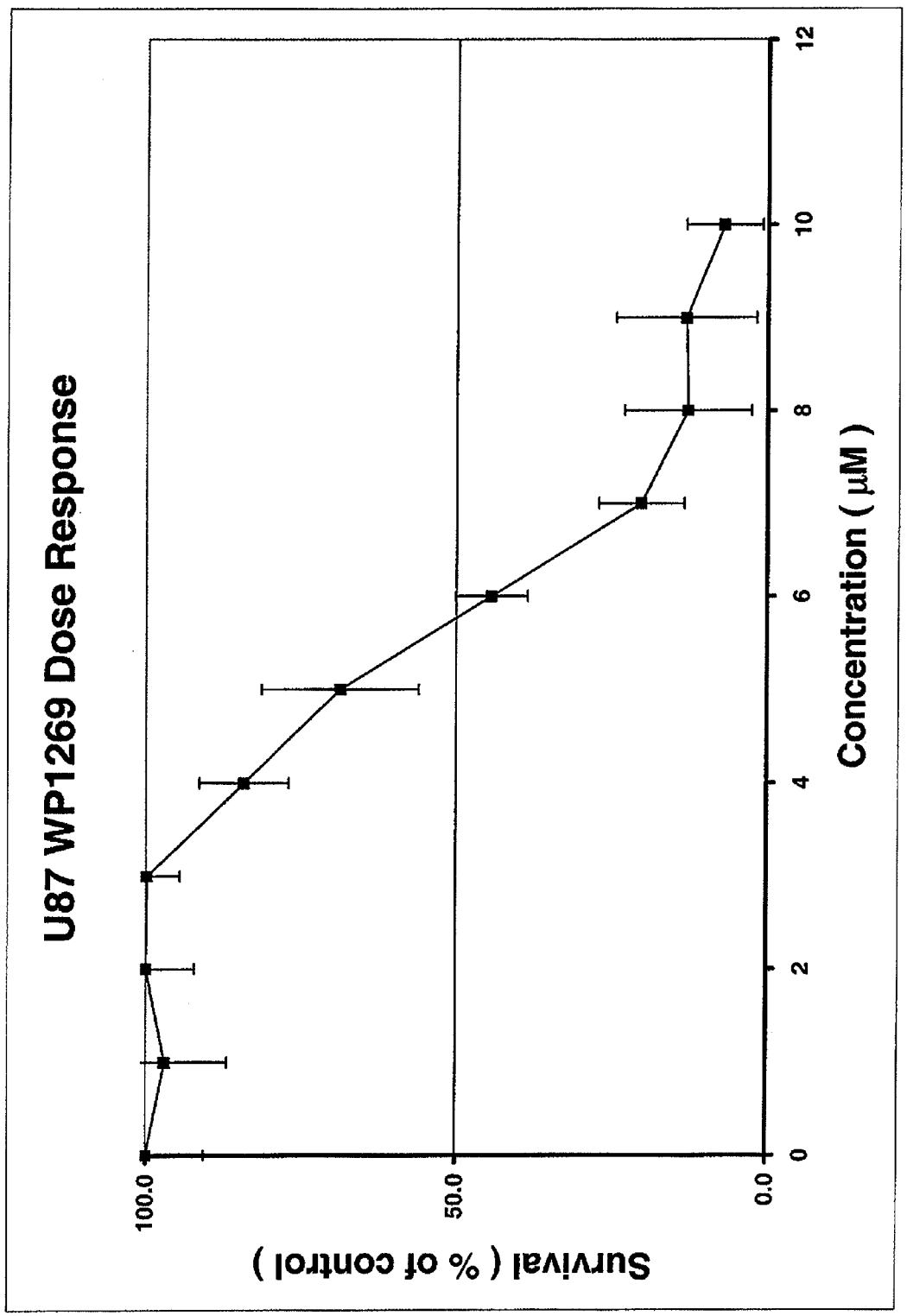
FIG. 18: Dose-response curve for WP1269 in the presence of the U87 cell line. Values are the means±s.d. (error bars) of triplicate experiments.
Figure 19:
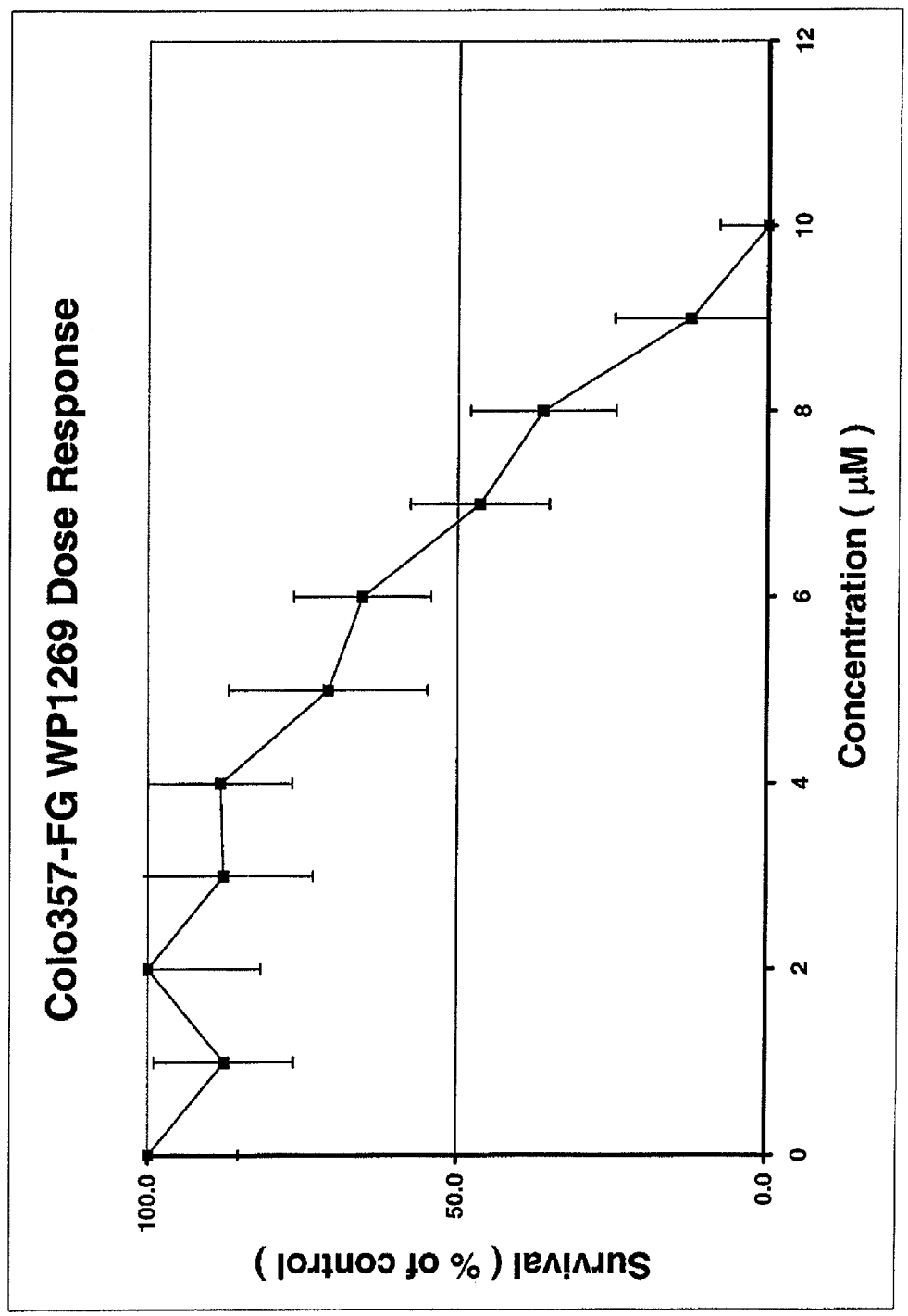
FIG. 19: Dose-response curve for WP1269 in the presence of the Colo357-FG cell line. Values are the means±s.d. (error bars) of triplicate experiments.
Figure 20:
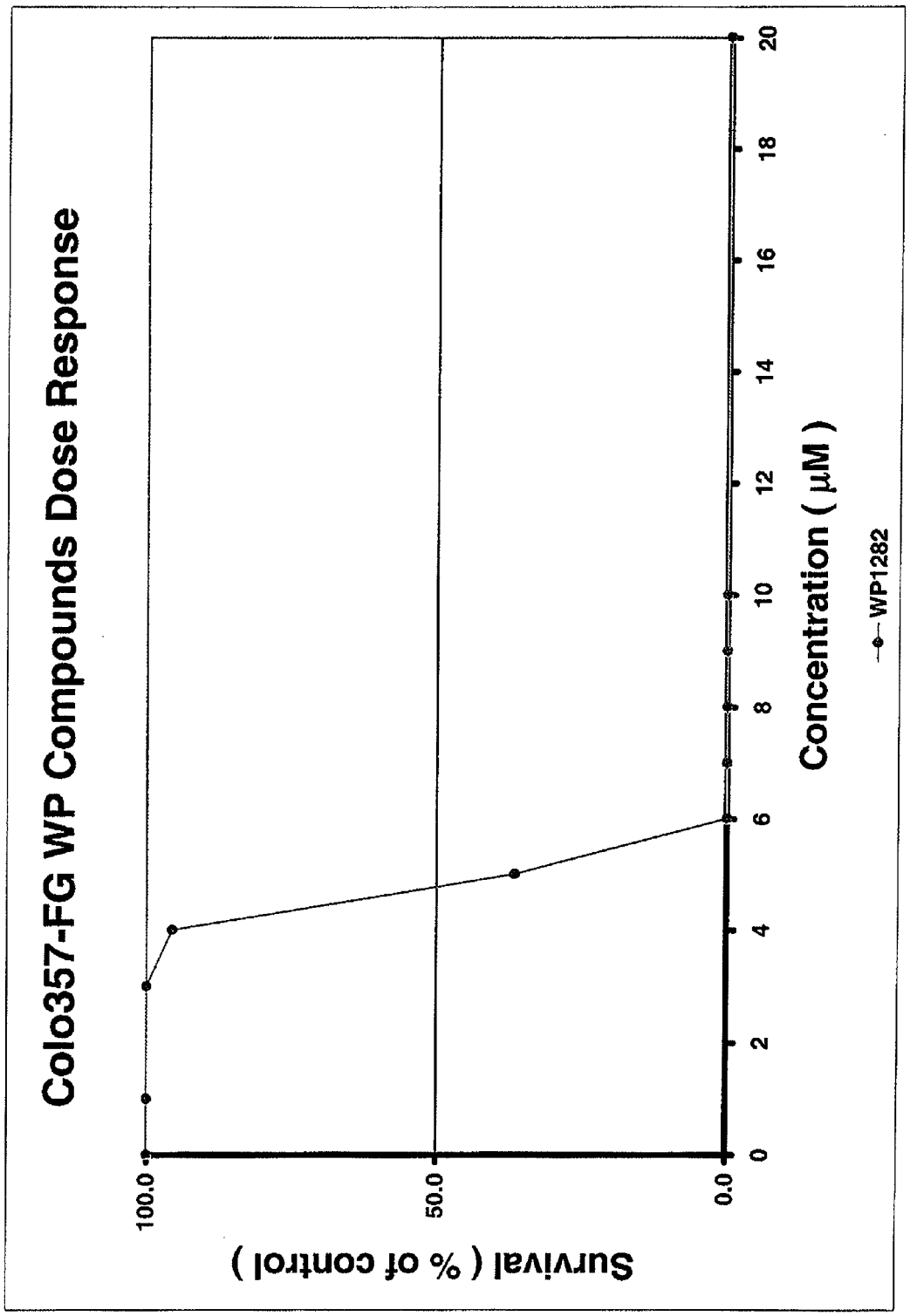
FIG. 20: Dose-response curve for WP1282 in the presence of the Colo357-FG cell line.
Figure 21:
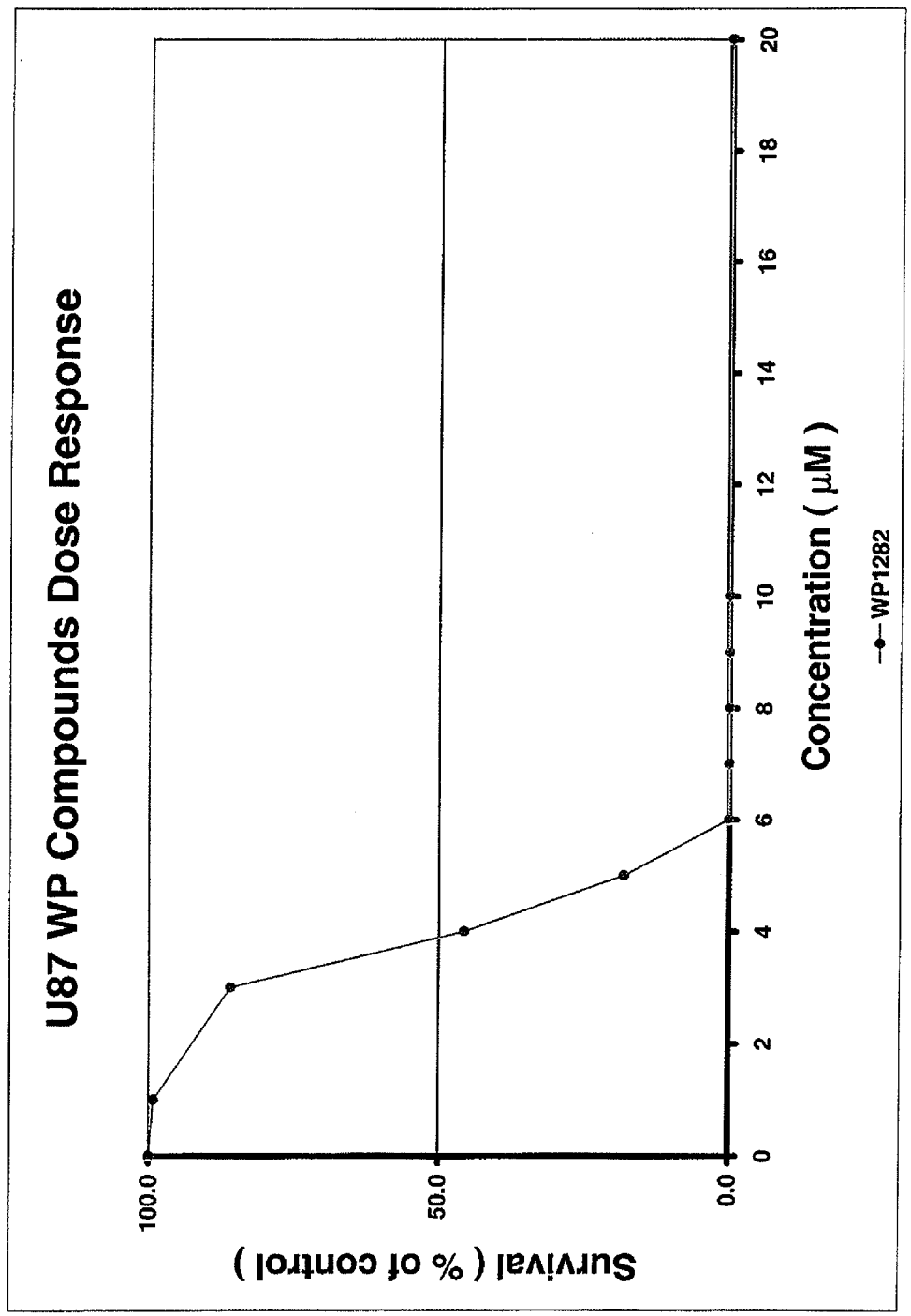
FIG. 21: Dose-response curve for WP1282 in the presence of the U87 cell line.
Figure 22:
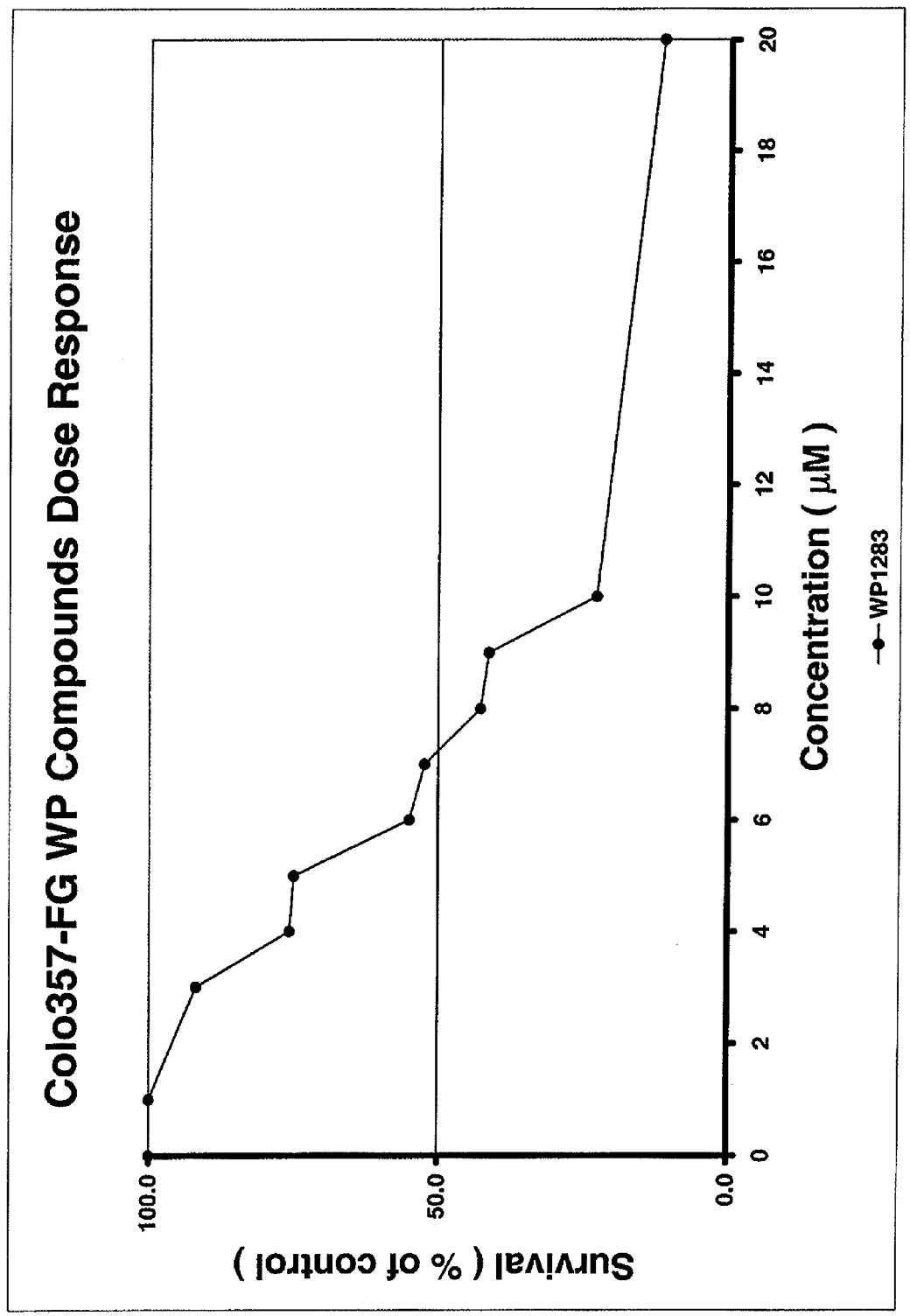
FIG. 22: Dose-response curve for WP1283 in the presence of the Colo357-FG cell line.
Figure 23:
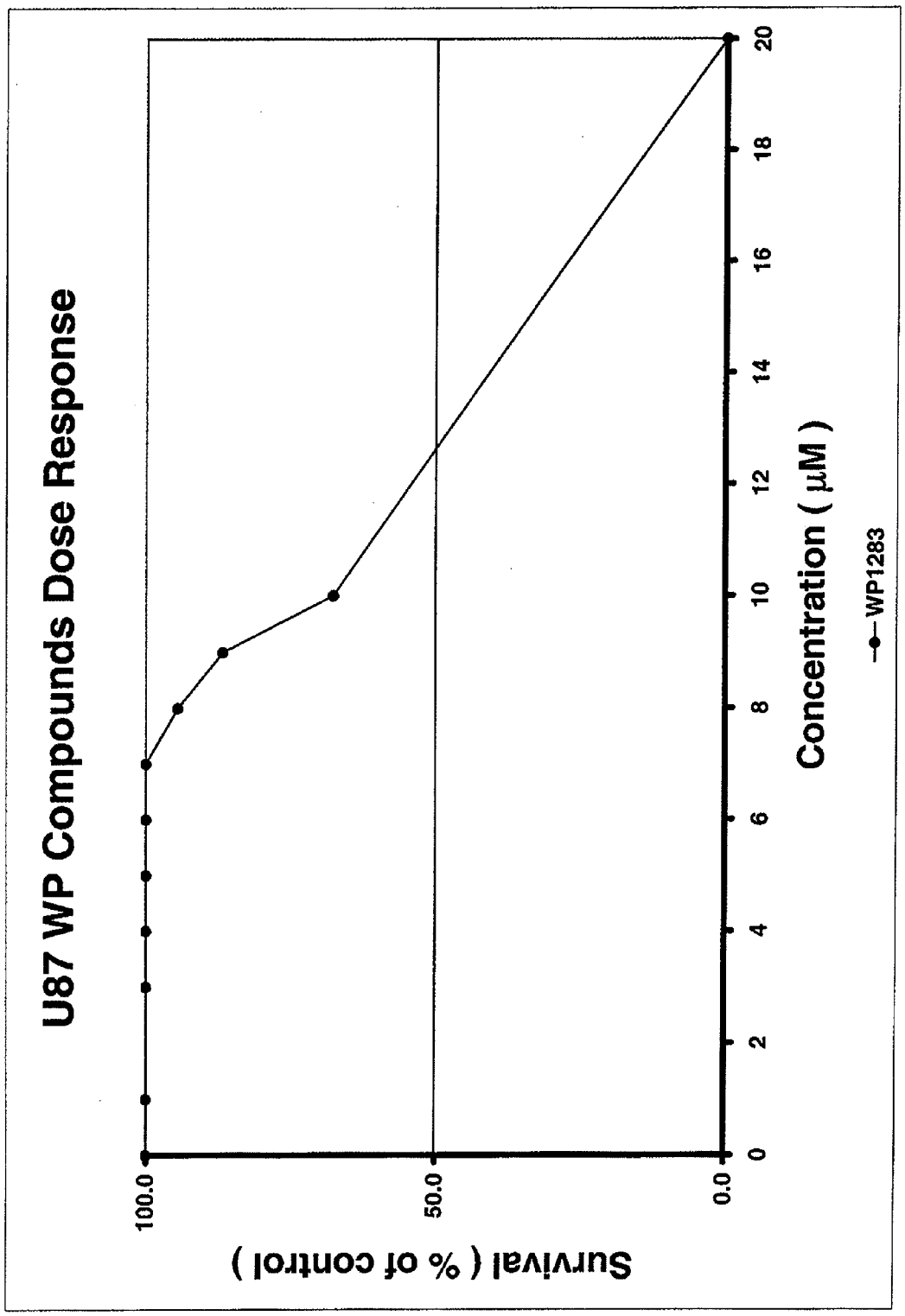
FIG. 23: Dose-response curve for WP1283 in the presence of the U87 cell line.
Figure 24:
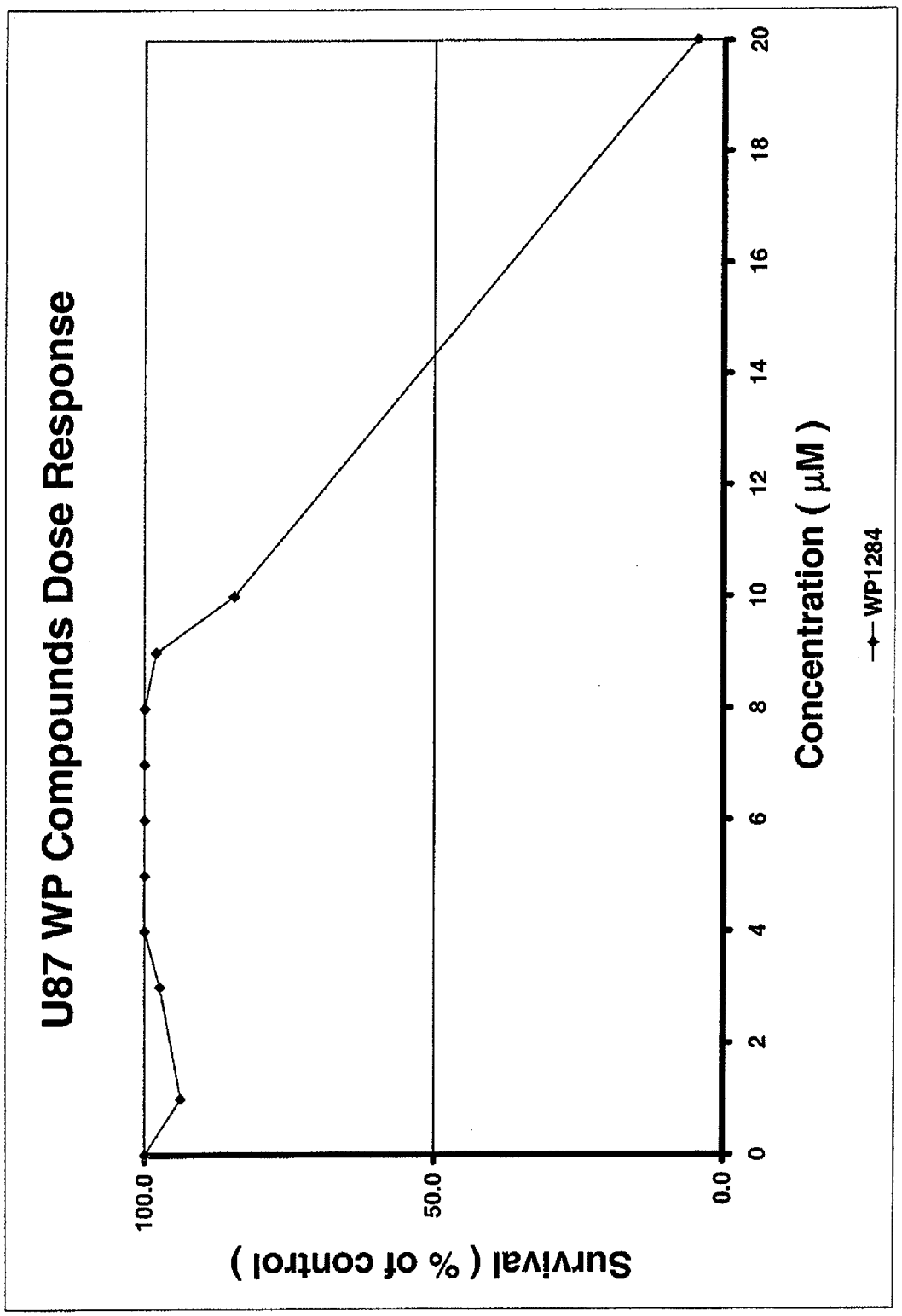
FIG. 24: Dose-response curve for WP1284 in the presence of the U87 cell line.
Figure 25:
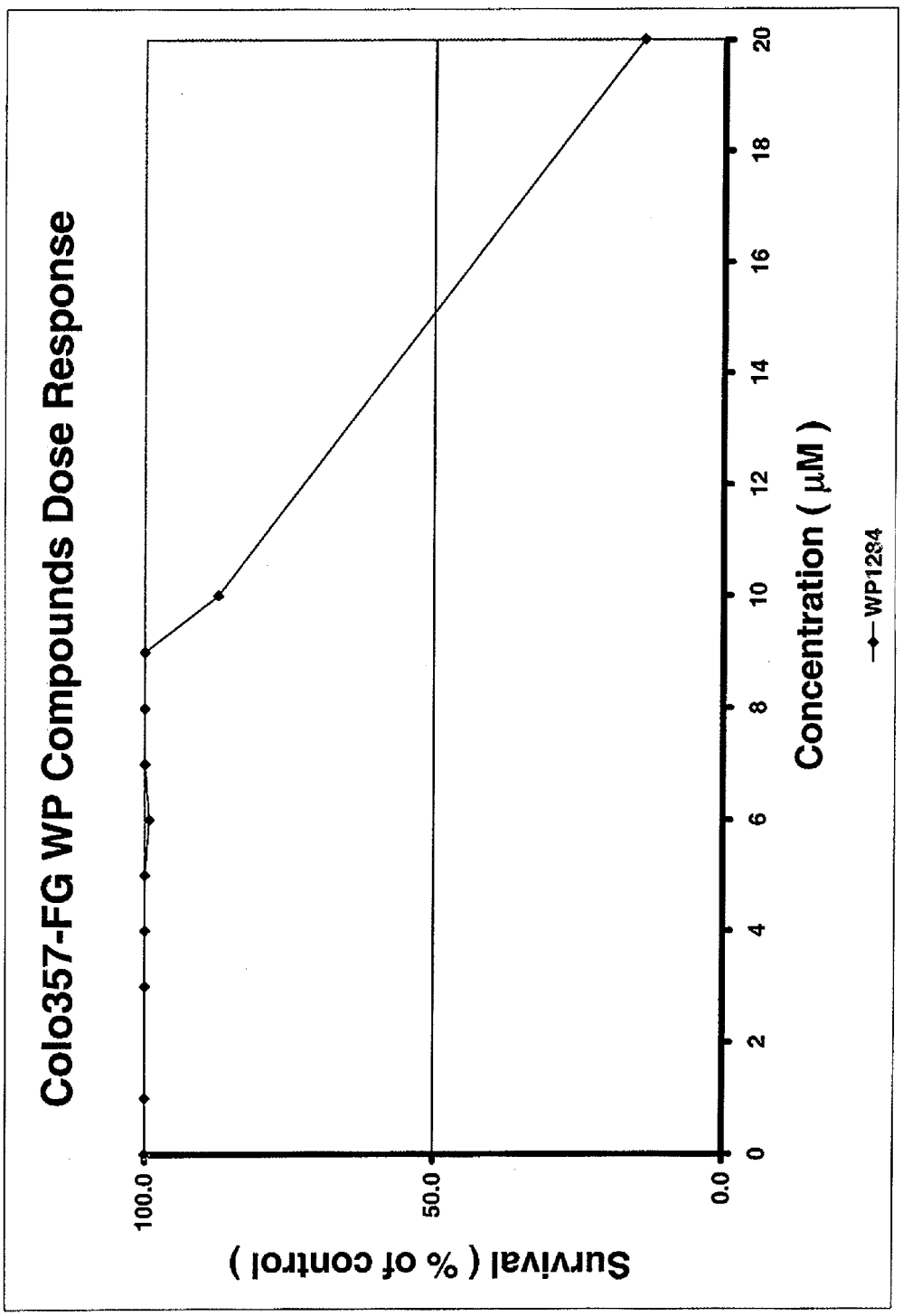
FIG. 25: Dose-response curve for WP1284 in the presence of the Colo357-FG cell line.
Figure 26:
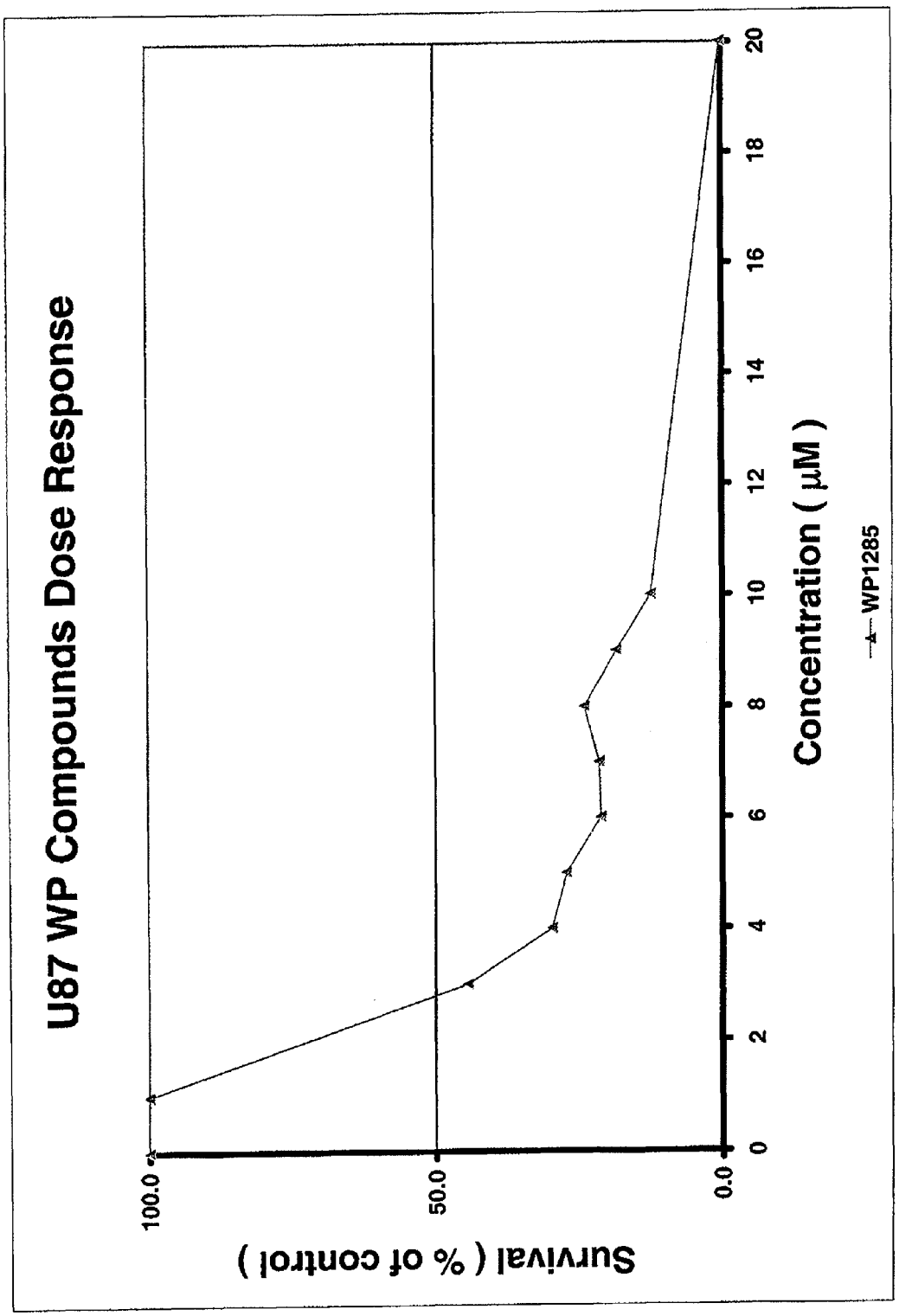
FIG. 26: Dose-response curve for WP1285 in the presence of the U87 cell line.
Figure 27:
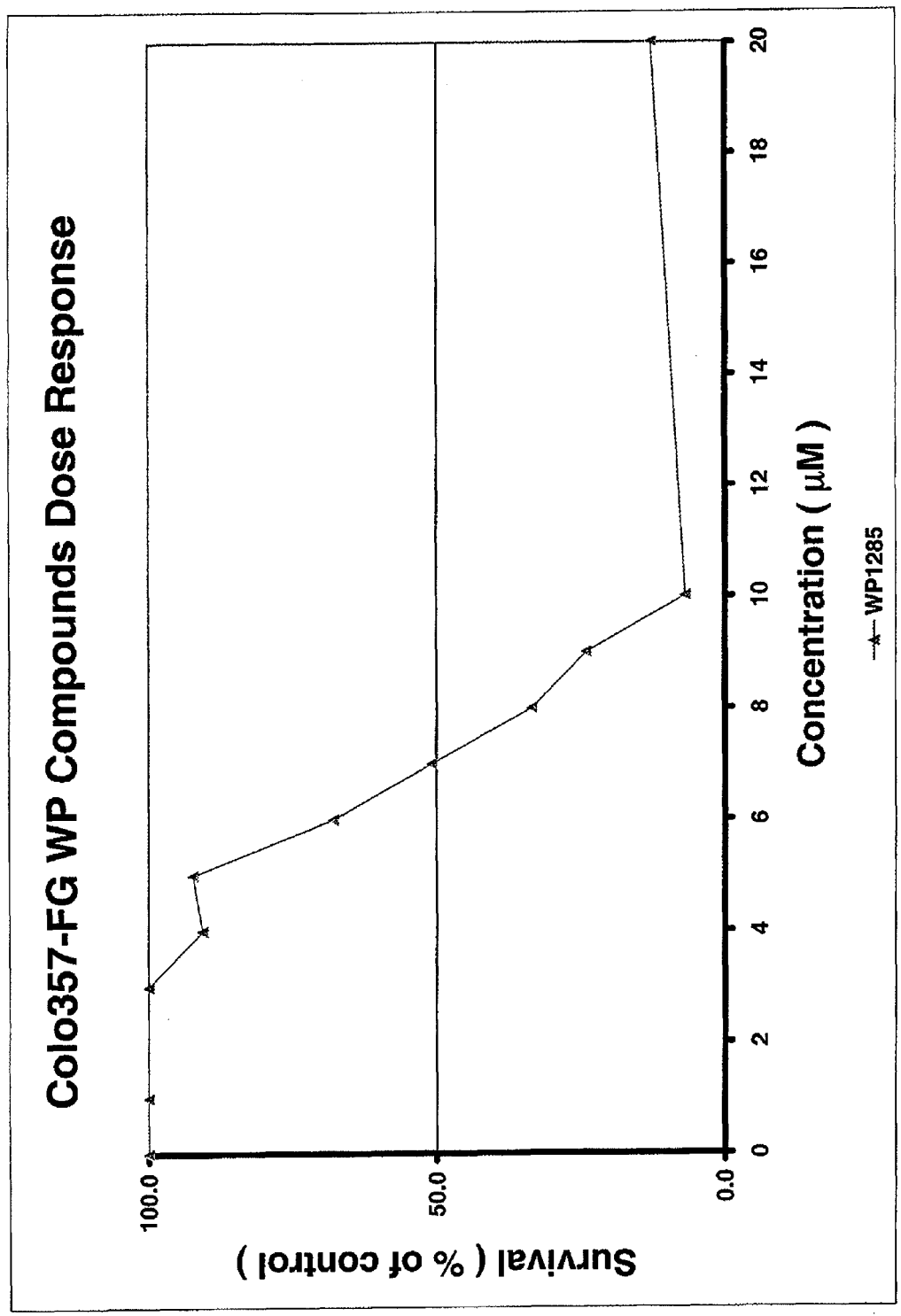
FIG. 27: Dose-response curve for WP1285 in the presence of the Colo357-FG cell line.
Figure 28:
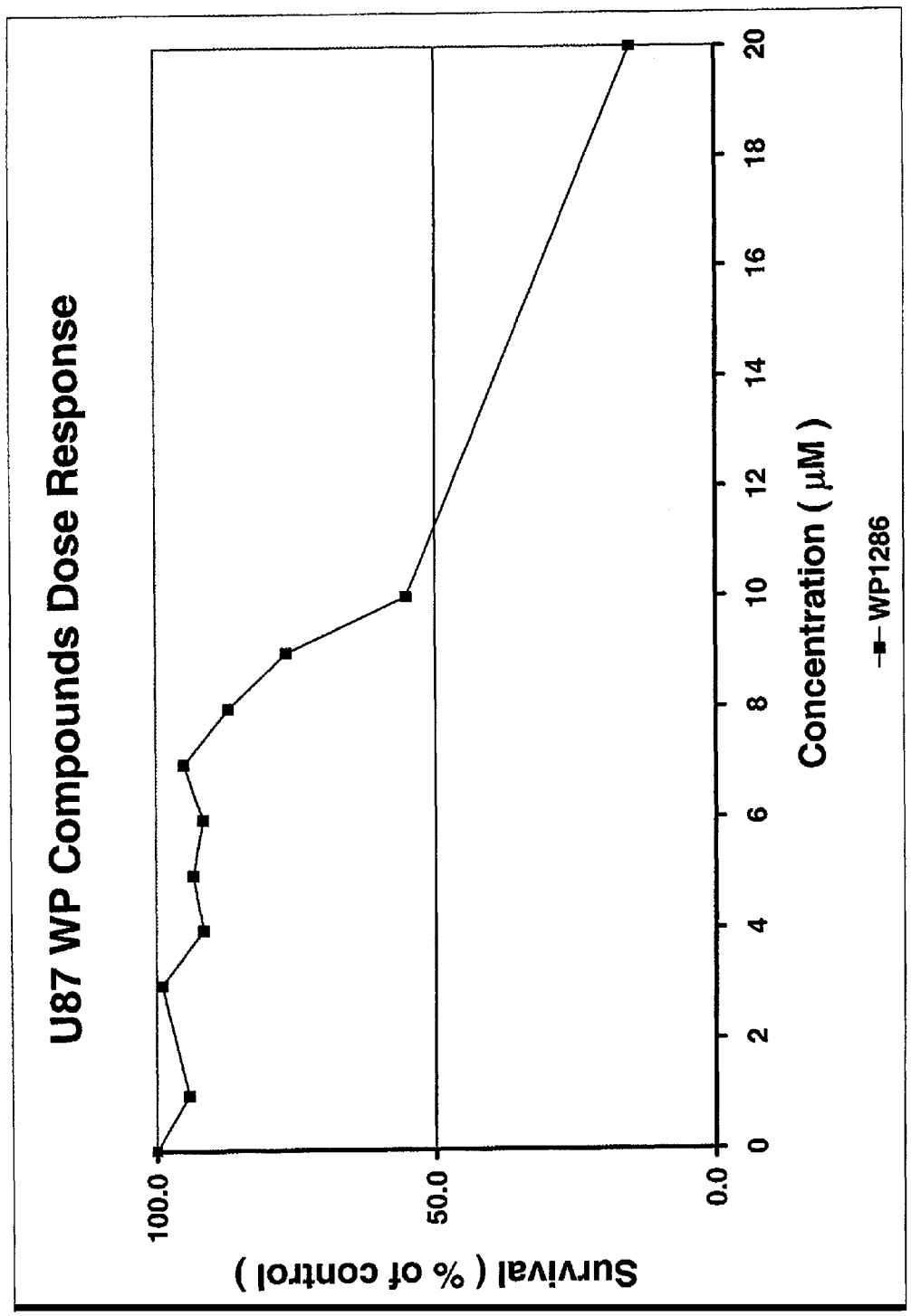
FIG. 28: Dose-response curve for WP1286 in the presence of the U87 cell line.
Figure 29:
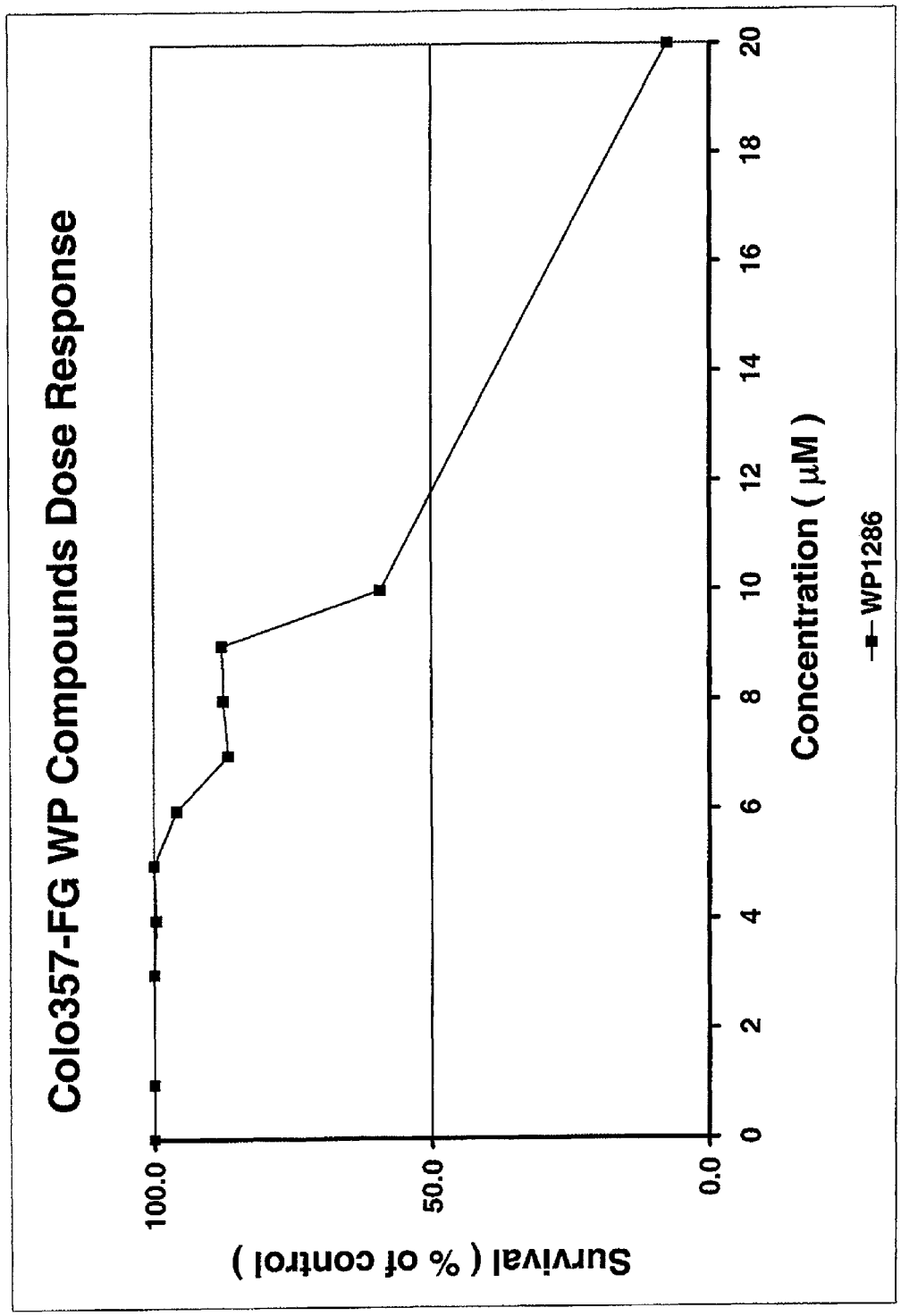
FIG. 29: Dose-response curve for WP1286 in the presence of the Colo357-FG cell line.
Figure 30:
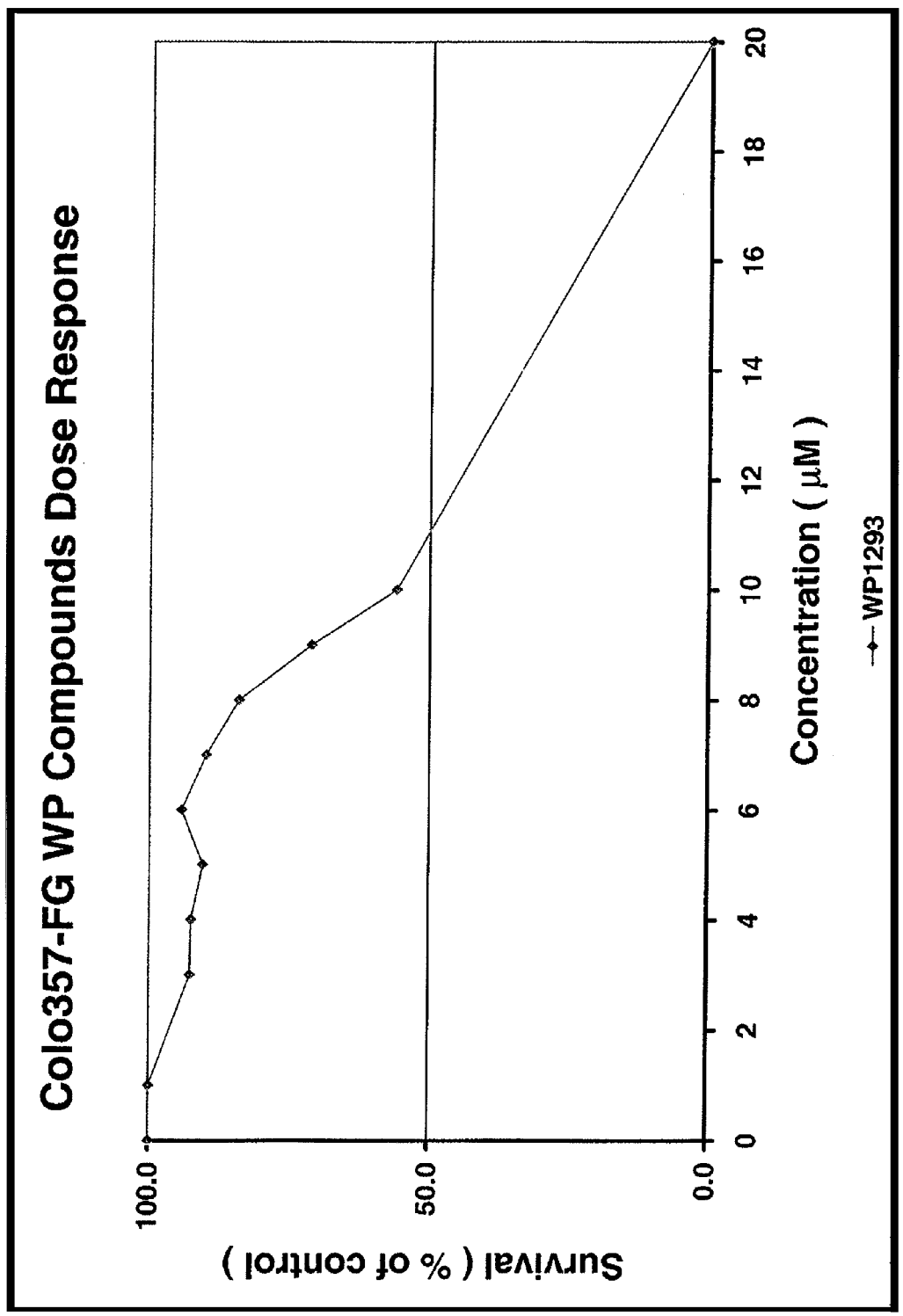
FIG. 30: Dose-response curve for WP1293 in the presence of the Colo357-FG cell line.
Figure 31:
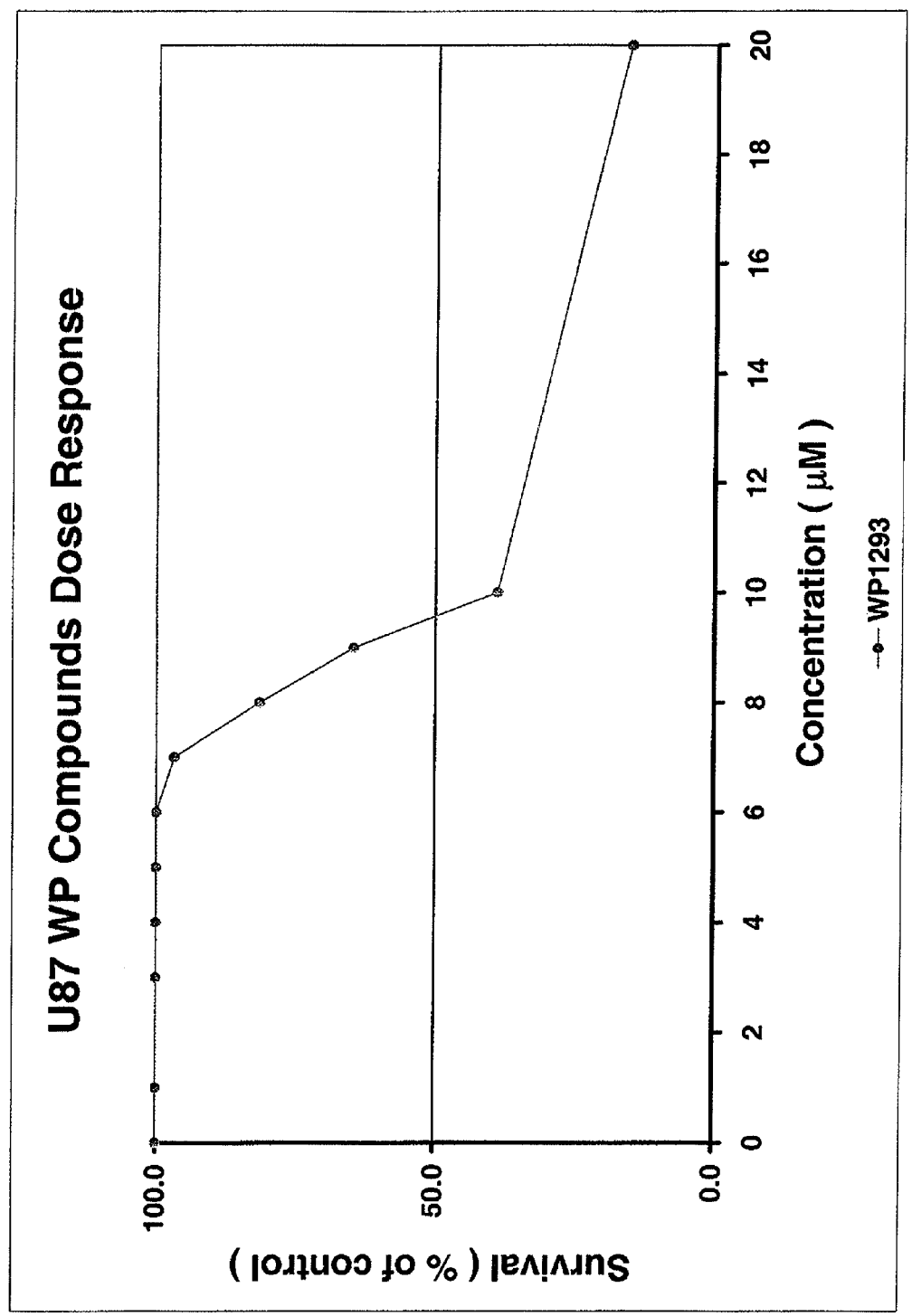
FIG. 31: Dose-response curve for WP1293 in the presence of the U87 cell line.
Figure 32:
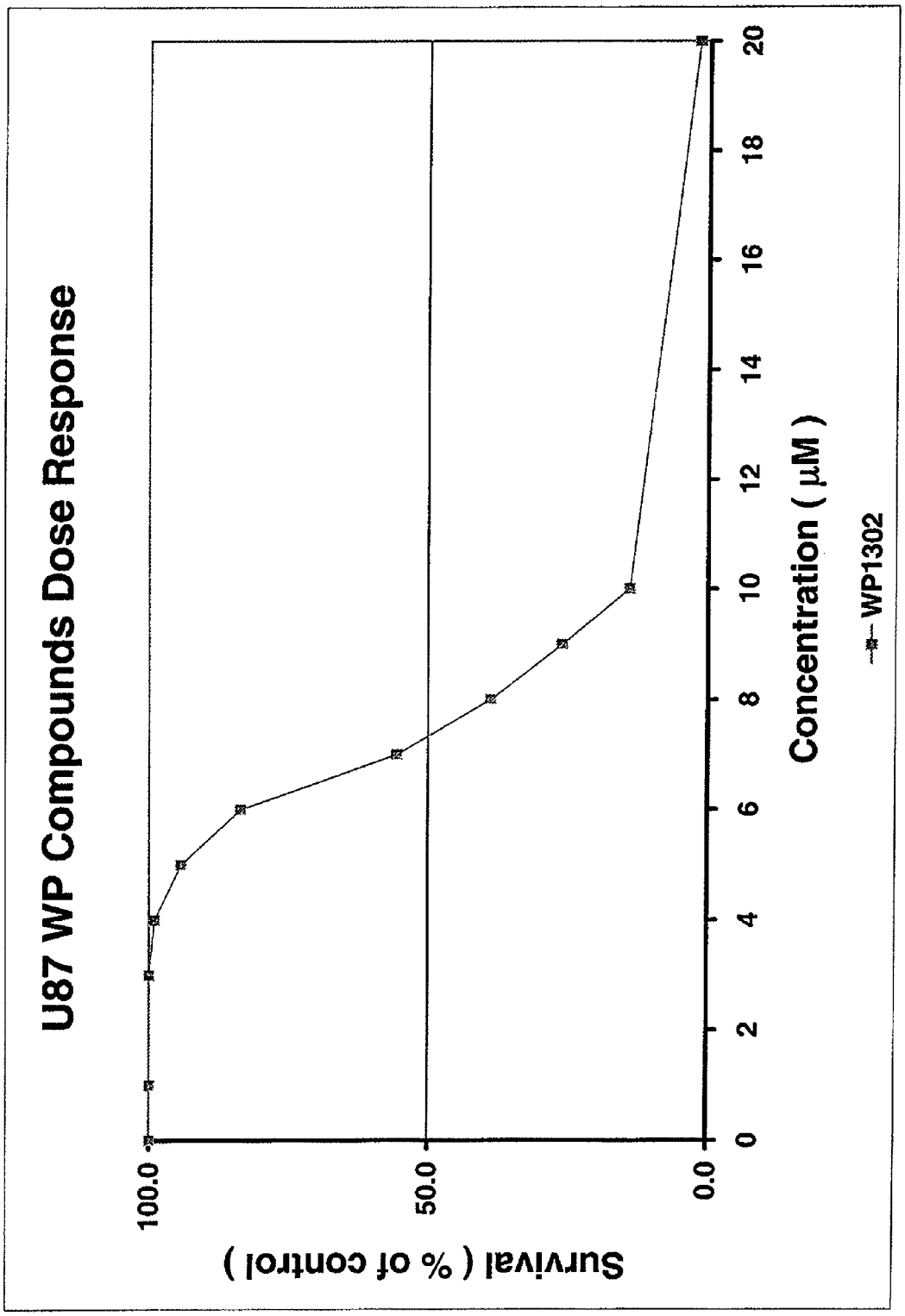
FIG. 32: Dose-response curve for WP1302 in the presence of the U87 cell line.
Figure 33:
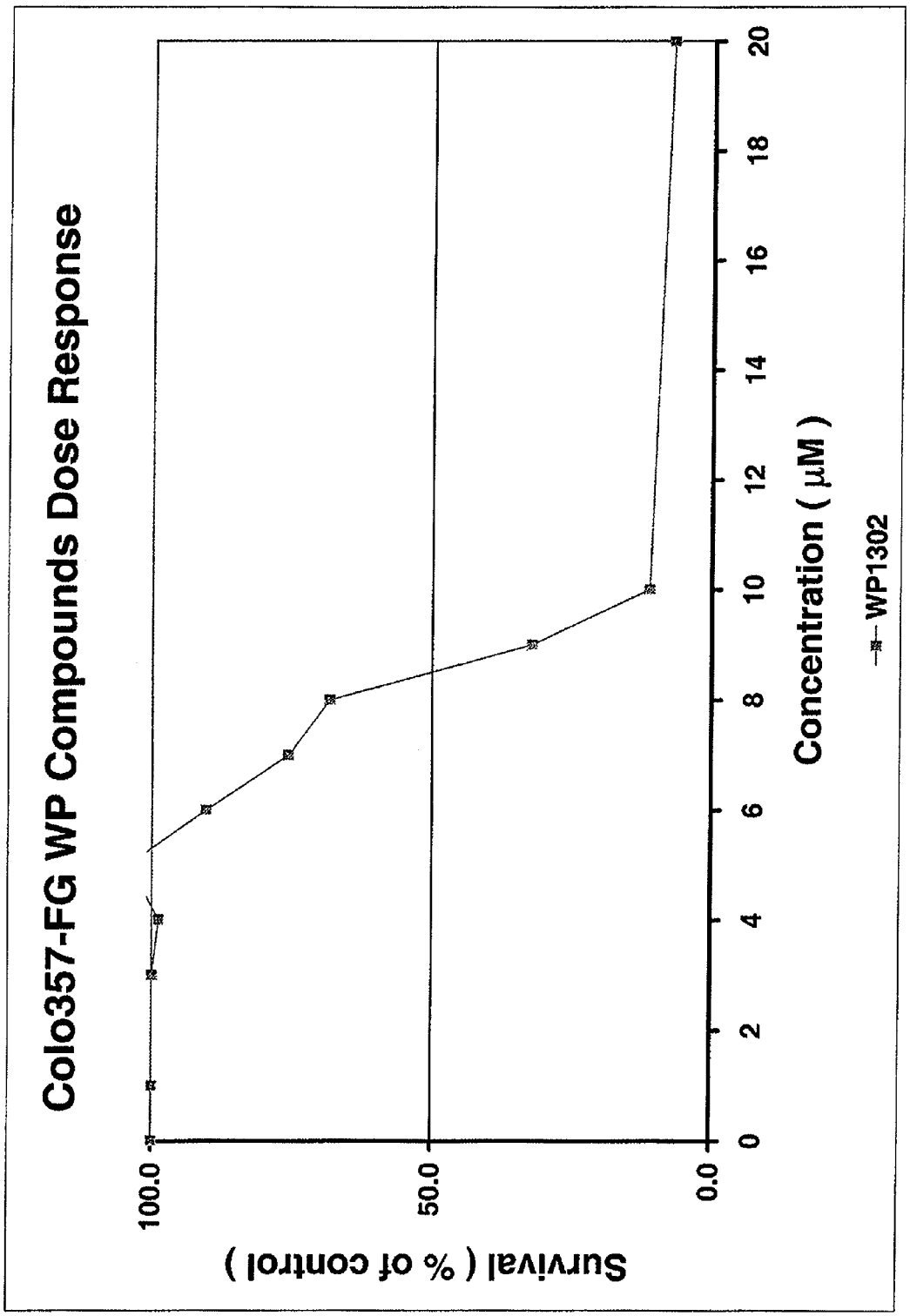
FIG. 33: Dose-response curve for WP1302 in the presence of the Colo357-FG cell line.

Previous studies have demonstrated that cytokine pathways that activate transcription factors (e.g., NF-kB, STAT3) are unregulated or activated by genetic lesions or autocrine/paracrine mechanisms in multiple tumor types (Hallek et al., 1998; Hideshima et al., 2002). These pathways contribute to the tumorigenicity and progression of cancer. In the present invention, new compounds were synthesized, and in vitro screening revealed that these compounds can block IL-6 mediated STAT3 activation at low concentrations (~1 µM). As compared to AG490, these compounds are significantly more potent (20 to 50-fold) in tumor cells in inhibiting Jak2/STAT3 signaling in IL-6 treated cells. These compounds can also induce apoptosis in wide range of solid and hematological tumor cells at concentrations that parallel their Jak2/STAT3 pathway downregulatory activity. The present invention discloses compounds that inactivate genes and signaling pathways important for tumor cell survival and progression, and these compounds may be used alone or in combination with other agents for the treatment of cancer.

II. Chemical Definitions

As used herein, the term "amino" means —$NH_2$; the term "nitro" means —$NO_2$; the term "halo" designates —F, —Cl, —Br or —I; the term "mercapto" means —SH; the term "cyano" means —CN; the term "silyl" means —$SiH_3$, and the term "hydroxy" means —OH.

An "alkane" refers to an acyclic branched or unbranched hydrocarbon, in many cases having the general formula $C_nH_{2n+2}$. An "alkyl" refers to a univalent group derived from an alkane by removal of a hydrogen atom from any carbon atom thus having the formula —$C_nH_{2n+1}$ in many cases. Alkyl groups, either straight-chained or branched chained, may be substituted with additional acyclic alkyl, cycloalkyl, or cyclic alkyl groups. The alkyl group may be heteroatom-substituted or heteroatom-unsubstituted, see below. Preferably, the alkyl group has 1 to 12 carbons. More preferably, it is a lower alkyl having 1 to 7 carbons, more preferably 1 to 4 carbons. An upper alkyl has 8 or more carbon atoms. A "divalent alkyl" refers to a divalent group derived from an alkane by removal of two hydrogen atoms from either the same carbon atom (e.g. methylene, ethylidene, propylidene) or from different carbon atoms (e.g. —$C_2H_4$—).

A "cycloalkane" refers to a saturated monocyclic hydrocarbons with or without side chains.

A "cycloalkyl" refers to a univalent group derived from cycloalkane by removal of a hydrogen atom from a ring carbon atom.

The term "heteroatom-substituted," when used to modify a class of organic radicals (e.g. alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —$NO_2$, —$N(CH_3)_2$, amino, or —SH. Specific heteroatom-substituted organic radicals are defined more fully below.

The term "heteroatom-unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —$C_6H_4C\equiv CH$ is an example of a heteroatom-unsubstituted aryl group, while —$C_6H_4F$ is an example of a heteroatom-substituted aryl group. Specific heteroatom-unsubstituted organic radicals are defined more fully below.

The term "heteroatom-unsubstituted $C_n$-alkyl" refers to an alkyl, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$, cyclopropylmethyl, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, and —$CH_2C(CH_3)_3$ are all examples of heteroatom-unsubstituted alkyl groups.

The term "heteroatom-substituted $C_n$-alkyl" refers to an alkyl, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2OCH(CH_2)_2$, —$CH_2NHCH(CH_2)_2$, —$CH_2CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, $CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2N(CH_2CH_3)_2$, —$CH_2CH_2NHCO_2C(CH_3)_3$, and —$CH_2Si(CH_3)_3$.

The term "heteroatom-unsubstituted $C_n$-cycloalkyl" refers to a cycloalkyl, further having a total of n carbon atoms, all of which are nonaromatic, 3 or more hydrogen atoms, and no heteroatoms. For example, a heteroatom-unsubstituted $C_1$-$C_{10}$-cycloalkyl has 1 to 10 carbon atoms. The groups —$CH(CH_2)_2$ (cyclopropyl), cyclobutyl, cyclopentyl, and cyclohexyl, are all examples of heteroatom-unsubstituted cycloalkyl groups.

The term "heteroatom-substituted $C_n$-cycloalkyl" refers to a cycloalkyl, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-cycloalkyl has 1 to 10 carbon atoms.

The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —CH=CH$_2$, —CH=CHCH$_3$, —CH=CHCH$_2$CH$_3$, —CH=CHCH$_2$CH$_2$CH$_3$, —CH=CHCH(CH$_3$)$_2$, —CH=CHCH(CH$_2$)$_2$, —CH$_2$CH=CH$_2$, —CH$_2$CH=CHCH$_3$, —CH$_2$CH=CHCH$_2$CH$_3$, —CH$_2$CH=CHCH$_2$CH$_2$CH$_3$, —CH$_2$CH=CHCH(CH$_3$)$_2$, —CH$_2$CH=CHCH(CH$_2$)$_2$, and —CH=CH—C$_6$H$_5$.

The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —CH=CHF, —CH=CHCl and —CH=CHBr, are examples of heteroatom-substituted alkenyl groups.

The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —C≡CH, —C≡CCH$_3$, and —C≡CC$_6$H$_5$ are examples of heteroatom-unsubstituted alkynyl groups.

The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —C≡CSi(CH$_3$)$_3$, is an example of a heteroatom-substituted alkynyl group.

The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Examples of heteroatom-unsubstituted aryl groups include phenyl, methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, quinolyl, indolyl, and the radical derived from biphenyl. The term "heteroatom-unsubstituted aryl" includes carbocyclic aryl groups, biaryl groups, and radicals derived from polycyclic fused hydrocarbons (PAHs).

The term "heteroatom-substituted $C_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OCOCH$_3$, —C$_6$H$_4$OC$_6$H$_5$, —C$_6$H$_4$NH$_2$, —C$_6$H$_4$NHCH$_3$, —C$_6$H$_4$NHCH$_2$CH$_3$, —C$_6$H$_4$CH$_2$Cl, —C$_6$H$_4$CH$_2$Br, —C$_6$H$_4$CH$_2$OH, —C$_6$H$_4$CH$_2$OCOCH$_3$, —C$_6$H$_4$CH$_2$NH$_2$, —C$_6$H$_4$N(CH$_3$)$_2$, —C$_6$H$_4$CH$_2$CH$_2$Cl, —C$_6$H$_4$CH$_2$CH$_2$OH, —C$_6$H$_4$CH$_2$CH$_2$OCOCH$_3$, —C$_6$H$_4$CH$_2$CH$_2$NH$_2$, —C$_6$H$_4$CH$_2$CH=CH$_2$, —C$_6$H$_4$CF$_3$, —C$_6$H$_4$CN, —C$_6$H$_4$C≡CSi(CH$_3$)$_3$, —C$_6$H$_4$COH, —C$_6$H$_4$COCH$_3$, —C$_6$H$_4$COCH$_2$CH$_3$, —C$_6$H$_4$COCH$_2$CF$_3$, —C$_6$H$_4$COC$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —COCH$_3$, —COCH$_2$CH$_3$, —COCH$_2$CH$_2$CH$_3$, —COCH(CH$_3$)$_2$, —COCH(CH$_2$)$_2$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, and —COC$_6$H$_3$(CH$_3$)$_2$, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —$OCH_3$, —$OCH_2CH_3$, —$OCH_2CH_2CH_3$, —$OCH(CH_3)_2$, and —$OCH(CH_2)_2$.

The term "heteroatom-substituted $C_n$-alkoxy" refers to a group, having the structure —OR, in which R is a heteroatom-substituted $C_n$-alkyl, as that term is defined above. For example, —$OCH_2CF_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above.

The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above.

The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —$OC_6H_5$.

The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —$OCOCH_3$ is an example of a heteroatom-unsubstituted acyloxy group.

The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl (alkynyl)amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

The term "heteroatom-unsubstituted $C_n$-sulfonamido" refers to a radical, having a single nitrogen atom as the point of attachment, further having a sulfonyl group attached via its sulfur atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term amido includes N-alkyl-sulfonamido, N-aryl-sulfonamido, N-aralkyl-sulfonamido, sulfonylamino, alkylsulfonamino, and arylsulfonamino groups. The group, —NHS(O)$_2$CH$_3$, is an example of a heteroatom-unsubstituted sulfonamido group.

The term "heteroatom-substituted C$_n$-sulfonamido" refers to a radical, having a single nitrogen atom as the point of attachment, further having a sulfonyl group attached via its sulfur atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the sulfur and oxygen atoms of the sulfonyl group, wherein each additional heteroatom is independently selected from the group consisting of N, O, F, Cl, Br, I, Si, P, and S. For example, a heteroatom-substituted C$_1$-C$_{10}$-sulfonamido has 1 to 10 carbon atoms. The group, —NHS(O)$_2$OCH$_3$, is an example of a heteroatom-substituted sulfonamido group.

The term "heteroatom-unsubstituted C$_n$-alkylthio" refers to a group, having the structure —SR, in which R is a heteroatom-unsubstituted C$_n$-alkyl, as that term is defined above. The group, —SCH$_3$, is an example of a heteroatom-unsubstituted alkylthio group.

The term "heteroatom-substituted C$_n$-alkylthio" refers to a group, having the structure —SR, in which R is a heteroatom-substituted C$_n$-alkyl, as that term is defined above.

The term "heteroatom-unsubstituted C$_n$-alkenylthio" refers to a group, having the structure —SR, in which R is a heteroatom-unsubstituted C$_n$-alkenyl, as that term is defined above.

The term "heteroatom-substituted C$_n$-alkenylthio" refers to a group, having the structure —SR, in which R is a heteroatom-substituted C$_n$-alkenyl, as that term is defined above.

The term "heteroatom-unsubstituted C$_n$-alkynylthio" refers to a group, having the structure —SR, in which R is a heteroatom-unsubstituted C$_n$-alkynyl, as that term is defined above.

The term "heteroatom-substituted C$_n$-alkynylthio" refers to a group, having the structure —SR, in which R is a heteroatom-substituted C$_n$-alkynyl, as that term is defined above.

The term "heteroatom-unsubstituted C$_n$-arylthio" refers to a group, having the structure —SAr, in which Ar is a heteroatom-unsubstituted C$_n$-aryl, as that term is defined above. The group, —SC$_6$H$_5$, is an example of a heteroatom-unsubstituted arylthio group.

The term "heteroatom-substituted C$_n$-arylthio" refers to a group, having the structure —SAr, in which Ar is a heteroatom-substituted C$_n$-aryl, as that term is defined above.

The term "heteroatom-unsubstituted C$_n$-aralkylthio" refers to a group, having the structure —SAr, in which Ar is a heteroatom-unsubstituted C$_n$-aralkyl, as that term is defined above. The group, —SCH$_2$C$_6$H$_5$, is an example of a heteroatom-unsubstituted aralkyl group.

The term "heteroatom-substituted C$_n$-aralkylthio" refers to a group, having the structure —SAr, in which Ar is a heteroatom-substituted C$_n$-aralkyl, as that term is defined above.

The term "heteroatom-unsubstituted C$_n$-acylthio" refers to a group, having the structure —SAc, in which Ac is a heteroatom-unsubstituted C$_n$-acyl, as that term is defined above. The group, —SCOCH$_3$, is an example of a heteroatom-unsubstituted acylthio group.

The term "heteroatom-substituted C$_n$-acylthio" refers to a group, having the structure —SAc, in which Ac is a heteroatom-substituted C$_n$-acyl, as that term is defined above.

The term "heteroatom-unsubstituted C$_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted C$_1$-C$_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are examples of heteroatom-unsubstituted alkylsilyl groups.

The term "heteroatom-substituted C$_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted C$_1$-C$_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use-A Handbook (2002), which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "$IC_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein the specification, "a" or "an" may mean one or more. As used herein in the claim(s), when used in conjunction with the word "comprising" or "having," the words "a" or "an" may mean one or more than one. As used herein "another" may mean at least a second or more.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

III. Caffeic Acid, its Derivatives and their Analogs

The present invention provides caffeic-like compounds for the treatment of cell proliferative diseases such as cancer. The compounds of the present invention are shown above, in the summary of the invention, the claims, as well as the examples below.

IV. Cell Proliferative Diseases

The term "cell proliferative diseases" refers to disorders resulting from abnormally increased and/or uncontrolled growth of cell(s) in a multicellular organism that results in harm (e.g., discomfort or decreased life expectancy) to the multicellular organism. Cell proliferative diseases can occur in animals or humans. Cancer is an example of a cell proliferative disease, and certain embodiments of the present invention are directed towards the treatment of cancer.

In certain embodiments, compounds and methods of the present invention may be used to treat a wide variety of cancerous states including, for example, melanoma, non-small cell lung, small cell lung, lung, hepatocarcinoma, retinoblastoma, astrocytoma, glioblastoma, leukemia, blood, brain, skin, eye, tongue, gum, neuroblastoma, head, neck, breast, pancreatic, renal, bone, testicular, ovarian, mesothelioma, cervical, gastrointestinal, lymphoma, colon, and/or bladder. The cancer may comprise a tumor made of cancer cells. These cancerous states may include cells that are cancerous, pre-cancerous, and/or malignant.

It is also anticipated that compounds of the present invention may also be used to treat cell proliferative diseases other than cancer. Other cell proliferative diseases that may be treated in certain embodiments of the present invention include, for example, rheumatoid arthritis, inflammatory bowel disease, osteoarthritis, leiomyomas, adenomas, lipomas, hemangiomas, fibromas, vascular occlusion, restenosis, artherosclerosis, pre-neoplastic lesions (e.g., adenomatous hyperplasia, prostatic intraepithelial neoplasia), carcinoma in situ, oral hairy leukoplakia and/or psoriasis and the variant forms of psoriasis including psoriatic arthritis other skin inflammatory conditions such as urticaria, excema, atopic dermatitis, granuloma annulare, angiomas, basal cell carcinoma, squamous cell carcinoma, malignant melanoma, seborrheic dermatitis, rosacea other hyperactive autoimmune disorders such as rheumatoid arthritis, chronic active hepatitis, Hashimoto's thyroiditis, lupus, connective tissue disorders, mixed connective tissue disorders, and neurologic inflammatory diseases such as multiple sclerosis, inflammatory leukoencephalitis.

Figure 34:
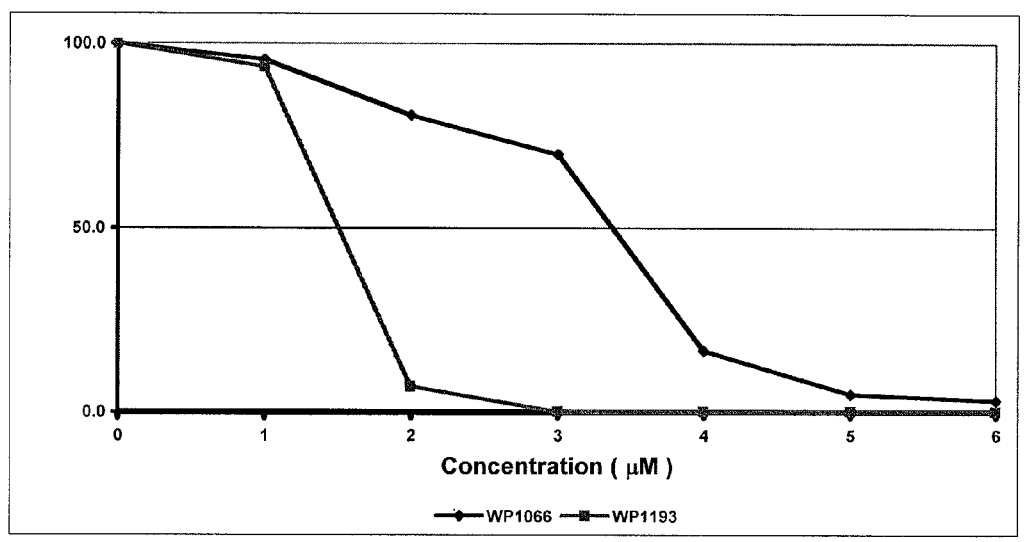
FIG. 34: Compound WP1193 more potently than WP1066 inhibits STAT3 phosphorylation. The graph shows survival (% of control) vs. concentration in micromolar units.

The compounds of the present invention may function by selectively inhibiting STAT3 phosphorylation as has been described in Iwamaru et al., (2006), which is incorporated herein by reference. In those studies, WP1066, an inhibitor structurally related to AG490 but significantly more potent and active, against human malignant glioma U87-MG and U373-MG cells in vitro and in vivo. $IC_{50}$ values for WP1066 were shown to be 5.6 µM in U87-MG cells and 3.7 µM in U373-MG cells, which represents 18-fold and eightfold increases in potency, respectively, over that of AG490. WP1066 activated Bax, suppressed the expression of c-myc, Bcl-$X_L$ and Mcl-1, and induced apoptosis. Systemic intraperitoneal administration of WP1066 in mice significantly ($P<0.001$) inhibited the growth of subcutaneous malignant glioma xenografts during the 30-day follow-up period. Immunohistochemical analysis of the excised tumors revealed that phosphorylated STAT3 levels in the WP1066 treatment group remained inhibited at 3 weeks after the final WP1066 injection, whereas tumors from the control group expressed high levels of phosphorylated STAT3. Compounds of the present invention may even be more potent than WP1066. For example, as shown in FIG. 34, compound WP1193 was shown to inhibit STAT3 phosphorylation potently than WP1066 inhibits. Given the structural similarity between the compounds of the present invention and the compounds tested in Iwamaru et al., 2006, the invention contemplates that the compounds of the present invention will be effective to treat a variety of cancer types, including: human malignant gliomas, which are the most common malignancies in the brain, and astrocytic tumors of World Health Organization grades II-IV (2002). The invention further contemplates that the compounds of the present invention will be useful to treat those tumors in which the STAT3 is constitutively activated, such as those cancers described in Yu and Jove (2004), which is incorporated herein by reference. These tumors include solid tumors, such as breast cancer, head and neck cancer, melanoma, ovarian cancer, lung cancer, pancreatic cancer and prostate cancer, and blood tumors, such as multiple myeloma, leukemias (e.g. HTLV-I-dependent, acute myelogenous leukemia, large granular lymphocyte leukemia), and lymphomas (e.g. EBV-related/Burkitt's, mycosis fungoides, cutaneous T-cell lymphoma, non-Hodgkin's lymphoma and anaplastic large-cell lymphoma). The compounds of the present invention are also expected to be able to penetrate the blood brain barrier, based on their structural similarity to WP1066.

Additionally, compounds of the present invention may be used to treat diseases other than hyperproliferative diseases. For example, certain WP compounds may be useful for the treatment of hypertrophy and ischemia (U.S. Pat. No. 6,433,018) as well as hepatitis B infection (U.S. Pat. No. 6,420,338). Thus compounds of the present invention may also be useful for the treatment of other diseases including hypertrophy, ischemia, and a viral infection (e.g., hepatitis B infection), psoriasis and the variant forms of psoriasis including psoriatic arthritis other skin inflammatory conditions such as urticaria, excema, atopic dermatitis, granuloma annulare, angiomas, basal cell carcinoma, squamous cell carcinoma, malignant melanoma, seborrheic dermatitis, rosacea other hyperactive autoimmune disorders such as rheumatoid arthritis, chronic active hepatitis, Hashimoto's thyroiditis, lupus, connective tissue disorders, mixed connective tissue disorders, and neurologic inflammatory diseases such as multiple sclerosis, inflammatory leukoencephalitis.

V. Pharmaceutical Compositions

The anti-tumor compounds of this invention can be administered to kill certain cells involved in a cell proliferative disease, such as tumor cells, by any method that allows contact of the active ingredient with the agent's site of action in the tumor. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the selected route of administration and standard pharmaceutical practice.

Aqueous compositions of the present invention will have an effective amount of the compounds to kill or slow the growth of cancer cells. Such compositions will generally be dissolved or dispersed in a pharmaceutically acceptable carrier or aqueous medium.

The terms "AG compounds" and "WP compounds" refer to specific examples of the present invention.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants, lipid carriers, liposomes and the like.

A. Parenteral Administration

The active compounds will often be formulated for parenteral administration, e.g., formulated for injection via the intravenous, intramuscular, subcutaneous, or even intraperitoneal routes. The preparation of an aqueous composition that contains an anthracycline of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the compounds in salt form, generally to improve the solubility and bioavailability and to provide an active drug form more readily assimilated. As used herein, the term "pharmaceutically acceptable salt" refers to compounds which are formed from acidifying a substituted anthracycline solution with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The compounds of the present invention may also be formulated into a composition comprising liposomes or any other lipid carrier. Liposomes include: multivesicular liposomes, multilamellar liposomes, and unilamellar liposomes.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

VI. Therapies

One of the major challenges in oncology today is the effective treatment of a given tumor. Tumors are often resistant to traditional therapies. Thus, a great deal of effort is being directed at finding efficacious treatment of cancer. One way of achieving this is by combining new drugs with the traditional therapies. In the context of the present invention, it is contemplated that therapies using the compounds could be used in combination with surgery, chemotherapy, radiotherapy, and/or a gene therapy.

"Effective amounts" or a "therapeutically relevant amount" are those amounts of a compound sufficient to produce a therapeutic benefit (e.g., effective to reproducibly inhibit decrease, reduce, inhibit or otherwise abrogate the growth of a cancer cell). An effective amount, in the context of treating a subject, is sufficient to produce a therapeutic benefit. The term "therapeutic benefit" as used herein refers to anything that promotes or enhances the well-being of the subject with respect to the medical treatment of the subject's cell proliferative disease. A list of nonexhaustive examples of this includes extension of the patients life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and/or a decrease in pain to the subject that can be attributed to the patient's condition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

General Method for Synthesis of Compounds

The following scheme shows a method for preparation of a specific caffeic acid analog. By using analogs of the starting materials indicated, a person of skill in the art may use this method to make other caffeic acid analogs.

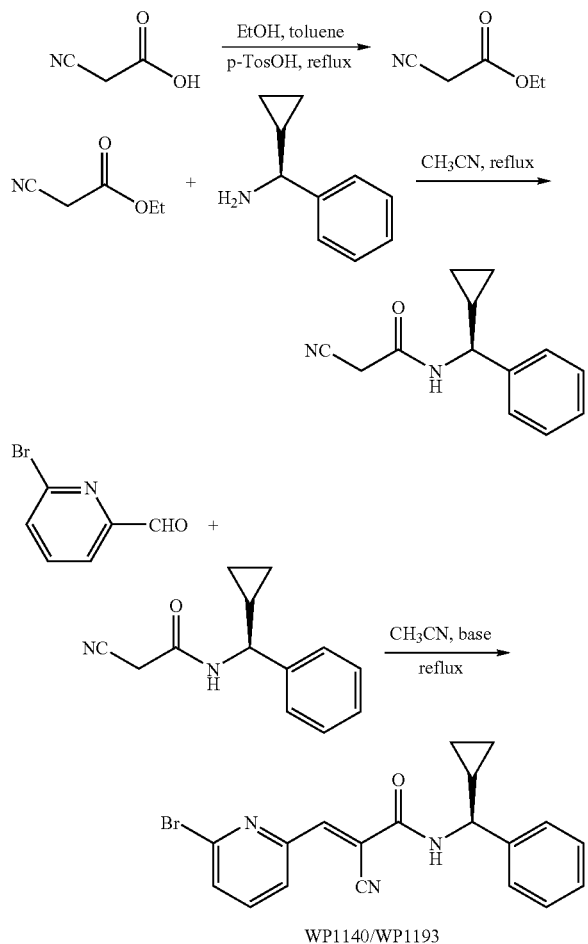

Preparation of 2-methyl-1-oxido-6-substituted pyridines

Hydrogen peroxide (1 ml of 35%, w/v, 10 mmol) was added to a solution of the pyridine compound (10 mmol) in glacial acetic acid (6 ml), and the mixture was heated at 70-80° C. with stirring for 3 hr. Additional aliquot of 35% (w/v) $H_2O_2$ was added and the reaction was to allowed to proceed for 9 hr at 70-80° C. The volume of the reaction mixture was reduced in vacuum, water (2 ml) was added, the mixture was concentrated in vacuum, and the residue was made alkaline using dry $Na_2CO_3$. Chloroform (5 ml) was added, this mixture was allowed to stand at 25° C. for 5 min., and the insoluble $Na_2CO_3$ and NaOAc were removed by filtration. Drying the filtrate (sodium sulfate) and removal of the solvent in vacuum gave the target product. Yield depend on substituent in position 2 55% to 85%. Products without further purification were used in the next step.

General Method for the Preparation of 2-(acetoxymethyl)-6-substituted pyridines

A solution of the 2-methyl-1-oxido-3-substituted pyridine (6 mmol) in acetic anhydride (4.32 g, 42 mmol, 4 ml) was refluxed for 1 hr. Ethanol (3 ml) was added to the reaction mixture, and the reaction was allowed to proceed at reflux for 10 min. The reaction mixture was cooled in an ice-water bath poured onto water (10 ml), and neutralized with 10% aqueous $NaHCO_3$. Extraction with ether (2×25 ml), washing the extract with brine solution (10 ml), drying the organic fraction (sodium sulfate), and removal of the solvent in vacuum gave a residue. Purification of the residue by silica gel column chromatography using hexanes/ethyl acetate (70/30, v/v) as eluent afforded the respective product as an oil, which was subsequently used for the preparation of 2-hydroxymethyl-6-substituted-pyridines.

General Method for the Preparation of 2-hydroxymethyl-6-substituted-pyridines

A mixture of a 2-(acetoxymethyl)-6-substituted pyridine (5 mmol), 1N NaOH (6 ml) and MeOH (12 ml) was stirred at 25° C. for 1.5 hr. The reaction mixture was poured onto water (30 ml) Extraction with ethyl acetate (2×50 ml), washing the EtOAc extract with brine (10 ml), drying the ethyl acetate fraction ($Na_2SO_4$), and removal of the solvent in vacuum gave the residue. Purification of the residue by silica gel column chromatography using hexanes/ethyl acetate (60/40, v/v) as eluent afforded the respective product as an oil, which was subsequently used for the preparation of 6-substituted-2-pyridinecarboxyaldehydes.

General Method for the Preparation of 6-substituted-2-pyridinecarboxyaldehydes

A solution of anhydrous $H_3PO_4$ in DMSO (1.5 ml of 1.0M) was added to a solution of the 6-substituted-2-(hydroxymethyl)-pyridine (3 mmol) and N,N-dicyclohexylcarbodiimide (1.86 g, 9 mmol) in DMSO (7 ml), and the reaction was allowed to proceed with stirring at 25° C. for 1.5 hr. The precipitated dicyclohexylourea was filtered, the filtered solid washed with ether (15 ml), and the water wash was extracted with ether (2×30 ml). The combined organic solutions were washed with brine (10 ml), the organic fraction was dried (sodium sulfate), and the solvent was removed in vacuum. The residue obtained was purified by silica gel column chromatography using ether/hexanes (40/60, v/v), as eluent to afford the respective product.

Preparation of the Ligand: (S)-2-amino-3-methyl-1,1-diphenylbutan-1-ol

A solution of phenylmagnesium bromide (3.0 M, 600 mL), 1.7 mol) in diethyl ether was stirred at 0° C. and diluted with THF (300 mL), followed by portionwise addition of L-valine methyl ester hydrochloride (50 g, 0.298 mol) while keeping the temperature below 10° C. After stirring for 3 hr at rt, the reaction mixture was poured slowly into ice-cold ammonium chloride solution. Diethyl ether (500 mL) and ethyl acetate (500 mL) were added to the mixture. After separation of the phases, the aqueous phase was re-extracted with tert-butylmethyl ether (1 L). The combined organic phases were stirred at 0° C. and acidified slowly with 35% hydrochloric acid (about 40 mL) and water. The hydrochloride precipitate thus formed was filtered off and rinsed with tert-butylmethyl ether. The mixture was then taken up in dichloromethane (1 L) and water (1 L) and basified at 0° C. with 35% sodium hydroxide (about 50 mL). After separation of the phases the aqueous phase was re-extracted with dichloromethane (1 L). The combined organic phases were washed with water and then with brine, dried over sodium sulfate and concentrated. After crystallization from iso-propyl ether (S)-2-amino-3-methyl-1,1-diphenylbutan-1-ol was obtained (61 g, 87%).

Synthesis of Enantiomeric Amines

A solution of (S)-2-amino-3-methyl-1,1-diphenylbutan-1-ol (47 mmol, 12 g) in THF (80 mL) was stirred at temperature below 30° C. followed by slow addition of borane-tetrahydrofuran solution (1M, 95 mL). The temperature was allowed to rise to room temperature over 2 h, The reaction mixture was then stirred at 0° C. and the solution of pure anti-cyclopropyl (phenyl)methamine-benzyl oxime (19 mmol, 5 g), in THF (10 mL) was added. After stirring the mixture for 20 h at room temperature, the reaction mixture was cooled to 0° C. and treated with hydrochloric acid (2N, 100 mL). The mixture was stirred for 16 h then basified at 0° C. by addition of 35% sodium hydroxide (100 mL) followed by extraction with ethyl acetate. Extract washed with water and brine, dried over sodium sulfate and evaporated to dryness. Amine was purified by LC (BIOTAGE SP1 purification system), using chloroform:methanol (gradient up to 25% of methanol) to give 2.1 g of (S)-cyclopropyl(phenyl)methanamine, yield 72%.

Preparation of Ethyl Cyanoacetate

The mixture of cyanoacetic acid (1 mmol), ethyl alcohol (1 ml) and p-toluenesulfonic acid (0.1 mmol) were refluxed with toluene (20 ml) for 12 hr. The reaction mixture washed with sat. sodium bicarbonate, then with water until neutral. Organic solution was dried over sodium sulfate. The drying agent and solvents were removed, and crude ester was distilled under reduced pressure 97-98° C./21.3 hPa (16 mmHg). Yield 72%.

Preparation of N-(Phenylalkyl)cinnamides (General Procedure)

The mixture of (S)-cyclopropyl(phenyl)methanamine (4.12 g, 28 mmol) and ethyl cyanoacetate (9.4 g, 84 mmol) in toluene (10 mL) was prepared and stirred under reflux for 4 hr. Progress of the reaction was monitored by TLC method. After reaction was completed the solvent was evaporated to dryness. Product was purified using LC (Biotage SP1, purification system) to give 4.08 g (68%) of N-((S)-cyclopropyl(phenyl)methyl)-2-isocyanoacetamide as an intermediate.

A mixture of N-((S)-cyclopropyl(phenyl)methyl)-2-isocyanoacetamide (1 mmol), 6-substituted-2-pyridinecarboxyaldehyde (1 mmol), and piperidine (catalytic, 1 drop) in acetonitrile (50 ml) was prepared and refluxed for 24 hr. Solvent was evaporated to dryness and product was purified using LC (Biotage SP1, purification system) to give WP1140 (WP1193) as a white powder (50%).

Synthesis of WP1204

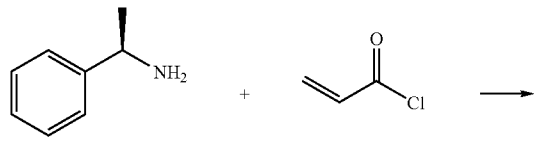

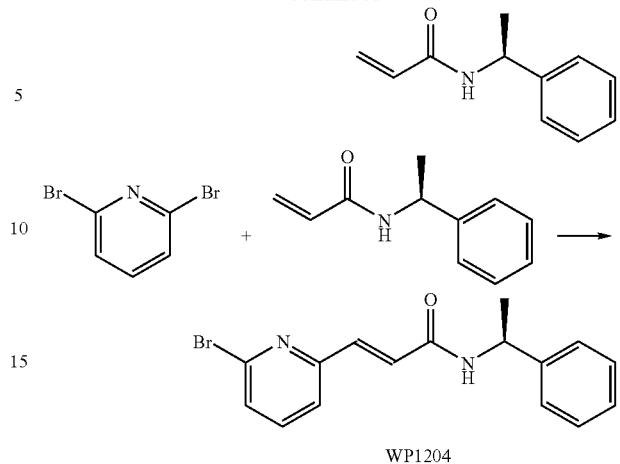

Synthesis of N-((S)-1-phenylethyl)acrylamide

S-(α)-Methylbenzylamine (6 mL) was dissolved in dry dichloromethane (10 mL), cooled down to 0° C. and then the acroyl chloride (4 mL) was added dropwise. The reaction mixture was stirred at room temperature for 15 min, then solvent was evaporated to dryness. Crude product was purified by column chromatography using hexanes, hexanes: ethyl acetate 9:1 to give with a good yield a pure N-((S)-1-phenylethyl)acrylamide.

Synthesis of (E)-3-(6-bromopyridin-2-yl)-N-((S)-1-phenylethyl)acrylamide

To the solution of triphenylphosphine (0.496 mmol) in DMF (10 mL), a palladium acetate (0.245 mmol) was added at room temperature under argon atmosphere. The mixture was stirred for 5 min then 2,6-dibromopyridine (12.7 mmol) followed by N-((S)-1-phenylethyl)acrylamide (14.0 mmol) and triethylamine (35.9 mmol) were added and the reaction mixture was stirred at 140° C. for 7 hr. The majority of the solvent was removed under diminished pressure. Diluted HCl was added and the product was extracted with ethyl acetate. Organic layers were combined, washed with brine, dried over sodium sulfate. Drying agent and solvent was removed and product was purified by column chromatography using hexanes and hexanes:ethyl acetate 2:1 as eluents, to give pure product with a good yield.

EXAMPLE 2

NMR Chemical Shifts of Selected Compounds

The following compounds were prepared according to the procedure indicated above.

WP1082

(2E)-N-benzyl-2-cyano-3-(cyclohex-3-enyl)acylamide $^1$HNMR (CDCl$_3$, δ) ppm 7.78 (d, 1H, J=10.5 Hz, H-3), 7.40-7.32 (m, 5H, Haromat. from benzyl), 6.54 (bs, 1H, NH), 5.79 (m, 1H, H-3'), 5.71 (dddd, 1H, J=11.8 Hz, J=6.4 Hz, J=4.3 Hz, J=2.0 Hz, H-4'), 3.01-2.93 (m, 1H, H-1'), 4.57 (d, 2H, J=5.7 Hz, CH₂ from benzyl), 2.23-2.14 (m, 3H, 2', 2', 6'), 2.05-2.00 (m, 1H, 6'), 1.86-1.83 (m, 1H, 6'), 1.66-1.60 (m, 2H, 5', 5')

WP1193

(E)-3-(6-bromopyridin-2-yl)-2-cyano-N-((S)-cyclopropyl(phenyl)methyl)acrylamide

¹HNMR (CDCl₃, δ) ppm: 8.22 (s, 1H, H-3), 7.68 (dd, 1H, J=8.9 Hz, J=6.3 Hz, H-4'), 7.60 (d, 1H, J=6.3 Hz, H-5'), 7.59 (d, 1H, J=8.5 Hz, H-3'), 7.43-7.28 (m, 5H, phenyl), 7.02 (d, 1H, J=7.5 Hz, NH), 4.53 (dd, 1H, J=J=8.5 Hz, H-1"), 1.37-1.23 (m, 1H, H-2"), 0.74-0.64 (m, 2H, CH₂-cyclopropyl), 0.55-0.42 (m, 2H, CH₂-cyclopropyl)

WP1145

(E)-3-(6-bromopyridin-2-yl)-2-cyano-N-((S)-1,2-diphenylethyl)acrylamide

¹HNMR (CDCl₃, δ) ppm: 8.13 (s, 1H, H-3), 7.66 (dd, 1H, J=7.9 Hz, J=7.3 Hz, H-4'), 7.58 (dd, H, J=7.9 Hz, J=1.1 Hz, H-5'), 7.56 (dd, 1H, J=7.3 Hz, J=1 Hz, H-3'), 7.39-7.11 (m, 10H, phenyl), 6.93 (d, 1H, J=7.3 Hz, NH), 5.38 (ddd, 1H, J=J=7.7 Hz, J=14.4 Hz, H-1"), 3.25 (dd, H, J=14.3 Hz, J=6.4 Hz, H-2"), 3.17 (dd, H, J=14.3 Hz, J=6.4 Hz, H-2")

WP1159

(E)-3-(6-bromopyridin-2-yl)-2-cyano-N-(2-phenoxyethyl)acrylamide

¹HNMR (CDCl₃, δ) ppm: 8.22 (s, 1H, H-3), 7.67 (dd, 1H, J=J=7.5 Hz, H-4'), 7.61 (dd, 1H, J=7.5 Hz, J=1.5 Hz, H-5'), 7.58 (dd, 1H, J=7.5 Hz, J=1.5 Hz, H-3'), 7.32-7.27 (m, 3H, phenyl), 7.04 (bs, 1H, NH), 7.00-6.91 (m, 2H, phenyl), 4.14 (t, 2H, J=5.1 Hz, H-2"), 3.85 (dd, 2H, J=10.7 Hz, J=5.1 Hz, H-1")

WP1163

(E)-3-(6-bromopyridin-2-yl)-2-cyano-N-((R)-cyclopropyl(phenyl)methyl)acrylamide

¹HNMR (CDCl₃, δ) ppm: 8.19 (s, 1H, H-3), 7.66 (dd, 1H, J=9.0 Hz, J=6.4 Hz, H-4'), 7.575 (d, 1H, J=6.4 Hz, H-5'), 7.57 (d, 1H, J=9.0 Hz, H-3'), 7.41-7.26 (m, 5H, phenyl), 7.01 (d, 1H, J=7.5 Hz, NH), 4.50 (dd, 1H, J=J=8.3 Hz, H-1"), 1.35-1.23 (m, 1H, H-2"), 0.72-0.62 (m, 2H, CH₂-cyclopropyl), 0.54-0.40 (m, 2H, CH₂-cyclopropyl)

WP1164

(E)-3-(6-bromopyridin-2-yl)-2-cyano-N-((S)-cyclobutyl(phenyl)methyl)acrylamide

¹HNMR (CDCl₃, δ) ppm: 8.18 (s, 1H, H-3), 7.65 (dd, 1H, J=J=7.5 Hz, H-4'), 7.57 (d, 1H, J=7.5 Hz, H-5'), 7.56 (d, 1H, J=7.5 Hz, H-3'), 7.36-7.24 (m, 5H, phenyl), 6.74 (d, 1H, J=8.0 Hz, NH), 5.05 (dd, H, J=J=9.0 Hz, H-1"), 2.78 (dd, 1H, J=J=9.0 Hz, H-2"), 2.16-1.75 (m, 6H, CH₂ from cyclobutyl)

WP1166

(E)-3-(6-bromopyridin-2-yl)-2-cyano-N-((S)-cyclohexyl(phenyl)methyl)acrylamide

¹HNMR (CDCl₃, δ) ppm: 8.19 (s, 1H, H-3), 7.68 (dd, 1H, J=8.0 Hz, J=7.3 Hz, H-4'), 7.59 (dd, H, J=8.0 Hz, J=1.1 Hz, H-5'), 7.58 (dd, 1H, J=7.3 Hz, J=1.1 Hz, H-3'), 7.40-7.29 (m, 5H, phenyl), 6.90 (d, 1H, J=9.2 Hz, NH), 4.87 (dd, 1H, J=J=8.5 Hz, H-1"), 1.93-0.9 (m, 10 H, H-cyclohexyl).

WP1167

(E)-3-(6-bromopyridin-2-yl)-2-cyano-N-((1S,2R)-2,3-dihydro-2-hydroxy-1H-inden-1-yl)acrylamide ¹HNMR (DMSO-d6, δ) ppm: 8.25 (s, 1H, H-3), 8.24 (d, 1H, J=8.2 Hz, NH), 7.96 (dd, H, J=7.6 Hz, Hz, H-4'), 7.89 (dd, 1H, J=7.6 Hz, J=1.0 Hz, H-5'), 7.82 (dd, 1H, J=7.6 Hz, J=1.1 Hz, H-3'), 7.27-7.21 (m, 4H, H aromat from inden), 5.38 (d, 1H, J=4.5 Hz, OH), 5.34 (dd, 1H, J=8.5 Hz, J=5.2 Hz, H-1"), 4.53 (ddd, 1H, J=8.2 Hz, J=4.7 Hz, J=1.3 Hz, H-2"), 3.13 (dd, 1H, J=16.4 Hz, J=5.3 Hz, H-3"), 2.87 (d, 1H, J=16.4 Hz, H-3")

WP1168

(E)-3-(6-bromopyridin-2-yl)-2-cyano-N-((1R,2S)-2,3-dihydro-2-hydroxy-1H-inden-1-yl)acrylamide ¹HNMR (DMSO-d6, δ) ppm: 8.25 (s, 1H, H-3), 8.24 (d, 1H, J=8.2 Hz, NH), 7.96 (dd, 1H, J=7.6 Hz, Hz, H-4'), 7.90 (dd, 1H, J=7.6 Hz, J=1.0 Hz, H-5'), 7.82 (dd, 1H, J=7.6 Hz, J=1.0 Hz, H-3'), 7.29-7.21 (m, 4H, H aromat from inden), 5.38 (d, 1H, J=4.5 Hz, OH), 5.33 (dd, 1H, J=8.4 Hz, J=5.2 Hz, H-1"), 4.54 (dd, 1H, J=4.7 Hz, J=1.8 Hz, H-2"), 3.13 (dd, 1H, J=16.4 Hz, J=5.2 Hz, H-3"), 2.87 (dd, 1H, J=16.4 Hz, J=1.3 Hz, H-3")

WP1169

(E)-N-benzhydryl-3-(6-bromopyridin-2-yl)-2-cyanoacrylamide

¹HNMR (CDCl₃, δ) ppm: 8.24 (s, 1H, H-3), 7.67 (dd, 1H, J=J=7.6 Hz, H-4'), 7.60 (d, 1H, J=7.6 Hz, H-5'), 7.59 (d, 1H, J=7.6 Hz, H-3'), 7.40-7.27 (m, 10H, phenyl), 7.16 (d, H, J=7.5 Hz, NH), 6.37 (d, H, J=8.0 Hz, H-1")

WP1179

(E)-2-cyano-3-(6-methylpyridin-2-yl)-N-((S)-1-phenylethyl)acrylamide)

¹HNMR (CDCl₃, δ) ppm: 8.29 (s, 1H, H-3), 7.70 (dd, 1H, J=J=7.7 Hz, H-4'),), 7.44-7.26 (m, 7H, H-3', H-5' and phenyl), 6.81 (d, 1H, J=7.2 Hz, NH), 5.28 (dt, 1H, J=14.4 Hz, J=6.9 Hz, H-1"), 2.66 (s, 3H, Me from methylpyridin), 1.63 (d, 3H, J=6.9 Hz, Me)

WP1180

(E)-2-cyano-3-(6-methylpyridin-2-yl)-N-((R)-1-phenylethyl)acrylamide

¹HNMR (CDCl₃, δ) ppm: 8.29 (s, 1H, H-3), 7.70 (dd, 1H, J=J=7.8 Hz, H-4'),), 7.44-7.26 (m, 7H, H-3', H-5' and phenyl), 6.81 (d, 1H, J=7.2 Hz, NH), 5.16 (dt, 1H, J=14.2 Hz, J=7.1 Hz, H-1"), 2.66 (s, 3H, Me from methylpyridin), 1.63 (d, 3H, J=7.1 Hz, Me)

WP1196

(E)-2-cyano-3-(1H-imidazol-2-yl)-N-((S)-1-phenyl-ethyl)acrylamide $^1$HNMR (CDCl$_3$, δ) ppm: 11.25 (bs, 1H, NH), 8.39 (s, 1H, H-3), 7.44-7.26 (m, 7H, H-2', H-3' and phenyl), 7.00 (bs, 1H, NH), 6.76 (d, 1H, J=6.6 Hz, NHCO), 5.20 (dt, 1H, J=14.0 Hz, J=7.1 Hz, H-1"), 1.63 (d, 3H, J=7.1 Hz, Me)

WP1203

(E)-2-cyano-3-cyclododecyl-N-((S)-1-phenylethyl)acrylamide $^1$HNMR (CDCl$_3$, δ) ppm: 7.33-7.20 (m, 6H, H-3 and phenyl), 6.33 (d, 1H, J=7.0 Hz, NH), 5.16 (dt, 1H, J=14.4 Hz, J=7.0 Hz, H-1"), 2.76 (ddd, 2H, J=J=7.0 Hz, J=3.5 Hz, H-2' or H-12'), 2.54 (dd, 2H, J=J=7.6 Hz, H-2' or H-12'), 1.69-1.37 (m, 22H, H-1', Me and cyclododecyl).

WP1225

(E)-3-(6-chloropyridin-2-yl)-2-cyano-N-((R)-cyclopropyl(phenyl)methyl)acrylamide $^1$HNMR (CDCl$_3$, δ) ppm: 8.25 (s, 1H, H-3), 7.79 (dd, 1H, J=J=7.9 Hz, H-4'), 7.57 (d, 1H, J=7.9 Hz, H-5'), 7.45 (d, 1H, J=7.9 Hz, H-3'), 7.43-7.31 (m, 5H, phenyl), 7.0 (d, 1H, J=7.5 Hz, NH), 4.54 (dd, 1H, J=J=8.5 Hz, H-1"), 1.37-1.26 (m, 1H, H-2"), 0.75-0.65 (m, 2H, CH$_2$-cyclopropyl), 0.58-0.44 (m, 2H, CH$_2$-cyclopropyl)

WP1246

(6-((E)-2-((S)-cyclopropyl(phenyl)methylcarbamoyl)-2-cyanovinyl)pyridin-2-yl)methyl acetate $^1$HNMR (CDCl$_3$, δ) ppm: 8.28 (s, 1H, H-3), 7.83 (dd, 1H, J=J=7.8 Hz, H-4'), 7.52 (d, 1H, J=7.8 Hz, H-5'), 7.45 (d, 1H, J=7.8 Hz, H-3'), 7.43-7.29 (m, 5H, phenyl), 7.02 (d, 1H, J=7.7 Hz, NH), 5.34 (s, 2H, CH$_2$Ac), 4.53 (dd, H, J=J=8.4 Hz, H-1"), 2.22 (s, 3H, Ac), 1.37-1.26 (m, 1H, H-2"), 0.71-0.67 (m, 2H, CH$_2$-cyclopropyl), 0.53-0.45 (m, 2H, CH$_2$-cyclopropyl)

WP1267

(E)-3-(6-bromopyridin-2-yl)-2-cyano-N-((R)-cyclobutyl(phenyl)methyl)acrylamide $^1$HNMR (CDCl$_3$, δ) ppm: 8.20 (s, 1H, H-3), 7.68 (dd, 1H, J=8.0 Hz, J=7.1 Hz, H-4'), 7.59 (dd, H, J=8.0 Hz, J=1.0 Hz, H-5'), 7.58 (d, 1H, J=7.5 Hz, J=1.0 Hz, H-3'), 7.38-7.26 (m, 5H, phenyl), 6.75 (d, 1H, J=8.5 Hz, NH), 5.08 (dd, 1H, J=J=9.8 Hz, H-1"), 2.85-2.76 (m, 1H, H-2"), 2.16-1.78 (m, 6H, CH$_2$ from cyclobutyl)

WP1268

(E)-3-(6-bromopyridin-2-yl)-2-cyano-N-((S)-1-hydroxy-3-phenylpropan-2-yl)acrylamide $^1$HNMR (CDCl$_3$, δ) ppm: 8.22 (s, 1H, H-3), 7.71 (dd, 1H, J=J=7.65 Hz, H-4'), 7.66 (d, 1H, J=7.65 Hz, H-5'), 7.63 (d, 1H, J=7.65 Hz, H-3'), 7.40-7.28 (m, 5H, phenyl), 6.85 (d, 1H, J=7.1 Hz, NH), 4.4-4.37 (m, 1H, H-1"), 3.83 (dd, 1H, J=11 Hz, J=3.6 Hz, CH$_2$Ph), 3.75 (dd, 1H, J=11 Hz, J=4.9 Hz, CH$_2$Ph), 3.08 (dd, 1H, J=13.75 Hz, J=7.15 Hz, CH$_2$OH), 3.01 (dd, 1H, J=13.75 Hz, J=7.15 Hz, CH$_2$OH), 2.22 (bs, 1H, OH)

WP1269

(E)-3-(6-bromopyridin-2-yl)-2-cyano-N-((R)-2-hydroxy-1-phenylethyl)acrylamide $^1$HNMR (CDCl$_3$, δ) ppm: 8.26 (s, 1H, H-3), 7.71 (dd, 1H, J=J=7.65 Hz, H-4'), 7.66 (d, 1H, J=7.65 Hz, H-5'), 7.64 (d, 1H, J=7.65 Hz, H-3'), 7.45-7.38 (m, 5H, phenyl), 7.27 (bs, 1H, NH), 5.29-5.26 (m, 1H, H-1"), 4.05-4.04 (m, 2H, CH$_2$OH), 2.06 (bs, 1H, OH)

WP1271

(E)-2-cyano-3-(2-fluoropyridin-3-yl)-N-((S)-1-phenylethyl)acrylamide $^1$HNMR (CDCl$_3$, δ) ppm: 8.61 (ddd, 1H, J=9.4 Hz, J=7.8 Hz, J=1.5 Hz, H-6'), 8.51 (s, 1H, H-3), 8.31 (m, 1H, H-4'), 7.42-7.26 (m, 6H, H-5' and phenyl), 6.54 (d, 1H, J=7.2 Hz, NH), 5.25 (dt, 1H, J=14.1 Hz, J=6.8 Hz, H-1"), 1.62 (d, 3H, J=6.9 Hz, Me)

WP1272

(E)-2-cyano-N-((S)-cyclopropyl(phenyl)methyl)-3-(2-fluoropyridin-3-yl)acrylamide $^1$HNMR (CDCl$_3$, δ) ppm: 8.63 (ddd, 1H, J=9.4 Hz, J=7.9 Hz, J=1.5 Hz, H-6'), 8.51 (s, 1H, H-3), 8.37 (m, 1H, H-4'), 7.41-7.27 (m, 6H, H-5' and phenyl), 6.77 (d, 1H, J=7.1 Hz, NH), 4.51 (dd, 1H, J=J=8.3 Hz, H-1"), 1.35-1.23 (m, 1H, H-2"), 0.73-0.41 (m, 4H, CH$_2$ from cyclopropyl)

WP1280

(E)-2-cyano-3-(3-fluoropyridin-4-yl)-N-((S)-1-phenylethyl)acrylamide $^1$HNMR (CDCl$_3$, δ) ppm: 8.65 (d, 1H, J=1.5 Hz, H-2'), 8.59 (d, 1H, J=5.1 Hz, H-6'), 8.52 (d, 1H, J=0.6 Hz, H-3), 7.95 (dd, 1H, J=J=5.4 Hz, H-5'), 7.42-7.29 (m, 5H, phenyl), 6.59 (d, 1H, J=6.6 Hz, NH), 5.25 (dd, 1H, J=J=7.2 Hz, H-1"), 1.62 (d, 3H, J=6.9 Hz, Me)

WP1282

(E)-3-(6-bromopyridin-2-yl)-2-cyano-N-((R)-cyclopentyl(phenyl)methyl)acrylamide $^1$HNMR (CDCl$_3$, δ) ppm: 8.16 (s, 1H, H-3), 7.65 (dd, 1H, J=J=8.0 Hz, H-4'), 7.58 (d, 1H, J=8.0 Hz, H-5'), 7.55 (d, 1H, J=8.00 Hz, H-3'), 7.36-7.28 (m, 5H, phenyl), 6.09 (d, 1H, J=8.0 Hz, NH), 4.86 (dt, 1H, J=J=9.5 Hz, H-1"), 2.37 (ddd, 1H, J=J=10.2 Hz, J=5.1 Hz, H-2"), 1.92-1.18 (m, 8H, CH$_2$ from cyclopentyl)

WP1283

(E)-3-(3-bromopyridin-4-yl)-2-cyano-N-((S)-1-phenylethyl)acrylamide $^1$HNMR (CDCl$_3$, δ) ppm: 8.87 (s, 1H, H-2'), 8.67 (d, 1H, J=5.1 Hz, H-6'), 8.53 (s, 1H, H-3), 7.79 (dd, 1H, J=J=5.1 Hz, H-5'), 7.41-7.29 (m, 5H, phenyl), 6.61 (d, 1H, J=7.2 Hz, NH), 5.25 (dt, 1H, J=14.2 Hz, J=7.2 Hz, H-1"), 1.62 (d, 3H, J=6.9 Hz, Me)

WP1284

(E)-3-(5-bromopyridin-3-yl)-2-cyano-N-((S)-1-phenylethyl)acrylamide $^1$HNMR (CDCl$_3$, δ) ppm: 8.86 (d, 1H, J=2.1 Hz, H-6'), 8.79 (d, 1H, J=2.1 Hz, H-2'), 8.46 (dd, 1H, J=J=2.1 Hz, H-4'), 8.26 (s, 1H, H-3), 7.42-7.29 (m, 5H, phenyl), 6.55 (d, 1H, J=8.1 Hz, NH), 5.25 (dt, 1H, J=14.1 Hz, J=6.9 Hz, H-1"), 1.62 (d, 3H, J=6.9 Hz, Me)

WP1285

(E)-3-(2-bromopyridin-3-yl)-2-cyano-N-((S)-1-phenylethyl)acrylamide $^1$HNMR (CDCl$_3$, δ) ppm: 8.59 (d, 1H, J=3.0 Hz, H-3), 8.47 (dd, 1H, J=4.8 Hz, J=1.8 Hz, H-6'), 8.28 (ddd, 1H, J=7.5 Hz, J=1.8 Hz, J=0.6 Hz, H-4'), 7.41 (ddd, 1H, J=8.1 Hz, J=4.8 Hz, J=0.6 Hz, H-5'), 7.39-7.29 (m, 5H, phenyl), 6.55 (d, 1H, J=7.5 Hz, NH), 5.25 (dt, 1H, J=14.1 Hz, J=7.2 Hz, H-1"), 1.62 (d, 3H, J=7.2 Hz, Me)

WP1286

(E)-3-(6-bromopyridin-3-yl)-2-cyano-N-((S)-1-phenylethyl)acrylamide $^1$HNMR (CDCl$_3$, δ) ppm: 8.66 (d, 1H, J=2.1 Hz, H-2'), 8.27 (s, 1H, H-3), 8.23 (dd, 1H, J=8.4 Hz, J=2.4 Hz, H-4'), 7.63 (d, 1H, J=7.8 Hz, H-5'), 7.35-7.26 (m, 5H, phenyl), 6.56 (d, 1H, J=6.9 Hz, NH), 5.24 (dt, 1H, J=14.1 Hz, J=7.2 Hz, H-1"), 1.61 (d, 3H, J=7.2 Hz, Me)

WP1293

(R)-2-((E)-3-(6-bromopyridin-2-yl)-2-cyanoacrylamido)-2-phenylethyl acetate $^1$HNMR (CDCl$_3$, δ) ppm: 8.19 (s, 1H, H-3), 7.67 (dd, 1H, J=7.5 Hz, H-4'), 7.59 (dd, 1H, J=7.5 Hz, J=1.2 Hz, H-5'), 7.58 (dd, 1H, J=7.5 Hz, J=1.2 Hz, H-3'), 7.41-7.21 (m, 5H, phenyl), 7.22 (d, 1H, J=7.8 Hz, NH), 5.40 (dt, 1H, J=11.4 Hz, J=6.0 Hz, H-1"), 4.43 (d, 2H, J=6.3 Hz, CH$_2$OAc), 2.08 (s, 3H, OAc)

WP1302

(R)-2-((E)-3-(6-bromopyridin-2-yl)-2-cyanoacrylamido)-2-phenylethyl pivalate $^1$HNMR (CDCl$_3$, δ) ppm: 8.19 (s, 1H, H-3), 7.67 (dd, 1H, J=8.7 Hz, J=6.3 Hz, H-4'), 7.59 (d, 1H, J=6.3 Hz, H-5'), 7.58 (d, 1H, J=8.7 Hz, H-3'), 7.38-7.30 (m, 5H, phenyl), 7.26 (d, 1H, J=6.5 Hz, NH), 5.43 (dt, 1H, J=11.4 Hz, J=5.4 Hz, H-1"), 4.43 (d, 2H, J=5.4 Hz, CH$_2$O), 2.08 (s, 9H, CH$_3$)

Synthesis of WP1201 ((S)-N-((E)-2-(6-bromopyridin-2-yl)vinylsulfonyl)-1-phenylethanamine)

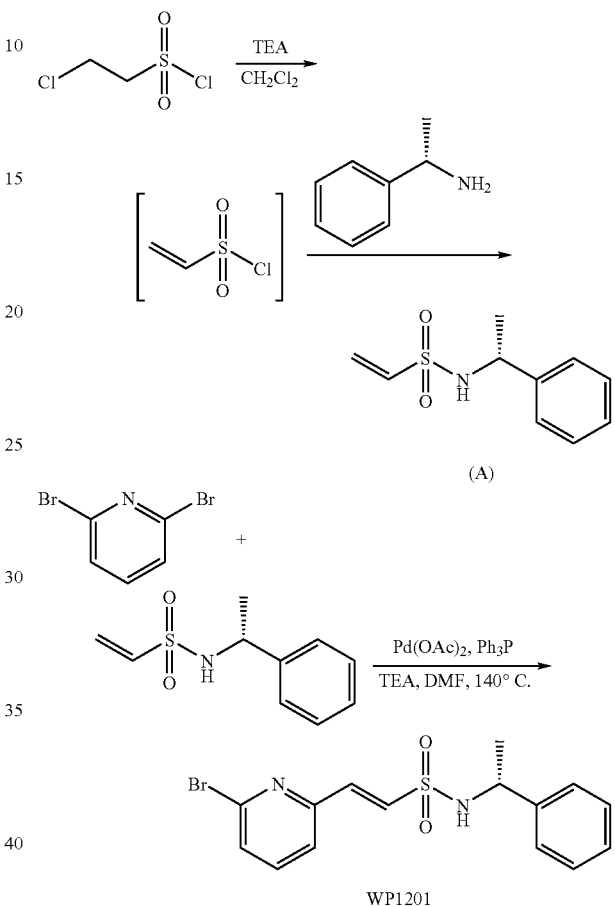

2-Chloroethanesulfonyl chloride (5.7 mmol, 930 mg) was dissolved in dichloromethane (10 mL). Obtained solution was cooled down to −78° C. Triethylamine (TEA), (5.7 mmol, 0.8 mL) was added, and the reaction mixture was stirred at −78° C. for 30 min, then for 45 min at 0° C. The reaction mixture was cooled to −78° C. and the mixture of (S)-methylbenzylamine (5.7 mmol, 690 mg) and TEA (5.7 mmol, 0.8 mL) in dichloromethane (10 mL) was added. Stirring at −78° C. was continued for additional 20 min, then cooling bath was removed and the reaction mixture was stirred for 20 min at rt. Solvents were evaporated to dryness, and crude product was purified by LC chromatography (ISCO LC purification system) using hexanes:ethyl acetate gradient up to 50% ethyl acetate as eluent, to give 0.78 g of sulfonamide (A) (yield 65%).

Triphenylphosphine (1.1 mmol, 28 mg) was dissolved in DMF (3 mL). Palladium (II) acetate (0.53 mmol, 113.5 mg) was added and the mixture was stirred under Ar for 5 min. Sulfonamide (A) (2.8 mmol, 600 mg), 2,6-dibromopyridine (2.8 mmol, 640 mg), TEA (1 mL) and DMF (3 mL) were added and the mixture was heated under reflux for 2.5 hr. The reaction mixture was cooled down, then diluted with water (50 mL). Obtained mixture was extracted with ethyl acetate (3×50 mL). Combined extracts were dried over sodium sulfate. Product was purified by LC (BIOTAGE LC purification system) using hexanes:ethyl acetate gradient up to 50% ethyl acetate as eluent, to give 460 mg of WP1201 (yield 45%)

$^1$HNMR (CDCl$_3$, δ) ppm: 7.55 (dd, 1H, J=8.0 Hz, J=7.4 Hz, H-4'),), 7.46 (dd, 1H, J=8.0 Hz, J=0.9 Hz, H-5') 7.33-7.20 (m, 5H, phenyl), 7.17 (dd, 1H, J=7.4 Hz, J=0.9 Hz, H-3'), 7.17 (d, 1H, J=14.9 Hz, H-3), 7.09 (d, 1H, J=14.9 Hz, H-2), 4.80 (d, 1H, J=7.1 Hz, NH), 4.62 (dt, 1H, J=13.8 Hz, J=6.9 Hz, H-1"), 1.59 (d, 3H, J=6.9 Hz, Me)

EXAMPLE 3

General Assay Methods

Cell Cultures

Glioblastoma U87 and pancreatic cancer cell lines, AsPc-1, Panc-1, Colo357-FG and Colo357-L3.6 were maintained in DMEM with 10% fetal bovine serum (FBS), 100 mg/ml streptomycin, and 100 IU/ml penicillin in 5% $CO_2$ at 37° C.

Tumor cell lines, were maintained in DMEM with 10% fetal bovine serum (FBS), 100 microg/ml streptomycin, and 100 IU/ml penicillin in 5% $CO_2$ at 37° C.

AsPc-1: A human pancreatic tumor cell line established from the ascites of a patient with histopathologically confirmed adenocarcinoma of the head of the pancreas. See Chen et al. (1982).

Panc-1: An epithelioid cell line started from a human pancreatic carcinoma of ductal cell origin. See Lieber et al. (1975).

Colo357 was derived from a metastasis of a pancreatic adenocarcinoma. See Morgan et al. (1980).

Colo357-FG and Colo357-L3: Colo357-FG, a fast-growing variant produced regional lymph node metastasis in 58% of nude mice after subcutaneous implantation and growth. It also produced hepatic metastasis in 64% and pulmonary metastasis in 43% of nude mice after intrasplenic implantation of tumor cells. See Vezeridis et al. (1990).

Colo357-L3.5 established by sequential passages of a human pancreatic cancer cell line through the nude mouse liver. See Vezeridis et al. (1992).

WM793 human melanoma tumor cell lines were used from different stages of progression and their biological and molecular analyses. See Satyamoorthy et al. (1997).

Cytotoxicity Assay

For the cytotoxicity assays, 1,500 tumor cells were plated into 96-well flat-bottom tissue culture plates in complete medium. After 20 hours fresh media containing different concentrations of WP1066 was added. Cell number was counted after 72 hours by using MTS assay (Promega CellTiter AQ Non-Radioactive Cell Proliferation Assay kit, Madison, Wis., USA) by measuring absorbance at 490 nm with a 96-well plate reader. Data are presented as relative inhibition of proliferation plus SD of eight measurements. The number of cells in the presence of DMSO was taken as 100%.

Apoptosis Assay $6 \times 10^5$ cultured pancreatic cancer cells were plated on 100-mm dishes for 24 h before treatment. Following treatment with different times and concentrations of WP1066 or DMSO (solvent) cells were stained with Annexin V-FITC. Fluorescence was quantified on a Becton Dickinson (San Jose, Calif.) FACScan for at least 10,000 events.

Western Blot Analysis

Cultured pancreatic cancer cells treated with different times and concentrations of WP compounds or DMSO (solvent) were lysed in lysis buffer and equal amounts of protein extracts were fractionated by sodium dodecyl sulfate polyacrylamide gel electrophoresis and transferred to Hybond-P membranes. Membranes were immuno-blotted using phospho-specific STAT3, total STAT3, Bcl-xL, survivin, PARP, caspase-8 and GADPH antibodies. The primary antibodies were visualized with goat anti-rabbit or goat anti-mouse peroxidase-conjugated antibodies using an enhanced chemiluminescence (ECF) system and a Molecular Dynamics Storm PhosphorImager.

All of the compositions disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,433,018
U.S. Pat. No. 6,420,338
U.S. Pat. No. 6,426,366
Arbel et al., *Am. J. Obstet. Gynecol.*, 188(5):1283-90, 2003.
Bharti et al., *J. Immunol.*, 171(7):3863-3871, 2003.
Burdelya et al., *Mol. Cancer Ther.*, 1(11):893-9, 2002.
Catlett-Falcone et al., *Immunity*, 10(1):105-15, 1999.
Chen et al., *In Vitro*, 18(1):24-34, 1982.
Constantin et al., *Eur. J. Immunol.*, 28(11):3523-9, 1998.
Hallek et al., *Blood*, 91(1):3-21, 1998.
Hideshima et al., *J. Biol. Chem.*, 277(19):16639-47, 2002.
Iwamarul et al., *Oncogene*, 1-10, 2006.
Jernberg-Wiklund et al., *Int. J. Cancer*, 51(1):116-23, 1992.
Kerr et al., *FEBS Lett.*, 546(1):1-5, 2003.
Kuehl et al., *Curr. Top Microbiol. Immunol.*, 224:277-82, 1997.
Lieber et al., *Int. J. Cancer*, 15(5):741-747, 1975.
Meydan et al., *Nature*, 379(6566):645-8, 1996.
Morgan et al., *Int. J. Cancer*, 25(5):591-598, 1980.
Remington's Pharmaceutical Sciences" 15th Edition, pages 1035-1038 and 1570-1580.
Satyamoorthy et al., *Melanoma Res.*, 7(Suppl. 2):S35-S42, 1997. Alas and Bonavida, *Clin. Cancer Res.*, 9(1):316-26, 2003.
Selvanayagam et al., *Blood*, 71(1):30-5, 1988.
Verma et al., *Cancer Metastasis Rev.*, 22(4):423-34, 2003.
Vezeridis et al., *Cancer*, 69(8):2060-2063, 1992.
Vezeridis et al., *J. Surg. Res.*, 48(1):51-55, 1990.
Wermuth and Stahl, In: *Pharmaceutical Salts: Properties, Selection and Use*—A Handbook, Verlag Helvetica Chimica Acta, 2002.
World Health Organization grades II-IV, Kleihues et al. (Eds.), 2002.
Yu and Jove, *Nature Rev. Cancer*, 4(2):97-105, 2004.

What is claimed is:

1. A compound selected from the group consisting of:

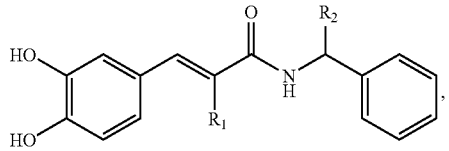

wherein $R_1$ is —H or cyano and $R_2$ is heteroatom-unsubstituted $C_3$-$C_7$-cycloalkyl;

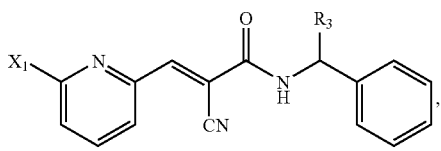

wherein $X_1$ is halo and $R_3$ is heteroatom-unsubstituted $C_3$-$C_7$-cycloalkyl, $C_6$-$C_{10}$-aryl, or $C_7$-$C_{10}$-aralkyl;

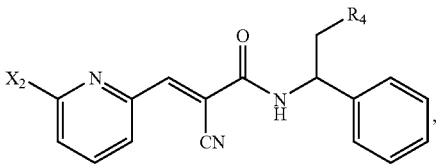

wherein $X_2$ is halo and $R_4$ is hydroxy or heteroatom-unsubstituted $C_1$-$C_{10}$-acyloxy;

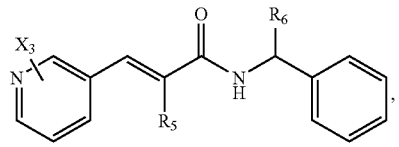

wherein:
$X_3$ is halo or heteroatom-unsubstituted $C_1$-$C_{10}$-alkyl or $C_1$-$C_{10}$-alkoxy,
$R_5$ is —H or cyano, and
$R_6$ is heteroatom-unsubstituted $C_3$-$C_7$-cycloalkyl, $C_1$-$C_{10}$-acyloxy, $C_6$-$C_{10}$-aryl, or $C_7$-$C_{10}$-aralkyl;

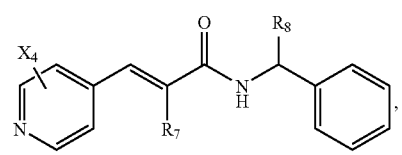

wherein:
$X_4$ is halo or heteroatom-unsubstituted $C_1$-$C_{10}$-alkyl or $C_1$-$C_{10}$-alkoxy,
$R_7$ is —H or cyano, and
$R_8$ is a heteroatom-unsubstituted $C_3$-$C_7$-cycloalkyl, $C_1$-$C_{10}$-acyloxy, $C_6$-$C_{10}$-aryl, or $C_7$-$C_{10}$-aralkyl;

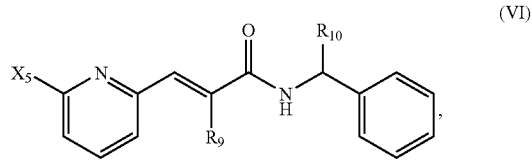

wherein:
$X_5$ is heteroatom-unsubstituted $C_1$-$C_{10}$-alkyl or $C_1$-$C_{10}$-alkoxy,
$R_9$ is —H or cyano, and
$R_{10}$ is a heteroatom-unsubstituted $C_3$-$C_7$-cycloalkyl, $C_1$-$C_{10}$-acyloxy, $C_6$-$C_{10}$-aryl, or $C_7$-$C_{10}$-aralkyl; and

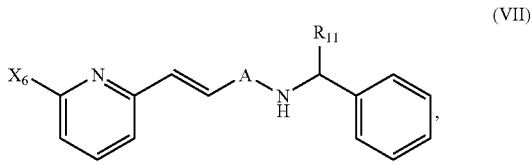

wherein:

A is —C(O)—, and
$X_6$ is halo or heteroatom-unsubstituted $C_1$-$C_{10}$-alkyl or $C_1$-$C_{10}$-alkoxy,
$R_{11}$ is heteroatom-unsubstituted $C_3$-$C_7$-cycloalkyl, $C_1$-$C_{10}$-acyloxy, $C_6$-$C_{10}$-aryl, or $C_7$-$C_{10}$-aralkyl;
or a pharmaceutically acceptable salt or tautomer thereof.

2. The compound of claim 1, wherein $R_2$ is selected from the group consisting of cyclopropyl, cyclobutyl, cyclopentyl and cyclohexyl.

3. The compound of claim 1, wherein $R_3$ is selected from the group consisting of phenyl, benzyl, cyclopropyl, cyclobutyl, cyclopentyl and cyclohexyl.

4. The compound of claim 1, wherein $X_1$ or $X_2$ is selected from the group consisting of —F, —Cl, —Br and —I.

5. The compound of claim 1, wherein $R_4$ is selected from a group consisting of hydroxy, acetoxy and 2,2-dimethylpropionyloxy.

6. The compound of claim 1, wherein $X_3$ or $X_4$ is selected from the group consisting of methoxy, —F, —Cl, —Br and —I.

7. The compound of claim 1, wherein $R_6$ or $R_8$ is cyclopropyl.

8. The compound of claim 1, wherein $X_5$ is methyl.

9. The compound of claim 1, having the formula:

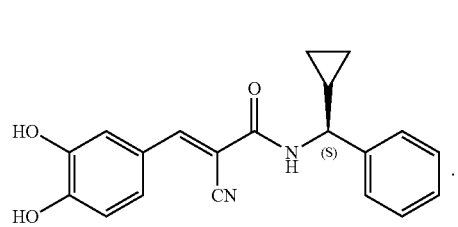
(WP1331)

10. The compound of claim 1, having the formula:

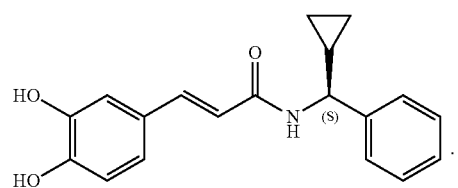
(WP1328)

11. The compound of claim 1, having the formula:

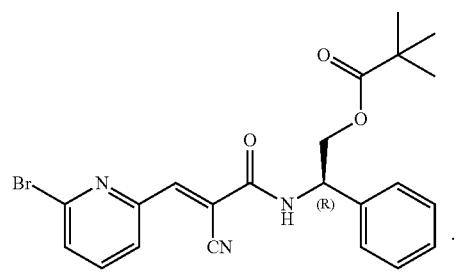
(WP1302)

12. The compound of claim 1, having the formula:

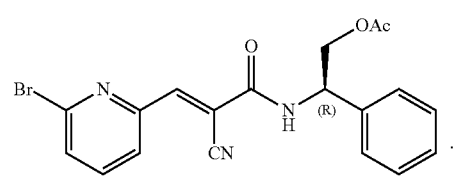
(WP1293)

13. The compound of claim 1, having the formula:

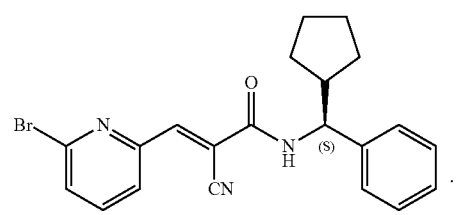
(WP1282)

14. The compound of claim 1, having the formula:

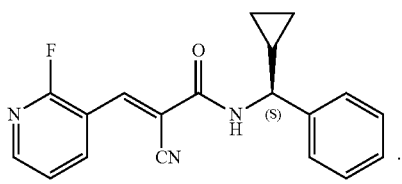
(WP1272)

15. The compound of claim 1, having the formula:

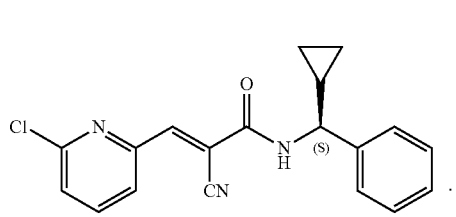
(WP1229)

16. The compound of claim 1, having the formula:

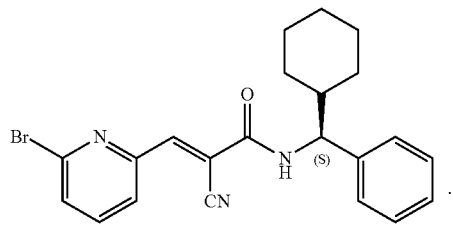
(WP1166)

17. The compound of claim 1, having the formula:

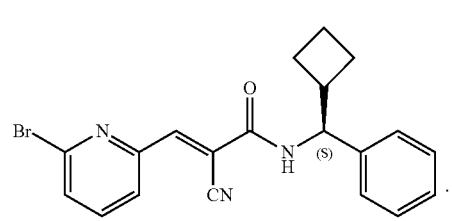
(WP1164)

18. The compound of claim 1, having the formula:

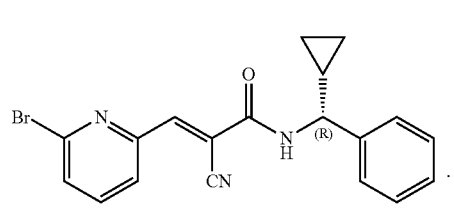
(WP1163)

19. The compound of claim 1, having the formula:

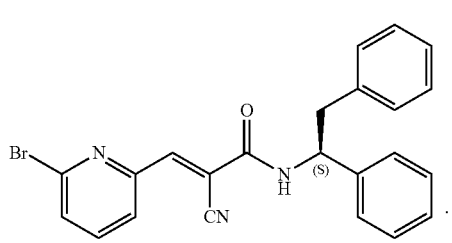
(WP1145)

20. The compound of claim 1, having the formula:

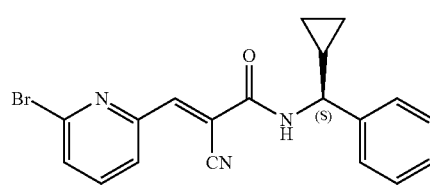
(WP1140, WP1193)

21. The compound of claim 1, further defined as a compound of formula(I).

22. The compound of claim 1, further defined as a compound of formula (II).

23. The compound of claim 1, further defined as a compound of formula (III).

24. The compound of claim 1, further defined as a compound of formula (IV).

25. The compound of claim 1, further defined as a compound of formula (V).

26. The compound of claim 1, further defined as a compound of formula (VI).

27. The compound of claim 1, further defined as a compound of formula (VII).

* * * * *

UNITED STATES PATENT AND TRADEMARK OFFICE
CERTIFICATE OF CORRECTION

PATENT NO. : 8,779,151 B2
APPLICATION NO. : 11/695547
DATED : July 15, 2014
INVENTOR(S) : Priebe et al.

It is certified that error appears in the above-identified patent and that said Letters Patent is hereby corrected as shown below:

On the title page -- Replace 27 Claims, with -- 30 Claims

On the title page, item [56] References Cited - Other Publications, Line 42-46, delete "De Vos et al., "JAK2 tyrosine kinase inhibitor tyrphostin AG490 downregulates the mitogen-activated protein kinase (MAPK) and signal trasducer and activator of transcription (STAT) pathways and induces apoptosis in myeloma cells," *Br. J. Haematol.* 109:823-828, 2000." and replace with --De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells," *Br. J. Haematol.* 109:823-828, 2000.-- therefor.

In the Specification

Column 1, lines 4-7, delete "The U.S. government owns rights in the present invention pursuant to funding from the National Institute of Health through grant number CA101936." and insert --This invention was made with Government support under grant number CA101936 awarded by the National Institutes of Health. The Government has certain rights in the invention.-- therefor.

In the Claims

Claim 5, column 44, line 57, delete "is selected from a" and replace with --is selected from the-- therefor.

Signed and Sealed this
Sixth Day of January, 2015

Michelle K. Lee
*Deputy Director of the United States Patent and Trademark Office*

CERTIFICATE OF CORRECTION (continued)
U.S. Pat. No. 8,779,151 B2

Column 48, line 25, after claim 27, insert

-- 28. The compound claim 1, having the formula:

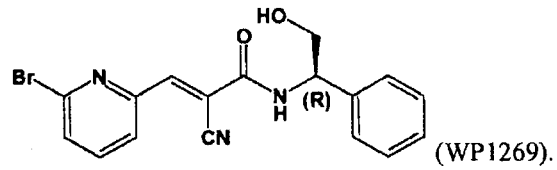 (WP1269).

29. The compound of claim 1, having the formula:

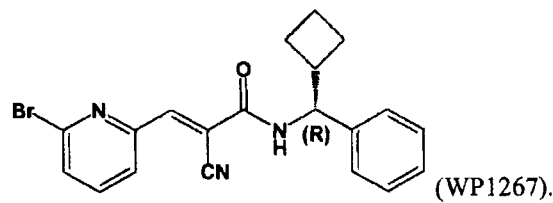 (WP1267).

30. The compound of claim 1, having the formula:

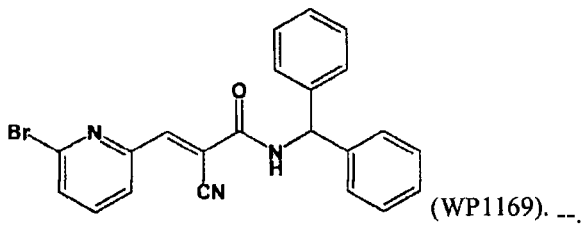 (WP1169). --.

(12) United States Patent
Priebe et al.

(10) Patent No.: US 8,779,151 B2
(45) Date of Patent: Jul. 15, 2014

(54) ORALLY BIOAVAILABLE CAFFEIC ACID RELATED ANTICANCER DRUGS

(75) Inventors: Waldemar Priebe, Houston, TX (US); Izabela Fokt, Houston, TX (US); Slawomir Szymanski, Houston, TX (US); Timothy Madden, Sugar Land, TX (US); Jeffrey Myers, Bellaire, TX (US); Charles Conrad, Spring, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 847 days.

(21) Appl. No.: 11/695,547

(22) Filed: Apr. 2, 2007

(65) Prior Publication Data

US 2007/0232668 A1    Oct. 4, 2007

Related U.S. Application Data

(60) Provisional application No. 60/744,105, filed on Mar. 31, 2006.

(51) Int. Cl.
*C07D 213/57* (2006.01)
*A61K 31/44* (2006.01)

(52) U.S. Cl.
USPC ............ 546/330; 514/357; 558/390; 558/392

(58) Field of Classification Search
USPC ............ 546/300, 330; 514/357; 558/392, 390
See application file for complete search history.

(56) References Cited

U.S. PATENT DOCUMENTS

| | | | |
|---|---|---|---|
| 4,999,357 A | 3/1991 | Gadras et al. | 514/277 |
| 5,196,446 A | 3/1993 | Levitzki et al. | 514/415 |
| 5,700,822 A | 12/1997 | Huth et al. | 514/380 |
| 5,773,476 A | 6/1998 | Chen et al. | 514/620 |
| 5,854,285 A | 12/1998 | Sriram et al. | 514/514 |
| 5,981,569 A | 11/1999 | App et al. | 514/419 |
| 6,194,453 B1 | 2/2001 | Sriram et al. | 514/514 |
| 6,225,346 B1 | 5/2001 | Tang et al. | 514/523 |
| 6,331,555 B1 | 12/2001 | Huth et al. | 514/378 |
| 6,420,338 B1 | 7/2002 | Schneider et al. | 514/12 |
| 6,426,366 B1 | 7/2002 | Novogrodsky et al. | 514/523 |
| 6,433,018 B1 | 8/2002 | Siddiqui et al. | 514/619 |
| 6,555,702 B2 | 4/2003 | Sriram et al. | 558/401 |
| 6,596,828 B1 | 7/2003 | Kaito et al. | 526/164 |
| 6,596,878 B2 | 7/2003 | Chen et al. | 548/371.7 |
| 2002/0045191 A1 | 4/2002 | Schneider et al. | 435/7.1 |
| 2002/0115714 A1 | 8/2002 | Sriram et al. | 514/514 |
| 2003/0013748 A1 | 1/2003 | Novogrodsky et al. | 514/367 |
| 2003/0032596 A1 | 2/2003 | Schneider et al. | 514/12 |

FOREIGN PATENT DOCUMENTS

| | | |
|---|---|---|
| JP | 2003-119169 | 4/2003 |
| WO | WO 91/16305 | 10/1991 |
| WO | WO 95/14464 | 6/1995 |
| WO | WO 95/18606 | 7/1995 |
| WO | WO 95/24190 | 9/1995 |
| WO | WO 98/06391 | 2/1998 |
| WO | WO 2004-047743 | 6/2004 |
| WO | WO 2005/053671 | 6/2005 |
| WO | WO 2005/058829 | 6/2005 |

OTHER PUBLICATIONS

Murata et. al. "Synthesis and structure-activity relationships of novel IKK-b inhibitors. Part 3: Orally active anti-inflammatory agents" Bioorganic & Medicinal Chemistry Letters 2004, 14, 4019-4022.*
PCT International Search Report and Written Opinion, issued in International Application No. PCT/US2007/065805, dated Oct. 17, 2007.
"Design, Synthesis and Structure-Activity Relationships of Novel Jak2/STAT3 Signaling Inhibitors," AACR Abtract Later Breaking News, Feb. 1, 2006 (Abstract No. 06-LBA-8902-AACR).
Alas and Bonavida, "Inhibition of constitutive STAT3 activity sensitizes resistant non-Hodgkin's lymphoma and multiple myeloma to chemotherapeutic drug-mediated apoptosis," *Clin. Cancer Res.*, 9(1):316-26, 2003.
Alcon et al, "Activation of Tyrosine Kinase Pathway by Vanadate in Gallbladder Smooth Muscle." *Biochem. Pharmacol.*, 59:1077-1089, 2000
Arbel et al, "Inhibitors that target protein kinases for the treatment of ovarian carcinoma," *Am. J. Obstet. Gynecol.*, 188(5):1283-90, 2003.
Bharti et al, "Curcumin (diferuloylmethane) inhibits constitutive and IL-6-inducible STAT3 phosphorylation in human multiple myeloma cells," *J. Immunol.*, 171(7):3863-3871, 2003.
Burdelya et al, "Combination therapy with AG-490 and interleukin 12 achieves greater antitumor effects than either agent alone," *Mol. Cancer Ther.*, 1(11):893-9, 2002.
Catlett-Falcone et al., "Constitutive activation of Stat3 signaling confers resistance to apoptosis in human U266 myeloma cells," *Immunity*, 10(1):105-15, 1999.
Chen et al., "Human pancreatic adenocarcinoma: in vitro and in vivo morphology of a new tumor line established from ascites," in Vitro, 18(1):24-34, 1982
Constantin et al., "Tyrphostin AG490, a tyrosine kinase inhibitor, blocks actively induced experimental autoimmune encephalomyelitis." *Eur. J. Immunol.*, 28(11):3523-9, 1998.
De Vos et al., "JAK2 tyrosine kinase inhibitor tyrphostin AG490 downregulates the mitogen-activated protein kinase (MAPK) and signal trasducer and activator of transcription (STAT) pathways and induces apoptosis in myeloma cells," *Br. J. Haematol.* 109:823-828, 2000
Gazit et al., "Tyrphostins. 2. Heterocyclic and alpha-substituted benzylidenemalononitrile tyrphostins as potent inhibitors of EG receptor and ErbB2/neu tyrosine kinases." *J. Med. Chem.*, 34(6):1896-1907, 1991.
Gazit, et al., "Tyrphostins I: synthesis and biological activity of protein tyrosine kinase inhibitors," *J. Med. Chem.*, 32 2344-2352, 1989
Hallek et al., "Multiple myeloma: increasing evidence for a multistep transformation process." *Blood*, 91(1):3-21, 1998.

(Continued)

*Primary Examiner* — David K O Dell
(74) *Attorney, Agent, or Firm* — Parker Highlander PLLC

(57) ABSTRACT

The present invention concerns compounds and their use to treat cell proliferative diseases such as cancer. Compounds of the present invention display significant potency as inhibitors of Jak2/STAT3 pathways and downstream targets and inhibit the growth and survival of cancerous cell lines.

30 Claims, 34 Drawing Sheets